United States Patent
Bloksberg et al.

(10) Patent No.: US 6,653,528 B1
(45) Date of Patent: *Nov. 25, 2003

(54) PINUS RADIATA NUCLEIC ACIDS ENCODING O-METHYL TRANSFERASE AND METHODS FOR THE MODIFICATION OF PLANT LIGNIN CONTENT THEREWITH

(75) Inventors: Leonard N. Bloksberg, Auckland (NZ); Ilkka Havukkala, Auckland (NZ)

(73) Assignees: Genesis Research & Development Corporation Limited, Parnell (NZ); Rubicam Forests Industries Limited, Auckland (NZ)

( * ) Notice: Subject to any disclaimer, the term of this patent is extended or adjusted under 35 U.S.C. 154(b) by 0 days.

This patent is subject to a terminal disclaimer.

(21) Appl. No.: 09/169,789

(22) Filed: Oct. 9, 1998

Related U.S. Application Data

(63) Continuation-in-part of application No. 08/975,316, filed on Nov. 21, 1997, now Pat. No. 5,952,486, which is a continuation-in-part of application No. 08/713,000, filed on Sep. 11, 1996, now Pat. No. 5,850,020.

(51) Int. Cl.$^7$ .............................. A01H 5/00; A01H 5/10; A01H 7/00; C12N 15/29; C12N 15/82; C12N 5/04; C12N 1/21

(52) U.S. Cl. ..................... 800/278; 800/290; 800/298; 800/287; 800/319; 435/419; 435/252.3; 435/320.1; 536/23.6; 536/23.2

(58) Field of Search ............................... 536/23.1, 23.2, 536/23.6, 24.1; 435/69.1, 70.1, 468, 410, 419, 320.1; 800/478, 479, 283, 284, 286, 290, 295, 319, 287, 298

(56) References Cited

U.S. PATENT DOCUMENTS

| | | | | |
|---|---|---|---|---|
| 5,122,466 A | * | 6/1992 | Stomp et al. | 800/293 |
| 5,850,020 A | * | 12/1998 | Bloksberg et al. | 435/320.1 |
| 5,952,486 A | | 9/1999 | Bloksberg et al. | 536/23.6 |
| 6,204,434 B1 | * | 3/2001 | Bloksberg et al. | 435/417 |

FOREIGN PATENT DOCUMENTS

| | | | |
|---|---|---|---|
| NZ | 328434 | 5/1998 | C12N/9/24 |
| WO | 9811205 | 3/1998 | C12N/9/02 |
| WO | 0022099 | 4/2000 | C12N/9/00 |

OTHER PUBLICATIONS

Hill et al., Functional Analysis of Conserved Histdines in ADP–Glucose Phyrophosphorylase from *Escherichia coli*, 1998, Biochemical and Biophysical, vol. 244, pp. 573–577.*
Poedomenge et al., A cDNA Encoding S–Adenosyl–L–Methionine:Caffeic Acid 3–O–Methyltransferase from *Eucalyptus*, 1994, Plant Physiol, vol. 105, pp. 749–750.*
Voo et al., 4–Coumarate: Coenzyme A Ligase from Loblolly Pine Xylem1, 1995, Plant Physiol, vol. 108, pp. 85–97.*
Kajita et al., Alteration in the Biosynthesis of Lignin Transgenic Plant with Chimeric Genes for 4–Coumarate: Coenzyme A Ligase, 1996, Plant Cell Physiol, vol. 37, No. 7, pp. 957–965.*
Franke et al., Modified lignin in tobacco and poplar plant over–expressiing the Arabidopsis gene encoding ferulate 5–hydroxlase, 2000, The Plant Journal, vol. 22, pp. 223–234.*
Piquemal et al., Down–relgulation of Cinnamoyl–CoA Reductase induces significant changes of lignin profiles in transgenic tobacco plants, 1998, The Plant Journal, vol. 13, No. 1, pp. 71–83.*
Kajita et al., Immunological characterization of transgenic tobacco plants with a chimric gene for 4–coumarate . . . , 1997, Plant Science, pp. 109–118.*
Hu et al., Repression of lignin biosynthesis promotes cellulose accoumlation and growth in transgenic tree, Aug. 1999, Nature Biotechnology, vol. 17, pp. 808–812.*
Lazar et al., Transforming Growth Factor x: Mutation of Aspartic Acid 47 and Leucine 48 Results in Different Biological Activities, Mar. 1988, Molecular and Cellular Biology, pp. 1247–1252.*
Burgess et al., Possible Dissociation of the Heparin–binding and Mitogenic Activities of Heparin–binding ( Acidic Fibroblast) Growth Factor–1 . . . , 1990, The Journal of Cell Biology, pp. 2129–2138.*
Bowie et al., Deiphering the Message in Protein Sequences: Tolerance to Amino Acid Substitutions, Mar. 16, Science, 1990, vol. 247, pp. 1306–1310.*
Smith et al. Nature. 1988. vol. 334: 724–726, 1988.*
Dwivedi et al. 1994. Plant Molecular Biology. 1994. vol. 26: 61–71, 1994.*
Bugos et al. Plant Molecular Biology. 1991. vol. 17: 1203–1215.*
McIntyre et al. Transgenic Research 5: 263–270, 1996.*
Ehlting, Jurgen et al., "Three 4–cournarate:coenzyme A ligases in *Arabidopsis thaliana* represent two evolutionarily divergent classes in angiosperms," *The Plant Journal*, vol. 19, No. 1, pp. 9–20 (1999).
Hu, Wen–Jing et al., "Compartmentalized expression of two structurally and functionally distinct 4–cournarate:CoA ligase genes in aspen (*Populus tremuloides*)," *Proc. Natl. Acad. Sci. USA*, vol. 95, No. 9, pp. 5407–5412 (Apr. 28, 1998).

(List continued on next page.)

*Primary Examiner*—Amy J. Nelson
*Assistant Examiner*—Stuart F. Baum
(74) *Attorney, Agent, or Firm*—Ann W. Sackman; Janet Sleath

(57) ABSTRACT

Novel isolated polynucleotides associated with the lignin biosynthetic pathway are provided, together with constructs including such sequences. Methods for the modulation of lignin content, lignin structure and lignin composition in target organisms are also disclosed, the methods comprising incorporating one or more of the polynucleotides of the present invention into the genome of a target organism.

27 Claims, 2 Drawing Sheets

OTHER PUBLICATIONS

Uhlmann, A, Ebel J., "Molecular cloing and expression of 4–cournarate:coenzyme A ligase, an enzyme involved in the resistance response of soybean (Glyrine max L.) against pathogen attack," *Plant Physiol.*, vol. 102, No. 4, pp. 1147–1156 (Aug. 1993).

Zhang, X.H., Chang, V.L., "Molecular cloing of 4–cournarate:coenzyme A ligase, in loblolly pine and the roles of this enzyme in the biosynthesis of lignin in compression wood," *Plant Physiol.*, vol. 113, No. 1, pp. 65–74 (Jan. 1997).

GenBank (no EST GSS HTG STS): Accession No. PTU12012 (Mar. 23, 1996).

PCT Written Opinion; In re Fletcher Challenge Forests, Ltd.; International Application No. PCT/NZ99/00168, filed Oct. 6, 1999.

Hu, Wen–Jing et al., "Repression of lignin biosynthesis promotes cellulose accumulation and growth in transgenic trees," *Nature Biotechnology*, vol. 17, No. 8, pp. 808–812 (Aug. 1999).

Neustaedter, David A. et al., "A novel parsley 4CL1 cis–element is required for developmentqally regulated expression and protein–DNA complex formation," *The Plant Journal*, vol. 18, No. 1, pp. 77–88 (Apr. 1999).

Lee, Diane et al., "Antisense Suppression of 4–Coumarate-:Coenzyme A Ligase Activity in Arabidopsis Leads to Altered Lignin Subunit Composition," *The Plant Cell*, vol. 9, No. 11, pp. 1985–1998 (Nov. 1997).

Kajita, Shinya et al., "Alterations in the Biosynthesis of Lignin in Transgenic Plants with Chimeric Genes for 4–Coumarate:Coenzyme A Ligase," *Plant Cell Physiol.* vol. 37, No. 7, pp. 957–965 (Oct. 1996).

Hauffe, Karl D. et al., "Combinatorial interactions between positive and negative cis–acting elements control spatial patterns of 4CL–1 expression in transgenic tobacco," *The Plant Journal*, vol. 4., No. 2, pp. 235–253 (Aug. 1993).

Hauffe, Karl D. et al., "A Parsley 4CL–1 Promoter Fragment Specifies Complex Expression Patterns in Transgenic Tobacco," *The Plant Cell*, vol. 3., No. 2, pp. 435–443 (May 1991).

In re Genesis Research & Development Corp. and Fletcher Challenge Forests Ltd; PCT International Search Report; Int'l No. PCT/NZ99/00168 filed Oct. 6, 1999 (7 sheets).

GenBank (no EST GSS HTG STS); Accession No. Z49263 (Sep. 25, 1997).

EMBL (no EST GSS HTG STS); Accession No. L07634 (Jan. 7, 1993).

GenBank (no EST GSS HTG STS); Accession No. X92437 (Jul. 17, 1998).

EMBL (no EST GSS HTG STS); Accession No. D87520 (Sep. 8, 1996).

EMBL (no EST GSS HTG STS); Accession No. U29243 (Jul. 9, 1995).

GenBank (no EST GSS HTG STS); Accession No. U12013 (Mar. 23, 1996).

GenBank (no EST GSS HTG STS); Accession No. U12012 (Mar. 23, 1996).

GenBank (no EST GSS HTG STS); Accession No. U39405 (Feb. 7, 1997).

GenBank (no EST GSS HTG STS); Accession No. U39404 (Feb. 7, 1997).

GenBank (no EST GSS HTG STS); Accession No. AF008183 (Feb. 26, 1998).

Swiss–Prot; Accession No. P14912 (Apr. 1, 1990).

Swiss–Prot; Accession No. P14913 (Apr. 1, 1990).

GenPept; Accession No. BAA07828 (Dec. 8, 1994).

GenPept; Accession No. AAB18638 (Mar. 7, 1996).

GenPept; Accession No. AAC39366 (Jun. 12, 1997).

GenPept; Accession No. AAB18638 (Mar. 7, 1996).

GenPept; Accession No. AAC39365 (Jun. 12, 1997).

GenBank (no EST GSS HTG STS); Accession No. U38416 (Aug. 12, 1996).

GenPept; Accession No. AAA62426 (1994).

Swiss–Prot; Accession No. P93711 (Jul. 15, 1998).

EMBL (no EST GSS HTG STS); Accession No. X52623 (Jul. 9, 1990).

GenBank (no EST GSS HTG STS); Accession No. L43362 (Jul. 7, 1995).

GenPept; Accession No. AAA92669 (Jul. 7, 1994).

GenPept; Accession No. AAB18637 (Mar. 7, 1996).

Swiss–Prot; Accession No. P13687 (Jul. 1, 1993).

PIR; Accession No. PQ0773 (Jul. 14, 1994).

In re Bloksberg, et al., Materials and Methods for the Modification of Plant Lignin Content, patent application No. 09/211,710; Filed Dec. 14, 1998; Allowed Claims.

Wagner, A. et al., "Direct Submission", *Genbank Sequence Database*, (Sep. 29, 1996).

Wagner, A. et al., "Isolation and Characterisation of a Cinnamyl–Alcohol Dehydrogenase Gene from Pinus Radiata", *Queenstown Molecular Biology Meeting*, New Zealand Forest Research Institute (Aug. 1996).

\* cited by examiner

SEQUENCE LISTING

<160> NUMBER OF SEQ ID NOS: 185

<210> SEQ ID NO 1
<211> LENGTH: 535
<212> TYPE: DNA
<213> ORGANISM: Eucalyptus grandis
<220> FEATURE:
<221> NAME/KEY: unsure
<222> LOCATION: (110)...(110)

<400> SEQUENCE: 1

```
cttcgcgcta ccgcatactc caccaccgcg tgcagaagat gagctcggag ggtgggaagg      60
aggattgcct cggttgggct gcccgggacc cttctgggtt cctctccccn tacaaattca     120
cccgcaggcc gtgggaagcg aagacgtctc gattaagatc acgcactgtg gagtgtgcta     180
cgcagatgtg gcttggacta ggaatgtgca gggacactcc aagtatcctc tggtgccggg     240
gcacgagata gttggaattg tgaaacaggt tggctccagt gtccaacgct tcaaagttgg     300
cgatcatgtg ggggtgggaa cttatgtcaa ttcatgcaga gagtgcgagt attgcaatga     360
caggctagaa gtccaatgtg aaaagtcggt tatgactttt gatggaattg atgcagatgg     420
tacagtgaca aagggaggat attctagtca cattgtcgtc catgaaaggt attgcgtcag     480
gattccagaa aactacccga tggatctagc agcgcattgc tctgtgctgg atcac          535
```

<210> SEQ ID NO 2
<211> LENGTH: 671
<212> TYPE: DNA
<213> ORGANISM: Pinus radiata

<400> SEQUENCE: 2

```
gcgcctgcag gtcgacacta gtggatccaa agaattcggc acgaggttgc aggtcgggga      60
tgatttgaat cacagaaacc tcagcgattt tgccaagaaa tatggcaaaa tctttctgct     120
caagatgggc cagaggaatc ttgtggtagt ttcatctccc gatctcgcca aggaggtcct     180
gcacacccag ggcgtcgagt ttgggtctcg aacccggaac gtggtgttcg atatcttcac     240
gggcaagggg caggacatgg tgttcaccgt ctatggagat cactggagaa agatgcgcag     300
gatcatgact gtgcctttct ttacgaataa agttgtccag cactacagat tcgcgtggga     360
agacgagatc agccgcgtgg tcgcggatgt gaaatcccgc gccgagtctt ccacctcggg     420
cattgtcatc cgtagcgcct ccagctcatg atgtataata ttatgtatag gatgatgttc     480
gacaggagat tcgaatccga ggacgacccg cttttcctca agctcaaggc cctcaacgga     540
gagcgaagtc gattggccca gagctttgag tacaattatg gggatttcat tcccagtctt     600
aggcccttcc tcagaggtta tcacagaatc tgcaatgaga ttaaagagaa acggctctct     660
cttttcaagg a                                                          671
```

<210> SEQ ID NO 3
<211> LENGTH: 940
<212> TYPE: DNA
<213> ORGANISM: Pinus radiata
<220> FEATURE:
<221> NAME/KEY: unsure
<222> LOCATION: (463)...(463)

<400> SEQUENCE: 3

```
cttcaggaca agggagagat caatgaggat aatgttttgt acatcgttga gaacatcaac      60
gttgcagcaa ttgagacaac gctgtggtcg atggaatggg aatagcgga gctggtgaac      120
```

-continued

```
caccaggaca ttcagagcaa ggtgcgcgca gagctggacg ctgttcttgg accaggcgtg      180
cagataacgg aaccagacac gacaaggttg ccctaccttc aggcggttgt gaaggaaacc      240
cttcgtctcc gcatggcgat cccgttgctc gtcccccaca tgaatctcca cgacgccaag      300
ctcgggggct acgatattcc ggcagagagc aagatcctgg tgaacgcctg gtggttggcc      360
aacaaccccg ccaactggaa gaaccccgag gagttccgcc ccgagcggtt cttcgaggag      420
gagaagcaca ccgaagccaa tgcaacgac ttcaaattcc tgnccttcgg tgtggggagg       480
aggagctgcc cgggaatcat tctggcgctg ctctcctcgc actctccatc ggaagacttg      540
ttcagaactt ccaccttctg ccgccgcccg ggcagagcaa agtggatgtc actgagaagg      600
gcgggcaatt cagccttcac attctcaacc attctctcat cgtcgccaag cccatagctt      660
ctgcttaatc ccaacttgtc agtgactggt atataaatgc gcgcacctga caaaaaaca       720 ctccatctat catgactgtg tgtgcgtgtc cactgtcgag tctactaaga gctcatagca      780
cttcaaaagt ttgctaggat ttcaataaca gacaccgtca attatgtcat gtttcaataa      840
aagtttgcat aaattaaatg atatttcaat atactatttt gactctccac caattgggga      900
attttactgc taaaaaaaaa aaaaaaaaa aaaaaaaaa                              940
```

<210> SEQ ID NO 4
<211> LENGTH: 949
<212> TYPE: DNA
<213> ORGANISM: Pinus radiata
<220> FEATURE:
<221> NAME/KEY: unsure
<222> LOCATION: (1)...(949)
<223> OTHER INFORMATION: n at all occurrences indicates unsure

<400> SEQUENCE: 4

```
nngctcnacc gacggtggac ggtccgctac tcagtaactg agtgggatcc cccgggctga      60
caggcaattc gatttagctc actcattagg cacccagac tttacacttt atgcttccgg       120
ctcgtatgtt gtgtggaatt gtgagcggat aacaatttca cacaggaaac agctatgacc      180
atgattacgc caagcgcgca attaaccctc actaaaggga acaaaagctg gagctccacc      240
gcggtggcgg ccgctctaga actagtggat ccaaagaatt cggcacgaga cccagtgacc      300
ttcaggcctg agagatttct tgaggaagat gttgatatta agggccatga ttacaggcta      360
ctgccattgg tgcagggcgc aggatctgcc ctggtgcaca attgggtatt aatttagttc      420
agtctatgtt gggacacctg cttcatcatt tcgtatgggc acctcctgag ggaatgaagg      480
cagaagacat agatctcaca gagaatccag ggcttgttac tttcatggcc aagcctgtgc      540
aggccattgc tattcctcga ttgcctgatc atctctacaa gcgacagcca ctcaattgat      600
caattgatct gatagtaagt ttgaattttg ttttgataca aaacgaaata acgtgcagtt      660
tctccttttc catagtcaac atgcagcttt ctttctctga agcgcatgca gctttctttc      720
tctgaagccc aacttctagc aagcaataac tgtatatttt agaacaaata cctattcctc      780
aaattgagwa tttctctgta ggggnngnta attgtgcaat ttgcaagnaa tagtaaagtt      840
tantttaggg nattttaata gtcctangta anangnggna atgntagngg gcattnagaa      900
anccctaata gntgttggng gnngntaggn ttttnacca aaaaaaaaa                   949
```

<210> SEQ ID NO 5
<211> LENGTH: 959
<212> TYPE: DNA
<213> ORGANISM: Pinus radiata
<220> FEATURE:

<221> NAME/KEY: unsure
<222> LOCATION: (697)...(697)

<400> SEQUENCE: 5

```
gaattcggca cgagaaagcc ctagaatttt ttcagcatgc tatcacagcc ccagcgacaa      60
ctttaactgc aataactgtg gaagcgtaca aaaagtttgt cctagtttct ctcattcaga     120
ctggtcaggt tccagcattt ccaaaataca cacctgctgt tgtccaaaga aatttgaaat     180
cttgcactca gccctacatt gatttagcaa acaactacag tagtgggaaa atttctgtat     240
tggaagcttg tgtcaacacg aacacagaga agttcaagaa tgatagtaat ttggggttag     300
tcaagcaagt tttgtcatct ctttataaac ggaatattca gagattgaca cagacatatc     360
tgaccctctc tcttcaagac atagcaagta cggtacagtt ggagactgct aagcaggctg     420
aactccatgt tctgcagatg attcaagatg gtgagatttt tgcaaccata aatcagaaag     480
atgggatggt gagcttcaat gaggatcctg aacagtacaa acatgtcag atgactgaat      540
atatagatac tgcaattcgg agaatcatgg cactatcaaa gaagctcacc acagtagatg     600
agcagatttc gtgtgatcat tcctacctga gtaaggtggg gagagagcgt tcaagatttg     660
acatagatga ttttgatact gttccccaga agttcanaaa tatgtaacaa atgatgtaaa     720
tcatcttcaa gactcgctta tattcattac tttctatgtg aattgatagt ctgttaacaa     780
tagtactgtg gctgagtcca gaaaggatct ctcggtatta tcacttgaca tgccatcaaa     840
aaaatctcaa atttctcgat gtctagtctt gattttgatt atgaatgcga cttttagttg     900
tgacatttga gcacctcgag tgaactacaa agttgcatgt taaaaaaaaa aaaaaaaaa      959
```

<210> SEQ ID NO 6
<211> LENGTH: 1026
<212> TYPE: DNA
<213> ORGANISM: Pinus radiata

<400> SEQUENCE: 6

```
gaattcggca cgagctttga ggcaacctac attcattgaa tcccaggatt tcttcttgtc      60
caaacaggtt taaggaaatg gcaggcacaa gtgttgctgc agcagaggtg aaggctcaga     120
caacccaagc agaggagccg gttaaggttg tccgccatca agaagtggga cacaaaagtc     180
ttttgcagag cgatgccctc tatcagtata tattggaaac gagcgtgtac cctcgtgagc     240
ccgagccaat gaaggagctc cgcgaagtga ctgccaagca tccctggaac ctcatgacta     300
cttctgccga tgagggtcaa tttctgggcc tcctgctgaa gctcattaac gccaagaaca     360
ccatggagat tgggtgtac actggttact cgcttctcag cacagccctt gcattgcccg     420
atgatggaaa gattctagcc atggacatca acagagagaa ctatgatatc ggattgccta     480
ttattgagaa agcaggagtt gcccacaaga ttgacttcag agagggccct gctctgccag     540
ttctggacga actgcttaag aatgaggaca tgcatggatc gttcgatttt gtgttcgtgg     600
atgcggacaa agacaactat ctaaactacc acaagcgtct gatcgatctg gtgaaggttg     660
gaggtctgat tgcatatgac aacacccgt ggaacgatc tgtggtggct ccacccgatg      720
ctcccctgag gaaatatgtg agatattaca gagatttcgt gatggagcta acaaggccc      780
ttgctgtcga tccccgcatt gagatcagcc aaatcccagt cggtgacggc gtcaccctt      840
gcaggcgtgt ctattgaaaa caatccttgt ttctgctcgt ctattgcaag cataaaggct     900
ctctgattat aaggagaacg ctataatata tggggttgaa gccatttgtt ttgtttagtg     960
tattgataat aaagtagtac agcatatgca agtttgtat caaaaaaaaa aaaaaaaaa     1020
``` aaaaaa 1026

<210> SEQ ID NO 7
<211> LENGTH: 1454
<212> TYPE: DNA
<213> ORGANISM: Pinus radiata

<400> SEQUENCE: 7

| gaattcggca | cgaggccaac | tgcaagcaat | acagtacaag | agccagacga | tcgaatcctg | 60 |
| tgaagtggtt | ctgaagtgat | gggaagcttg | gaatctgaaa | aaactgttac | aggatatgca | 120 |
| gctcgggact | ccagtggcca | cttgtcccct | tacacttaca | atctcagaaa | gaaaggacct | 180 |
| gaggatgtaa | ttgtaaaggt | catttactgc | ggaatctgcc | actctgattt | agttcaaatg | 240 |
| cgtaatgaaa | tggacatgtc | tcattaccca | atggtccctg | gcatgaagt | ggtggggatt | 300 |
| gtaacagaga | ttggcagcga | ggtgaagaaa | ttcaaagtgg | gagagcatgt | aggggttggt | 360 |
| tgcattgttg | ggtcctgtcg | cagttgcggt | aattgcaatc | agagcatgga | acaatactgc | 420 |
| agcaagagga | tttggaccta | caatgatgtg | aaccatgacg | gcacacctac | tcagggcgga | 480 |
| tttgcaagca | gtatggtggt | tgatcagatg | twtgtggttc | gaatcccgga | gaatcttcct | 540 |
| ctggaacaag | cggcccctct | gttatgtgca | ggggttacag | ttttcagccc | aatgaagcat | 600 |
| tcgccatga | cagagcccgg | gaagaaatgt | gggattttgg | gtttaggagg | cgtggggcac | 660 |
| atgggtgtca | agattgccaa | agcctttgga | ctccacgtga | cggttatcag | ttcgtctgat | 720 |
| aaaaagaaag | aagaagccat | ggaagtcctc | ggcgccgatg | cttatcttgt | tagcaaggat | 780 |
| actgaaaaga | tgatggaagc | agcagagagc | ctagattaca | taatgacac | cattccagtt | 840 |
| gctcatcctc | tggaaccata | tcttgccctt | ctgaagacaa | atggaaagct | agtgatgctg | 900 |
| ggcgttgttc | cagagtcgtt | gcacttcgtg | actcctctct | taatacttgg | gagaaggagc | 960 |
| atagctggaa | gtttcattgg | cagcatggag | gaaacacagg | aaactctaga | tttctgtgca | 1020 |
| gagaagaagg | tatcatcgat | gattgaggtt | gtgggcctgg | actacatcaa | cacggccatg | 1080 |
| gaaaggttgg | agaagaacga | tgtccgttac | agatttgtgg | tggatgttgc | tagaagcaag | 1140 |
| ttggataatt | agtctgcaat | caatcaatca | gatcaatgcc | tgcatgcaag | atgaatagat | 1200 |
| ctggactagt | agcttaacat | gaaagggaaa | ttaaattttt | atttaggaac | tcgatactgg | 1260 |
| tttttgttac | tttagtttag | cttttgtgag | gttgaaacaa | ttcagatgtt | tttttaactt | 1320 |
| gtatatgtaa | agatcaattt | ctcgtgacag | taaataataa | tccaatgtct | tctgccaaat | 1380 |
| taatatatgt | attcgtattt | ttatatgaaa | aaaaaaaaa | aaaaaaaaa | aaaaaaaaa | 1440 |
| aaaaaaaaaa | aaaa | | | | | 1454 |

<210> SEQ ID NO 8
<211> LENGTH: 740
<212> TYPE: DNA
<213> ORGANISM: Pinus radiata

<400> SEQUENCE: 8

| gaattcggca | cgagaccatt | tccagctaat | attggcatag | caattggtca | ttctatcttt | 60 |
| gtcaaaggag | atcaaacaaa | ttttgaaatt | ggacctaatg | gtgtggaggc | tagtcagcta | 120 |
| tacccagatg | tgaaatatac | cactgtcgat | gagtacctca | gcaaatttgt | gtgaagtatg | 180 |
| cgagattctc | ttccacatgc | ttcagagata | cataacagtt | tcaatcaatg | tttgtcctag | 240 |
| gcatttgcca | aattgtgggt | tataatcctt | cgtaggtgtt | tggcagaaca | gaacctcctg | 300 |
| tttagtatag | tatgacgagc | taggcactgc | agatccttca | cactttctc | ttccataaga | 360 |

```
aacaaatact cacctgtggt ttgttttctt tctttctgga actttggtat ggcaataatg    420
tctttggaaa ccgcttagtg tggaatgcta agtactagtg tccagagttc taagggagtt    480
ccaaaatcat ggctgatgtg aactggttgt tccagagggt gtttacaacc aacagttgtt    540
cagtgaataa ttttgttaga gtgtttagat ccatctttac aaggctattg agtaaggttg    600
gtgttagtga acggaatgat gtcaaatctt gatgggctga ctgactctct tgtgatgtca    660
aatcttgatg gattgtgtct tttcaatgg taaaaaaaaa aaaaaaaaaa aaaaaaaaa    720 aaaaaaaaaa aaaaaaaaaa                                                740

<210> SEQ ID NO 9
<211> LENGTH: 624
<212> TYPE: DNA
<213> ORGANISM: Pinus radiata

<400> SEQUENCE: 9
gaattcctgc agcccggggg atccactagt tctagagcgg ccgccaccgc ggtggagctc     60
gcgcgcctgc aggtcgacac tagtggatcc aaagaattcg cacgaggcc cgacggccac    120 ttgttggacg ccatggaagc tctccggaaa gccgggattc tggaaccgtt taaactgcag    180
cccaaggaag gactggctct cgtcaacggc acagcgtgg gatccgccgt ggccgcgtcc    240
gtctgtgttg acgccaacgt gctgggcgtg ctggctgaga ttctgtctgc gctcttctgc    300
gaggtgatgc aagggaaacc ggagttcgta gatccgttaa cccaccagtt gaagcaccac    360
ccagggcaga tcgaagccgc ggccgtcatg gagttcctcc tcgacggtag cgactacgtg    420
aaagaagcag cgcggcttca cgagaaagac ccgttgagca aaccgaaaca agaccgctac    480
gctctgcgaa catcgccaca gtggttgggg cctccgatcg aagtcatccg cgctgcyact    540
cactccatcg agcgggagat caattccgtc aacgacaatc cgttaatcga tgtctccagg    600
gacatggctg tccacggcgg caac                                           624

<210> SEQ ID NO 10
<211> LENGTH: 278
<212> TYPE: DNA
<213> ORGANISM: Pinus radiata

<400> SEQUENCE: 10
gaattcctgc agcccggggg atccactagt tctagagcgg ccgccaccgc ggtggagctc     60
cagtacctgg ccaaccccgt cacgactcac gtccagagcg ccgaacaaca caaccaggat    120
gtcaattccc tcggcttgat ctccgccaga aagactgccg aggccgttga gattttaaag    180
ctgatgttcg ctacatatct ggtggcctta tgccaggcga tcgatctccg gcacctggaa    240
gaaaacatgc gatccgttgt gaagcacgta gtcttgca                            278

<210> SEQ ID NO 11
<211> LENGTH: 765
<212> TYPE: DNA
<213> ORGANISM: Pinus radiata

<400> SEQUENCE: 11
gagctcctgc aagtcatcga tcatcagccc gttttctcgt acatcgacga tcccacaaat     60
ccatcatacg cgcttatgct ccaactcaga gaagtgctcg tagatgaggc tctcaaatca    120
tcttgcccag acgggaatga cgaatccgat cacaatttgc agcccgctga gagcgctgga    180
gctgctggaa tattacccaa ttgggtgttt agcaggatcc ccatatttca agaggagttg    240
```

-continued

| | |
|---|---|
| aaggcccgtt tagaggaaga ggttccgaag gcgagggaac gattcgataa tgggacttc | 300 |
| ccaattgcaa acagaataaa caagtgcagg acatatccca tttacagatt cgtgagatca | 360 |
| gagttgggaa ccgatttgct aacagggccc aagtggagaa gccccggcga agatatagaa | 420 |
| aaggtatttg agggcatttg ccaagggaaa attggaaacg tgatcctcaa atgtctggac | 480 |
| gcttggggtg ggtgcgctgg accattcact ccacgtgcat atcctgcgtc tcctgcagcg | 540 |
| ttcaatgcct catattgggc atggtttgat agcaccaaat caccctctgc aacgagcggc | 600 |
| agaggtttct ggagcgccca acaacaacaa gttctttgat ttaactgact cttaagcatt | 660 |
| cctaaacagc ttgttcttcg caataacgaa tctttcatct tcgttacttt gtaaaagatg | 720 |
| gggttccaac aaaatagaag aaatattttc gatccaaaaa aaaaa | 765 |

<210> SEQ ID NO 12
<211> LENGTH: 453
<212> TYPE: DNA
<213> ORGANISM: Pinus radiata

<400> SEQUENCE: 12

| | |
|---|---|
| tgattatgcg gatccttggg cagggatacg gcatgacaga agcaggcccg gtgctggcaa | 60 |
| tgaacctagc cttcgcaaag aatcctttcc ccgccaaatc tggctcctgc ggaacagtcg | 120 |
| tccggaacgc tcaaataaag atcctcgatt acaggaactg gcgagtctct cccgcacaat | 180 |
| caagccggcg aaatctgcat ccgcggaccc gaaataatga aggatatat taacgacccg | 240 |
| gaatccacgg ccgctacaat cgatgaagaa ggctggctcc acacaggcga cgtcgggtac | 300 |
| attgacgatg acgaagaaat cttcatagtc gacagagtaa aggagattat caatataaag | 360 |
| gcttccaggt ggatcctgct aatcgaattc ctgcagcccg ggggtccact agttctagag | 420 |
| cggccgccac cgcggtggag ctccagcttt tgt | 453 |

<210> SEQ ID NO 13
<211> LENGTH: 278
<212> TYPE: DNA
<213> ORGANISM: Pinus radiata

<400> SEQUENCE: 13

| | |
|---|---|
| tcttcgaatt ctcttcacg actgcttcgt taatggctgc gatggctcga tattgttaga | 60 |
| tgataactca acgttcaccg gagaaaagac tgcaggccca atgttaatt ctgcgagagg | 120 |
| attcgacgta atagacacca tcaaaactca agttgaggca gcctgcagtg gtgtcgtgtc | 180 |
| agttgccgac attctcgcca ttgctgcacg cgattcagtc gtccaactgg ggggcccaac | 240 |
| atggacggta cttctgggag aaaagacgga tccgatca | 278 |

<210> SEQ ID NO 14
<211> LENGTH: 23
<212> TYPE: DNA
<213> ORGANISM: Pinus radiata

<400> SEQUENCE: 14

| | |
|---|---|
| cttcgaattc wyttycayga ytg | 23 |

<210> SEQ ID NO 15
<211> LENGTH: 22
<212> TYPE: DNA
<213> ORGANISM: Pinus radiata

<400> SEQUENCE: 15

| | |
|---|---|
| gatcggatcc rtcyykycty cc | 22 |

<210> SEQ ID NO 16
<211> LENGTH: 472
<212> TYPE: DNA
<213> ORGANISM: Eucalyptus grandis

<400> SEQUENCE: 16

| | | | | | |
|---|---|---|---|---|---|
| aattcggcac | gagacgacct | cttgtatcgg | acccggatcc | gctatcgtta | acgtacacac | 60 |
| gttctagtgc | tgaatggaga | tggagagcac | caccggcacc | ggcaacggcc | ttcacagcct | 120 |
| ctgcgccgcc | gggagccacc | atgccgaccc | actgaactgg | ggggcggcgg | cagcagcct | 180 |
| cacagggagc | cacctcgacg | aggtgaagcg | gatggtcgag | gagtaccgga | ggccggcggt | 240 |
| gcgcctcggc | ggggagtccc | tcacgatagc | ccaggtggcg | gcggtggcga | gtcaggaggg | 300 |
| ggtaggggtc | gagctctcgg | aggcggcccg | tcccagggtc | aaggccagca | gcgactgggt | 360 |
| catggagagc | atgaacaagg | gaactgacag | ctacggggtc | accaccgggt | tcggcggcaa | 420 |
| cttctcaaac | cggaggccga | agcaaggcgg | tccttttcag | aaggaactta | ta | 472 |

<210> SEQ ID NO 17
<211> LENGTH: 622
<212> TYPE: DNA
<213> ORGANISM: Eucalyptus grandis

<400> SEQUENCE: 17

| | | | | | |
|---|---|---|---|---|---|
| ccaaagctcc | tagtgcctca | tgagtctgct | gaggattgca | caattggcgg | gttcgacgtg | 60 |
| ccccgaggca | ccatgatcct | ggttaatgcg | tgggcaattc | aaagagaccc | aaaagtgtgg | 120 |
| gacgatccca | caaattttaa | accggagagg | tacgagggat | tggaaggtga | tcatgcctac | 180 |
| cgactattgc | cgtttgggat | ggggaggaga | agttgtcctg | gtgctggcct | tgccaataga | 240 |
| gtggtgagct | tggtcctggc | ggcgcttatt | cagtgcttcg | aatgggaacg | agttggcgaa | 300 |
| gaattggtgg | acttgtccga | ggggacggga | ctcacaatgc | caaagagaga | gccattggag | 360 |
| gccttgtgca | aagcgcgtga | atgcatgata | gctaatgttc | ttgcgcacct | ttaagaaggt | 420 |
| cgttgtctaa | tgaatttaca | ttggtgatgt | atctccaatg | ttttttgaata | atcaaataga | 480 |
| ctgaaaatag | gccagtgcag | ctttaggaat | gatcgtgagc | atcaatagca | tcctgaggag | 540 |
| gccaatgcag | ctttaggcct | ttctcttagg | agaaaaatga | tggtttatat | aggtactggc | 600 |
| aacattgttc | aaaaaaaaaa | aa | | | | 622 |

<210> SEQ ID NO 18
<211> LENGTH: 414
<212> TYPE: DNA
<213> ORGANISM: Eucalyptus grandis

<400> SEQUENCE: 18

| | | | | | |
|---|---|---|---|---|---|
| cacgctcgac | gaattcggta | ccccgggttc | gaaatcgata | agcttggatc | caaagcaaca | 60 |
| cattgaactc | tctctctctc | tctctctctc | tctctctctc | tcccccaccc | cccttccca | 120 |
| accccaccca | catacagaca | agtagatacg | cgcacacaga | agaagaaaag | atgggggttt | 180 |
| caatgcagtc | aatcgcacta | gcgacggttc | tggccgtcct | aacgacatgg | gcgtggaggg | 240 |
| cggtgaactg | ggtgtggctg | aggccgaaga | ggctcgagag | gcttctgaga | cagcaaggtc | 300 |
| tctccggcaa | gtcctacacc | ttcctggtcg | gcgacctcaa | ggagaacctg | cggatgctca | 360 |
| aggaagccaa | gtccaagccc | atcgccgtct | ccgatgacat | caagcctcgt | ctct | 414 |

<210> SEQ ID NO 19

<211> LENGTH: 469
<212> TYPE: DNA
<213> ORGANISM: Eucalyptus grandis

<400> SEQUENCE: 19

```
gaattcggca cgagtgtctc tctctctctc tctctctgta aaccaccatg ctcttcctca      60
ctcatctcct agcagttcta ggggttgtgt tgctcctgct aattctatgg agggcaagat     120
cttctccgaa caaacccaaa ggtactgcct taccccggga gctgccgggc gcatggccga     180
tcataggcca catccacttg ctgggcggcg agacccgct ggccaggacc ctggccgcca      240
tggcggacaa gcagggcccg atgtttcgga tccgtctcgg agtccacccg gcgaccatca     300
taagcagccg tgaggcggtc cgggagtgct tcaccaccca cgacaaggac ctcgcttctc     360
gccccaaatc caaggcggga atccacttgg ctacgggta tgccggtttt ggcttcgtag      420
aatacgggga cttttggcgc gagatgagga agatcaccat gctcgagct                 469
```

<210> SEQ ID NO 20
<211> LENGTH: 341
<212> TYPE: DNA
<213> ORGANISM: Eucalyptus grandis

<400> SEQUENCE: 20

```
cgggctcgtg gctcggctcc ggcgcaacgc ccttcccacc gggcccgagg ggcctcccgg      60
tcatcgggaa catgctcatg atgggcgagc tcacccaccg cggcctcgcg agtctggcga     120
agaagtatgg cgggatcttc cacctccgca tgggcttcct gcacatggtt gccgtgtcgt     180
cccccgacgt ggcccgccag gtcctccagg tccacgacgg gatcttctcg aaccggcctg     240
ccaccatcgc gatcagctac ctcacgtatg accgggccga catggccttc gcgcactacg     300
gcccgttctg gcggcagatg cggaagctgt gcgtgatgaa a                         341
```

<210> SEQ ID NO 21
<211> LENGTH: 387
<212> TYPE: DNA
<213> ORGANISM: Eucalyptus grandis

<400> SEQUENCE: 21

```
gaattcggca cgagcgggct cgtggctcgg ctccggcgca acgcccttcc caccgggccc      60
gagggcctc ccggtcatcg ggaacatgct catgatgggc gagctcaccc accgcggcct     120
cgcgagtctg gcgaagaagt atggcgggat cttccacctc cgcatgggct tcctgcacat     180
ggttgccgtg tcgtccccg acgtggcccg ccaggtcctc caggtccacg acgggatctt      240
ctcgaaccgg cctgccacca tcgcgatcag ctacctcacg tatgaccggg ccgacatggc     300
cttcgcgcac tacggcccgt tctggcggca gatgcggaag ctgtgcgtga tgaaagctct     360
tcagcggaag cgggctgagt cgtggga                                         387
```

<210> SEQ ID NO 22
<211> LENGTH: 443
<212> TYPE: DNA
<213> ORGANISM: Eucalyptus grandis

<400> SEQUENCE: 22

```
cacgagctcg tgagccttcc cggagacaag gccatcttac ttcgcaacaa attgcgtccg      60
cactcctttc tcaagaaacc tagtcatcca agaagcagag cattgcaact gcaaacagcc     120
aaagcccaaa ctcgtacaga aggagagaga gagagagaat agaagcatga gtgcatgcac     180
gaaccaagca atcacgacgg ccagtgaaga tgaagagttc ttgttcgcca tggaaatgaa     240
```

-continued

```
tgctctgata gcactcccct tggtcttgaa ggccaccatc gaactgggga tcctcgaaat    300
actggccgag tgcgggccta tgctccact  ttcgcctgct cagattgcct cccgtctctc    360
cgcaaagaac ccggaagccc cgtaaccct  tgaccggatc ctccggtttc tcgccagcta    420
ctccatcctc tcttgcactc tcg                                            443
```

<210> SEQ ID NO 23
<211> LENGTH: 607
<212> TYPE: DNA
<213> ORGANISM: Eucalyptus grandis

<400> SEQUENCE: 23

```
gaattcggca cgagccaacc ctggaccagg tacttttggc aggcggtcca ttgcccttca     60
aaccggtcca aaccggacca tcactgtcct tatatacgtt gcatcatgcc tgctcataga    120
acttaggtca actgcaacat ttcttgatca caacatatta caatattcct aagcagagag    180
agagagagag agagagagag agagagagag agtttgaa  tcaatggcca ccgccggaga    240
ggagagccaa cccaagccg  ggaggcacca ggaggttggc cacaagtctc tccttcagag    300
tgatgctctt taccaatata ttttggagac cagcgtgtac ccaagagagc ctgagcccat    360
gaaggagctc aggaaataa  cagcaaaaca tccatggaac ataatgacaa catcagcaga    420
cgaagggcag ttcttgaaca tgcttctcaa gctcatcaaa gccaagaaca ccatggagat    480
tggtgtcttc actggctact ctctcctcgc caccgctctt gctcttcctg atgacgaaa     540 gattttggct atggacatta acagagagag ctatgaactt ggcctgccgg catccaaaaa    600
gccggtg                                                              607
```

<210> SEQ ID NO 24
<211> LENGTH: 421
<212> TYPE: DNA
<213> ORGANISM: Eucalyptus grandis

<400> SEQUENCE: 24

```
gaattcggca cgagccgttt tatttcctct gatttccttt gctcgagtct cgcggaagag     60
agagaagaga ggagaggaga gaatgggttc gaccggatcc gagacccaga tgaccccgac    120
ccaagtctcg gacgaggagg cgaacctctt cgccatgcag ctggcgagcg cctccgtgct    180
ccccatggtc ctcaaggccg ccatcgagct cgacctcctc gagatcatgg ccaaggccgg    240
gccgggcgcg ttcctctccc cgggggaagt cgcggcccag ctcccgaccc agaaccccga    300
ggcacccgta atgctcgacc ggatcttccg gctgctggcc agctactccg tgctcacgtg    360
caccctccgc gacctccccg atggcaaggt cgagcggctc tacggcttag cgccggtgtg    420
c                                                                    421
```

<210> SEQ ID NO 25
<211> LENGTH: 760
<212> TYPE: DNA
<213> ORGANISM: Eucalyptus grandis

<400> SEQUENCE: 25

```
ggaagaagcc gagcaaacga attgcagacg ccattgaaaa aagacacgaa agagatcaag     60
aaggagctta gaagcatca  tcaatggcag ccaacgcaga gcctcagcag acccaaccag    120
cgaagcattc ggaagtcggc cacaagagcc tcttgcagag cgatgctctc taccagtata    180
tattggagac cagcgtctac ccaagagagc cagagcccat gaaggagctc aggaaataa    240
```

-continued

```
cagccaaaca tccatggaac ctgatgacca catcggcgga tgaagggcag ttcctgaaca      300
tgctcctcaa gctcatcaac gccaagaaca ccatggagat cggcgtctac accggctact      360
ctctcctcgc aaccgccctt gctcttcccg atgacgaaaa gatcttggcc atggccatca      420 ataggagaa cttcgagatc gggctgcccg tcatccagaa ggccggcctt gcccacaaga       480
tcgatttcag agaaggccct gccctgccgc tccttgatca gctcgtgcaa gatgagaaga      540
accatggaac gtacgacttc ttctcaatcc ttaatcgttc atttgaatac aaatacatgc      600
tcaatggttc aaagacaaca taagacagaa gatggaaaaa atagaaagga aggaaagtat      660
taagggtagt ttctcatttc atcaatgctt gattttgaga tctcctttct ggtgcgatca      720
gctgacccgg cggcacaggt gatgccatcc ccgacgggaa                            760
```

<210> SEQ ID NO 26
<211> LENGTH: 508
<212> TYPE: DNA
<213> ORGANISM: Eucalyptus grandis

<400> SEQUENCE: 26

```
gaattcggta cccgggttcg aaatcgataa gcttggatcc aaagaattcg gcacgagatc      60
actaaccatc tgcctttctt catcttcttt cttctgcttc tcctccgttt cctcgtttcg      120
atatcgtgaa aggagtccgt cgacgacaat ggccgagaag agcaaggtcc tgatcatcgg      180
agggacgggc tacgtcggca agttcatcgt ggaagcgagt gcaaaagcag gcatcccac      240 gttcgcgctg gttaggcaga gcacggtctc cgaccccgtc aagggccagc tcgtcgagag      300
cttcaagaac ttgggcgtca ctctgctcat cggtgatctg tacgatcatg agagcttggt      360
gaaggcaatc aagcaagccg acgtggtgat atcgacagtg gggcacatgc aaatggcgga      420
tcagaccaaa gaatcgtcga cgccattaaa ggaagctggc aacgttaagg tttgttggtt      480
ggttcatttg atctggtttg ggggggtc                                          508
```

<210> SEQ ID NO 27
<211> LENGTH: 495
<212> TYPE: DNA
<213> ORGANISM: Eucalyptus grandis

<400> SEQUENCE: 27

```
gaattcggca cgaggttaat ggcagtgcag cctcaacacc acccaccttc ctccatctct      60 ctcctcccctt cttctttctc tgacttcaat ggcagccgac tccatgcttg cgttcagtat      120
aagaggaagg tggggcagcc taaggggca ctgcgggtca ctgcatcaag caataagaag      180
atcctcatca tgggaggcac ccgtttcatc ggtgtgtttt tgtcgagact acttgtcaaa      240
gaaggtcatc aggtcacttt gtttaccaga ggaaaagcac ccatcactca acaattgcct      300
ggtgagtcgg acaaggactt cgctgatttt tcatccaaga tcctgcattt gaaaggagac      360
agaaaggatt ttgattttgt taaatctagt cttgctgcag aaggctttga cgttgtttat      420
gacattaacg gcgagaggcg gatgaagtcg caccaatttt ggatgcctgc caaaccttga      480
accagtcaac tactg                                                        495
```

<210> SEQ ID NO 28
<211> LENGTH: 472
<212> TYPE: DNA
<213> ORGANISM: Eucalyptus grandis

<400> SEQUENCE: 28

```
gaattcggca cgagcataag ctctcccgta atcctcacat cacatggcga agagcaaggt      60
```

```
cctcgtcgtt ggcggcactg gctacctcgg gcggaggttc gtgagggcga gcctggacca    120
gggccacccc acgtacgtcc tccagcgtcc ggagaccggc ctcgacattg agaagctcca    180
gacgctactg cgcttcaaga ggcgtggcgc ccaactcgtc gaggcctcgt tctcagacct    240
gaggagcctc gtcgacgctg tgaggcgggt cgatgtcgtc gtctgtgcca tgtcggggt     300 ccacttccgg agccacaaca tcctgatgca gctcaagctc gtgaggcta tcaaagaagc     360 tggaaatgtc aagcggtttt tgccgtcaga gttcggaatg acccggccc tcatgggtca     420 tgcaattgag ccgggaaggg tcacgttcga tgagaaatgg aggtgagaaa ag            472

<210> SEQ ID NO 29
<211> LENGTH: 396
<212> TYPE: DNA
<213> ORGANISM: Eucalyptus grandis

<400> SEQUENCE: 29
gaattcggca cgaggaggca cctcctcgaa acgaagaaga agaaggacga aggacgaagg    60
agacgaaggc gagaatgagc gcggcgggcg gtgccgggaa ggtcgtgtgc gtgaccgggg    120
cgtccggtta catcgcctcg tggctcgtca agctcctcct ccagcgcggc tacaccgtca    180
aggccaccgt ccgcgatccg aatgatccaa aaaagactga acatttgctt ggacttgatg    240
gagcgaaaga tagacttcaa ctgttcaaag caaacctgct ggaagagggt tcatttgatc    300
ctattgttga ggggttgtgca ggcgtttttc aaactgcctc tccctttttat catgatgtca    360 aggatccgca ggcagaatta cttgatccgg ctgtaa                              396

<210> SEQ ID NO 30
<211> LENGTH: 592
<212> TYPE: DNA
<213> ORGANISM: Eucalyptus grandis

<400> SEQUENCE: 30
gaattcggca cgaggttgaa cctcccgtcc tcggctctgc tcggctcgtc accctcttcg    60
cgctcccgca tactccacca ccgcgtacag aagatgagct cggagggtgg aaggaggat    120 tgcctcggtt gggctgcccg ggacccttct gggttcctct ccccctacaa attcacccgc    180
agggccgtgg gaagcgaaga cgtctcgatt aagatcacgc actgtggagt gtgctacgca    240
gatgtggctt ggactaggaa tgtgcaggga cactccaagt atcctctggt gccagggcac    300
gagatagttg gaattgtgaa acaggttggc tccagtgtcc aacgcttcaa agttggcgat    360
catgtggggg tgggaactta tgtcaattca tgcagagagt gcgagtattg caatgacagg    420
ctagaagtcc aatgtgaaaa gtcggttatg acttttgatg gaattgatgc agatggtaca    480
gtgacaaagg gaggatattc tagtcacatt gtcgtccatg aaaggtattg cgtcaggatt    540
ccagaaaact acccgatgga tctagcagcg catttgctct gtgctggatc ac            592

<210> SEQ ID NO 31
<211> LENGTH: 468
<212> TYPE: DNA
<213> ORGANISM: Eucalyptus grandis

<400> SEQUENCE: 31
gaattcggca cgagaactca tcttgaaatg tcattggagt catcatcctc tagtgagaag    60
aaacaaatgg gttccgccgg attcgaatcg gccacaaagc cgcacgccgt ttgcattccc    120
taccctgcac aaagccacat tggcgccatg ctcaagctag caaagctcct ccatcacaag    180
```

-continued

```
ggcttccaca tctccttcgt caacaccgag ttcaaccacc ggcggctcgc cagggctcga    240
ggccccgagt tcacaaatgg aatgctgagc gactttcagt tcctgacaat ccccgatggt    300
cttcctcctt cggacttgga tgcgatccaa gacatcaaga tgctctgcga atcgtccagg    360
aactatatgg tcagccccat caacgatctt gtatcgagcc tgggctcgaa cccgagcgtc    420
cctccggtga cttgcatcaa tctcggatgg tttcatgaca ctcgtgac              468
```

<210> SEQ ID NO 32
<211> LENGTH: 405
<212> TYPE: DNA
<213> ORGANISM: Eucalyptus grandis

<400> SEQUENCE: 32

```
ctttactccg ccaagaagat ccaatcgcag ttttcgcaat ggcccatta cacaaatgcg      60 gtccatcttc atcgggaagt ctcttggcag aagaccggag ttgcatttcc tggctggaca    120
agcaagcccc taactcagtg gtctatgtga gtcttgggag catcgcctct gtgaacgagt    180
cggaattttc cgaaatagct ttaggtttag ccgatagcca gcagccattc ttgtgggtgg    240
ttcgacccgg gtcagtgagc ggctcggaac tcttagagaa tttgcccggt tgctttctgg    300
aggcattaca ggagaggggg aagattgtga aatgggcgcc tcaacatgaa gtgctggctc    360
atcgggctgt cggagcgttt tggactcaca atggatggaa ctcca                    405
```

<210> SEQ ID NO 33
<211> LENGTH: 380
<212> TYPE: DNA
<213> ORGANISM: Eucalyptus grandis

<400> SEQUENCE: 33

```
ggcaaacacg cccgttttcg ttttactaag agaagatggt gagcgttgtg gctggtagag      60
tcgagagctt gtcgagcagt ggcattcagt cgatcccgca ggagtatgtg aggccgaagg    120
aggagctcac aagcattggc gacatcttcg aggaggagaa gaagcatgag ggccctcagg    180
tcccgaccat cgacctcgag gacatagcgt ctaaagaccc cgtggtgagg gagaggtgcc    240
acgaggagct caggaaggct gccaccgact ggggcgtcat gcacctcgtc aaccatggga    300
tccccaacga cctgattgag cgtgtaaaga aggctggcga ggtgttcttc aacctcccga    360
tcgaggagaa ggacaagcat                                                 380
```

<210> SEQ ID NO 34
<211> LENGTH: 305
<212> TYPE: DNA
<213> ORGANISM: Eucalyptus grandis

<400> SEQUENCE: 34

```
ttgtacccga agatctccgg gaccgttcga cggcgacatc gccgtcggcc gggaacccgt      60
cgaggccgcc gccggaggcc ggggagaagc tggagtagcc gccgtagccg agaaggcgc    120 cgtcgtggtc ggcggcggcg gcgtggtgga ccctcatcgc gtccatgctg aaggcgtcga    180
aggaagcgga catggctggg ggatcgatcg accgatccga tcgccggag gatttcgaga    240 tcggagatgg agatggaa atgaaagaga gagagagaga gagatccggt ggactggtgg      300
tgttt                                                                 305
```

<210> SEQ ID NO 35
<211> LENGTH: 693
<212> TYPE: DNA
<213> ORGANISM: Eucalyptus grandis

<400> SEQUENCE: 35

```
gaattcggca cgagctaaga gaggagagga gaggagcaag atggcactag caggagctgc    60
actgtcagga accgtggtga gctccccctt tgtgaggatg cagcctgtga acagactcag   120
ggcattcccc aatgtgggtc aggccctgtt tggtgtcaac tctggccgtg cagagtgac    180
tgccatggcc gcttacaagg tcaccctgct caccccctgaa ggcaaagtcg aactcgacgt   240
ccccgacgat gtttacatct tggactacgc cgaggagcaa ggcatcgact tgccctactc   300
ctgccgtgcc ggctcttgct cctcctgcgc gggcaaggtc gtggcgggga gcgtcgacca   360
gagcgacggc agcttcctgg atgatgatca gattgaggaa ggttgggtcc tcacttgtgt   420
cgcctaccct aagtctgagg tcaccattga gacccacaag gaagaggagc tcactgcttg   480
aagctctcct atatttgctt ttgcataaat cagtctcact ctacgcaact ttctccactc   540
tctccccct tcactacatg tttgttagtt cctttagtct cttccttttt tactgtacga   600
gggatgattt gatgttattc tgagtctaat gtaatggctt ttcttttttcc tatttctgta   660
tgaggaaata aaactcatgc tctaaaaaaa aaa                                693
```

<210> SEQ ID NO 36
<211> LENGTH: 418
<212> TYPE: DNA
<213> ORGANISM: Eucalyptus grandis

<400> SEQUENCE: 36

```
aggactttat tataagcatt gtaaaaagag tcaaactaat acatcgcaag aattgggtta    60
tccaataatc tacaaaaaga aaaagtttg atgcattgag atggtaactg cttaattcaa   120
atgccttagt ttgaaaaatt aaccaactat taaaattaat gatgatgaat atggattatg   180
tgtgaaaaac tatatagact taaaattgac tcagaagaca ttcttttctt cttattttat   240
gatatgatga attcggtcta aacaggcaaa tggtgtcaaa cgggaagtcg gcaaaactct   300
tcctcggcag tgactaccgg gcgggcgatg atgcggatcc ggggccgggg tcgctggaga   360
acatcccgca cggaccggtc cacgtttggt gcggtgacaa caggcagccc aacctgga    418
```

<210> SEQ ID NO 37
<211> LENGTH: 777
<212> TYPE: DNA
<213> ORGANISM: Eucalyptus grandis

<400> SEQUENCE: 37

```
gaattcggca cgagcataca actacactgc gacgccgccg cagaacgcga gcgtgccgac    60
catgaacggc accaaggtct accggttgcc gtataacgct acggtccagc tcgttttaca   120
ggacaccggg ataatcgcgc cggagaccca ccccatccat ctgcacggat tcaacttctt   180
cggtgtgggc aaaggagtgg ggaattatga cccaaagaag gatcccaaga agttcaatct   240
ggttgaccca gtggagagga acaccattgg aatcccatct ggtggatgga tagccatcag   300
attcacagca gacaatccag gagtttggtt cctgcactgc catctggaag tgcacacaac   360
ttggggactg aagatggcat tcttggtgga caatgggaag gggcctaaag agaccctgct   420
tccacctcca gtgatcttc aaaatgttg atcatttgat catgaggacg acaagcgatt    480
actaatgaca ccaagttagt ggaatcttct ctttgaaaaa aagaagaag agcaagaaga   540
ataagaaaga tgaggagaga agccatgaaa gatttgacca agaagagaga gggcaataaa   600
ccaaagagac ccttgagatc acgacatccc gcaattgttt ctagagtaat agaaggattt   660
```

-continued

| actccgacac tgctacaata aattaaggaa gacaaggaat ttggtttttt tcattggagg | 720 |
| agtgtaattt gtttttggc aagctcatca catgaatcac atggaaaaaa aaaaaaa | 777 |

<210> SEQ ID NO 38
<211> LENGTH: 344
<212> TYPE: DNA
<213> ORGANISM: Eucalyptus grandis

<400> SEQUENCE: 38

| atatgttcag aatttcaaat gtgggaatgt caacctcctt gaacttcaga attcagggcc | 60 |
| atacgttgaa gctagtcgag gttgaaggat ctcacaccgt ccagaacatg tatgattcaa | 120 |
| tcgatgttca cgtgggccaa tccatggctg tcttagtgac cttaaatcag cctccaaagg | 180 |
| actactacat tgtcgcatcc acccggttca ccaagacggt tctcaatgca actgcagtgc | 240 |
| tacactacac caactcgctt accccagttt ccgggccact accagctggt ccaacttacc | 300 |
| aaaaacattg gtccatgaag caagcaagaa caatcaggtg gaac | 344 |

<210> SEQ ID NO 39
<211> LENGTH: 341
<212> TYPE: DNA
<213> ORGANISM: Eucalyptus grandis

<400> SEQUENCE: 39

| gccgcaactg caattctctt cgtaaaacat gacggctgtc ggcaaaacct ctttcctctt | 60 |
| gggagctctc ctcctcttct ctgtggcggt gacattggca gatgcaaaag tttactacca | 120 |
| tgattttgtc gttcaagcga ccaaggtgaa gaggctgtgc acgacccaca acaccatcac | 180 |
| ggtgaacggg caattcccgg gtccgacttt ggaagttaac gacggcgaca ccctcgttgt | 240 |
| caatgtcgtc aacaaagctc gctacaacgt caccattcac tggcacggcg tccggcaggt | 300 |
| gagatctggt tgggctgatg gggcggaatt tgtgactcaa t | 341 |

<210> SEQ ID NO 40
<211> LENGTH: 358
<212> TYPE: DNA
<213> ORGANISM: Eucalyptus grandis

<400> SEQUENCE: 40

| gaattcggca cgagatatgt tcagaatttc aaatgtggga atgtcaacct ccttgaactt | 60 |
| cagaattcag ggccatacgt tgaagctagt cgaggttgaa ggatctcaca ccgtccagaa | 120 |
| catgtatgat tcaatcgatg ttcacgtggg ccaatccatg gctgtcttag tgaccttaaa | 180 |
| tcagcctcca aaggactact acattgtcgc atccacccgg ttcaccaaga cggttctcaa | 240 |
| tgcaactgca gtgctacact acaccaactc gcttacccca gtttccgggc cactaccagc | 300 |
| tggtccaact taccaaaaac attggtccat gaagcaagca agaacaatca ggtggaac | 358 |

<210> SEQ ID NO 41
<211> LENGTH: 409
<212> TYPE: DNA
<213> ORGANISM: Eucalyptus grandis

<400> SEQUENCE: 41

| atcaagagtt tgagtctaaa ccttgtctaa tcctctctcg catagtcatt tggagacgaa | 60 |
| tgctgatcgg ccgcagctgc attctcttcg taaaacatga cggctgtcgg caaaacctct | 120 |
| ttcctcttgg gagctctcct cctcttctct gtggcggtga cattggcaga tgcaaaagtt | 180 |
| tactaccatg attttgtcgt tcaagcgacc aaggtgaaga ggctgtgcac gacccacaac | 240 |

```
accatcacgg tgaacgggca attcccgggt ccgactttgg aagttaacga cggcgacacc        300
ctcgttgtca atgtcgtcaa caaagctcgc tacaacgtca ccattcactg gcacggcgtc        360
cggcaggtga gatctggttg ggctgatggg gcggaatttg tgactcaat                   409

<210> SEQ ID NO 42
<211> LENGTH: 515
<212> TYPE: DNA
<213> ORGANISM: Eucalyptus grandis

<400> SEQUENCE: 42
ctctctctct ctctctctct gtgtgttcat tctcgttgag ctcgtggtcg cctcccgcca         60
tggatccgca caagtaccgt ccatccagtg ctttcaacac ttctttctgg actacgaact       120
ctggtgctcc tgtctggaac aataactctt cgttgactgt tggaagcaga ggtccaattc       180
ttcttgagga ttatcacctc gtggagaaac ttgccaactt gatagggag aggattccag        240 agcgtgtggt gcatgccaga ggagccagtg caaagggatt ctttgaggtc actcatgaca       300
tttcccagct tacctgtgct gatttccttc gggcaccagg agttcaaaca cccgtgattg       360
tccgtttctc cactgtcatc acgaaaggg gcagccctga aaccctgagg gaccctcgag       420
gttttgctgt gaagttctac acaagagagg gtaactttga tctggtggga aacaatttcc        480
ctgtcttctt tgtccgtaat gggataaatt ccccg                                 515

<210> SEQ ID NO 43
<211> LENGTH: 471
<212> TYPE: DNA
<213> ORGANISM: Eucalyptus grandis

<400> SEQUENCE: 43
gaattcggca cgaggctccc tctcgtactg ccatactcct gggacgggat tcggataggg         60
atttgcggcg atccatttct cgattcaagg ggaagaatca tggggaagtc ctacccgacc       120
gtaagccagg agtacaagaa ggctgtcgag aaatgcaaga agaagttgag aggcctcatc       180
gctgagaaga gctgcgctcc gctcatgctc cgcatcgcgt ggcactccgc cggtaccttc       240
gatgtgaaga cgaagaccgg aggcccgttc gggaccatga agcacgccgc ggagctcagc       300
cacggggcca acagcgggct cgacgttgcc gatcaggtct gcagccgat caaggatcag        360 ttccccgtca tcacttatgc tgatttctac cagctggctg cgtcgttgc tgtggaagtt       420 actggtggac ctgaagttgc ttttcacccg gaagagaggc aaaccacaac c                471

<210> SEQ ID NO 44
<211> LENGTH: 487
<212> TYPE: DNA
<213> ORGANISM: Eucalyptus grandis

<400> SEQUENCE: 44
gaattcggca cgagctccca cttctgtctc gccaccatta ctagcttcaa agcccagatc         60
tcagtttcgt gctctcttcg tcatctctgc ctcttgccat ggatccgtac aagtatcgcc       120
cgtccagcgc ttacgattcc agcttttgga caaccaacta cggtgctccc gtctggaaca       180
atgactcatc gctgactgtt ggaactagag gtccgattct cctggaggac taccatctga       240
ttgagaaact tgccaacttc gagagagaga ggattcctga gcgggtggtc catgcacggg       300
gagccagcgc gaaagggttc ttcgaggtca cccacgacat ctctcacttg acctgtgctg       360
atttcctccg ggctcctgga gtccagacgc ccgtaatcgt ccgtttctcc accgtcatcc       420
```

|  |  |
|---|---:|
| acgagcgcgg cagcccgaac ctcagggacc ctcgtggttt tgcagtgaag ttctacacca | 480 |
| gagaggg | 487 |

<210> SEQ ID NO 45
<211> LENGTH: 684
<212> TYPE: DNA
<213> ORGANISM: Pinus radiata

<400> SEQUENCE: 45

|  |  |
|---|---:|
| gaattcctgc agcccggggg atccactagt tctagagcgg ccgccaccgc ggtggagctc | 60 |
| gcgcgcctgc aggtcgacac tagtggatcc aaagaattcg cacgaggcc cgacggccac | 120 |
| ttgttggacg ccatggaagc tctccggaaa gccgggattc tggaaccgtt taaactgcag | 180 |
| cccaaggaag gactggctct cgtcaacggc acagcggtgg gatccgccgt ggccgcgtcc | 240 |
| gtctgttttg acgccaacgt gctgggcgtg ctggctgaga ttctgtctgc gctcttctgc | 300 |
| gaggtgatgc aagggaaacc ggagttcgta gatccgttaa cccaccagtt gaagcaccac | 360 |
| ccagggcaga tcgaagccgc ggccgtcatg gagttcctcc tcgacggtag cgactacgtg | 420 |
| aaagaagcag cgcggcttca cgagaaagac ccgttgagca aaccgaaaca agaccgctac | 480 |
| gctctgcgaa catcgccaca gtggttgggg cctccgatcg aagtcatccg cgctgctact | 540 |
| cactccatcg agcgggagat caattccgtc aacgacaatc cgttaatcga tgtctccagg | 600 |
| gacatggctc tccacggcgg caacttccag ggaacaccca tcggagtttc catggacaac | 660 |
| atgcgaatct ctttggcagc cgtc | 684 |

<210> SEQ ID NO 46
<211> LENGTH: 418
<212> TYPE: DNA
<213> ORGANISM: Pinus radiata

<400> SEQUENCE: 46

|  |  |
|---|---:|
| gaattcggca cgaggacaag gtcataggcc ctctcttcaa atgcttggat gggtggaaag | 60 |
| gaactcctgg cccattctga aataaataat cttccaagat cgcctttata caacgactgc | 120 |
| tatgatttga gtcctcggat cttttttgttg atgcagttgt ttaccgatct ggaatttgat | 180 |
| tggtcataaa gcttgatttt gttttttcttt cttttgttttt atactgctgg atttgcatcc | 240 |
| cattggattt gccagaaata tgtaaggtgg cagatcatt tgggtgatct gaaacatgta | 300 |
| aaagtggcgg atcatttggg tagcatgcag atcagttggg tgatcgtgta ctgctttcac | 360 |
| tattacttac atatttaaag atcgggaata aaaacatgat tttaattgaa aaaaaaaa | 418 |

<210> SEQ ID NO 47
<211> LENGTH: 479
<212> TYPE: DNA
<213> ORGANISM: Pinus radiata

<400> SEQUENCE: 47

|  |  |
|---|---:|
| gatatcccaa cgaccgaaaa cctgtatttt cagggcgcca tggggatccg gaattcggca | 60 |
| cgagcaagga agaaaatatg gttgcagcag cagaaattac gcaggccaat gaagttcaag | 120 |
| ttaaaagcac tgggctgtgc acggacttcg gctcgtctgg cagcgatcca ctgaactggg | 180 |
| ttcgagcagc caaggccatg gaaggaagtc actttgaaga agtgaaagcg atggtggatt | 240 |
| cgtatttggg agccaaggag atttccattg aagggaaatc tctgacaatc tcagacgttg | 300 |
| ctgccgttgc tcgaagatcg caagtgaaag tgaaattgga tgctgcggct gccaaatcta | 360 |
| gggtcgagga gagttcaaac tgggttctca cccagatgac caaggggacg gataccctatg | 420 | gtgtcactac tggtttcgga gccacttctc acaggagaac gaaccaggga gccgagctt    479

<210> SEQ ID NO 48
<211> LENGTH: 1785
<212> TYPE: DNA
<213> ORGANISM: Pinus radiata

<400> SEQUENCE: 48
tatcgataag cttgatatcg aattcctgca gcccggggga tccactagtt ctagagcggc     60
cgccaccgcg gtggagctcg cgcgcctgca ggtcgacact agtggatcca agaattcgg    120
cacgaggttg caggtcgggg atgatttgaa tcacagaaac ctcagcgatt ttgccaagaa    180
atatggcaaa atctttctgc tcaagatggg ccagaggaat cttgtggtag tttcatctcc    240
cgatctcgcc aaggaggtcc tgcacaccca gggcgtcgag tttgggtctc gaacccggaa    300
cgtggtgttc gatatcttca cgggcaaggg gcaggacatg gtgttcaccg tctatggaga    360
tcactggaga agatgcgca ggatcatgac tgtgcctttc tttacgaata agttgtcca    420
gcactacaga ttcgcgtggg aagacgagat cagccgcgtg tcgcggatg tgaaatcccg    480
cgccgagtct tccacctcgg gcattgtcat ccgtaggcgc ctccagctca tgatgtataa    540
tattatgtat aggatgatgt tcgacaggag attcgaatcc gaggacgacc cgcttttcct    600
caagctcaag gccctcaacg agagcgaag tcgattggcc cagagctttg agtacaatta    660
tggggatttc attcccattc ttaggccctt cctcagaggt tatctcagaa tctgcaatga    720
gattaaagag aaacggctct ctcttttcaa ggactacttc gtggaagagc gcaagaagct    780
caacagtacc aagactagta ccaacaccgg gggagctcaa gtgtgcaatg gaccatattt    840
tagatgctca ggacaaggga gagatcaatg aggataatgt tttgtacatc gttgagaaca    900
tcaacgttgc agcaattgag acaacgctgt ggtcgatgga atgggaata gcggagctgg    960
tgaaccacca ggacattcag agcaaggtgc gcgcagagct ggacgctgtt cttggaccag   1020
gcgtgcagat aacggaacca gacacgacaa ggttgcccta ccttcaggcg ttgtgaagg   1080
aaacccttcg tctccgcatg gcgatcccgt tgctcgtccc ccacatgaat ctccacgacg   1140
ccaagctcgg gggctacgat attccggcag agagcaagat cctggtgaac gcctggtggt   1200
tggccaacaa ccccgccaac tggaagaacc ccgaggagtt ccgccccgag cggttcttcg   1260
aggaggagaa gcacaccgaa gccaatggca acgacttcaa attcctgcct tcggtgtggg   1320
gaggaggagc tgcccgggaa tcattctggc gctgcctctc ctcgcactct ccatcggaag   1380
acttgttcag aacttccacc ttctgccgcc gcccgggcag agcaaagtgg atgtcactga   1440
gaagggcggg cagttcagcc ttcacattct caaccattct ctcatcgtcg ccaagcccat   1500
agcttctgct taatcccaac ttgtcagtga ctggtatata aatgcgcgca cctgaacaaa   1560
aaacactcca tctatcatga ctgtgtgtgc gtgtccactg tcgagtctac taagagctca   1620
tagcacttca aaagtttgct aggatttcaa taacagacac cgtcaattat gtcatgtttc   1680
aataaaagtt tgcataaatt aaatgatatt tcaatatact atttttgactc tccaccaatt   1740
ggggaatttt actgctaaaa aaaaaaaaaa aaaaaaaaa aaaaa              1785

<210> SEQ ID NO 49
<211> LENGTH: 475
<212> TYPE: DNA
<213> ORGANISM: Pinus radiata

<400> SEQUENCE: 49

| | |
|---|---|
| gaattcggca cgagatttcc atggacgatt ccgtttggct tcaattcgtt tcctctggct | 60 |
| gtcctcgtcc tcgttttcct tgttcttcct ccgactttt ctctggaagc tatggcgtaa | 120 |
| taggaacctg ccgccaggac ccccggcatg gccgatcgta gggaacgtcc ttcagattgg | 180 |
| attttccagc ggcgcgttcg agacctcagt gaagaaattc catgagagat acggtccaat | 240 |
| attcactgtg tggctcggtt cccgccctct gctgatgatc accgaccgcg agcttgccca | 300 |
| cgaggcgctc gtacagaagg gctccgtctt cgctgaccgc ccgcccgccc tcgggatgca | 360 |
| gaaaatcttc agtagcaacc agcacaacat cacttcggct gaatacgcc cgctgtggcg | 420 |
| gagccttcgc aggaatctgg ttaaagaagc cctgagactt cggcgatgaa ggctt | 475 |

<210> SEQ ID NO 50
<211> LENGTH: 801
<212> TYPE: DNA
<213> ORGANISM: Pinus radiata

<400> SEQUENCE: 50

| | |
|---|---|
| gctccaccga cggtggacgg tccgctactc agtaactgag tgggatcccc cgggctgaca | 60 |
| ggcaattcga tttagctcac tcattaggca ccccaggctt tacactttat gcttccggct | 120 |
| cgtatgttgt gtggaattgt gagcggataa caatttcaca caggaaacag ctatgaccat | 180 |
| gattacgcca agcgcgcaat taaccctcac taaagggaac aaaagctgga gctccaccgc | 240 |
| ggtggcggcc gctctagaac tagtggatcc aaagaattcg gcacgagacc cagtgacctt | 300 |
| caggcctgag agatttcttg aggaagatgt tgatattaag ggccatgatt acaggctact | 360 |
| gccattcggt gcagggcgca ggatctgccc tggtgcacaa ttgggtatta atttagttca | 420 |
| gtctatgttg ggacacctgc ttcatcattt cgtatgggca cctcctgagg gaatgaaggc | 480 |
| agaagacata gatctcacag agaatccagg gcttgttact ttcatggcca agcctgtgca | 540 |
| ggccattgct attcctcgat tgcctgatca tctctacaag cgacagccac tcaattgatc | 600 |
| aattgatctg atagtaagtt tgaattttgt tttgatacaa acgaaataa cgtgcagttt | 660 |
| ctcctttcc atagtcaaca tgcagctttc tttctctgaa gcgcatgcag cttctttct | 720 |
| ctgaagccca acttctagca agcaataact gtatatttta gaacaaatac ctattcctca | 780 |
| aattgagtat ttctctgtag g | 801 |

<210> SEQ ID NO 51
<211> LENGTH: 744
<212> TYPE: DNA
<213> ORGANISM: Pinus radiata

<400> SEQUENCE: 51

| | |
|---|---|
| gggccccct tcgaggtgga cactagtgga tccaaagaat tcggcacgag gttttatctg | 60 |
| aaggacgctg tgcttgaagg ctcccagcca ttcaccaaag cccatggaat gaatgcgttc | 120 |
| gagtacccgg ccatcgatca gagattcaac aagattttca cagggctat gtctgagaat | 180 |
| tctaccatgt tgatgaacaa gattttggat acttacgagg ttttaagga ggttcaggag | 240 |
| ttggtggatg tgggaggagg tattgggtcg actctcaatc tcatagtgtc taggtatccc | 300 |
| cacatttcag gaatcaactt cgacttgtcc catgtgctgg ccgatgctcc tcactaccca | 360 |
| gctgtgaaac atgtgggtgg agacatgttt gatagtgtac caagtggcca agctatttt | 420 |
| atgaagtgga ttctgcatga ttggagcgat gatcattgca ggaagctttt gaagaattgt | 480 |
| cacaaggcgt tgccagagaa ggggaaggtg attgcggtgc acaccattct cccagtggct | 540 |
| gcagagacat ctccttatgc tcgtcaggga tttcatacag atttactgat gttggcatac | 600 |

```
aacccagggg gcaaggaacg cacagagcaa gaatttcaag atttagctaa ggagacggga      660
tttgcaggtg gtgttgaacc tgtatgttgt gtcaatggaa tgtgggtaat ggaattcctg      720
cagcccgggg gatccactag ttct                                             744
```

<210> SEQ ID NO 52
<211> LENGTH: 426
<212> TYPE: DNA
<213> ORGANISM: Pinus radiata

<400> SEQUENCE: 52

```
gtggccctgg aagtagtgtg cgcgacatgg attccttgaa tttgaacgag tttatgttgt       60
ggtttctctc ttggcttgct ctctacattg gatttcgtta tgttttgaga tcgaacttga      120
agctcaagaa gaggcgcctc ccgccgggcc catcgggatg ccagtggtg ggaagtctgc       180 cattgctggg agcgatgcct cacgttactc tctacaacat gtataagaaa tatggccccg      240
ttgtctatct caaactgggg acgtccgaca tggttgtggc ctccacgccc gctgcagcta      300
aggcgtttct gaagactttg gatataaact tctccaaccg gccgggaaat gcaggagcca      360
cgtacatcgc ctacgattct caggacatgg tgtgggcagc gtatggagga cggtggaaga      420
tggagc                                                                 426
```

<210> SEQ ID NO 53
<211> LENGTH: 562
<212> TYPE: DNA
<213> ORGANISM: Pinus radiata

<400> SEQUENCE: 53

```
cagttcgaaa ttaacctcac taaagggaac aaaagctgga gttcgcgcgc ctgcaggtcg       60
acactagtgg atccaaagaa ttcggcacga gctttgaggc aacctacatt cattgaatcc      120
caggatttct tcttgtccaa acaggtttaa ggaaatggca ggcacaagtg ttgctgcagc      180
agaggtgaag gctcagacaa cccaagcaga ggagccggtt aaggttgtcc gccatcaaga      240
agtgggacac aaaagtcttt tgcagagcga tgccctctat cagtatatat tggaaacgag      300
cgtgtaccct cgtgagcccg agccaatgaa ggagctccgc gaagtgactg ccaagcatcc      360
ctggaacctc atgactactt ctgccgatga gggtcaattt ctgggcctcc tgctgaagct      420
cattaacgcc aagaacacca tggagattgg ggtgtacact ggttactcgc ttctcagcac      480
agcccttgca ttgcccgatg atggaaagat tctagccatg gacatcaaca gagagaacta      540
tgatatcgga ttgcctataa tt                                               562
```

<210> SEQ ID NO 54
<211> LENGTH: 1074
<212> TYPE: DNA
<213> ORGANISM: Pinus radiata

<400> SEQUENCE: 54

```
tcgtgccgct cgatcctcac aggcccttt tatttccctg gtgaacgata cgatgggctc       60
gcacgctgag aatggcaacg gggtggaggt tgttgatcca acggacttaa ctgacatcga      120
gaatgggaaa ccaggttatg acaagcgtac gctgcctgcg gactggaagt ttggagtgaa      180
gcttcaaaac gttatggaag aatccattta caagtacatg ctggaaacat tcacccgcca      240
tcgagaggac gaggcgtcca aggagctctg ggaacgaaca tggaacctga cacagagagg      300
ggagatgatg acattgccag atcaggtgca gttcctgcgc ttgatggtaa agatgtcagg      360
```

```
tgctaaaaag gcattggaga tcggagtttt cactggctat tcattgctca atatcgctct    420
cgctcttcct tctgatggca aggtggtagc tgtggatcca ggagatgacc ccaaatttgg    480
ctggccctgc ttcgttaagg ctggagttgc agacaaagtg gagatcaaga aaactacagg    540
gttggactat ttggattccc ttattcaaaa gggggagaag gattgcttcg actttgcatt    600
cgtggacgca gacaaagtga actacgtgaa ctatcatcca cggctgatga agttagtgcg    660 cgtgggggc gtcataattt acgacgacac cctctggttt ggtctggtgg aggaaagga     720 tccccacaac ctgcttaaga atgattacat gaggacttct ctggagggta tcaaggccat    780
caactccatg gtagccaacg accccaactt ggaggtcgcc acagtcttta tgggatatgg    840
tgtcactgtt tgttaccgca ctgcttagtt agctagtcct ccgtcattct gctatgtatg    900
tatatgataa tggcgtcgat tctgatata ggtggttttt caatgtttct atcgtcatgt     960
tttctgttta gccagaatgt ttcgatcgtc atggtttctg ttaaagcag aataaaatta     1020 gccgcttgca gttcaaaaaa aaaaaaaaa aaaaactcga gactagttct cttc            1074
```

<210> SEQ ID NO 55
<211> LENGTH: 1075
<212> TYPE: DNA
<213> ORGANISM: Pinus radiata

<400> SEQUENCE: 55

```
tcggagctct cgaatcctca caggcccttt ttatttccct ggtgaacgat acgatgggct    60
cgcacgctga gaatggcaac ggggtggagg ttgttgatcc aacggactta actgacatcg    120
aagaatggga aaccaggtta tgacaagcgt cgctgcctgc ggactggaag tttggagtga    180
agcttcaaaa cgttatggaa gaatccattt acaagtacat gctggaaaca ttcacccgcc    240
atcgagagga cgaggcgtcc aaggagctct gggaacgaac atggaacctg acacagagag    300
gggagatgat gacattgcca gatcaggtgc agttcctgcg cttgatggta agatgtcag    360 gtgctaaaaa ggcattggag atcggagttt tcactggcta ttcattgctc aatatcgctc    420
tcgctcttcc ttctgatggc aaggtggtag ctgtggatcc aggagatgac cccaaatttg    480
gctggccctg cttcgttaag gctggagttg cagacaaagt ggagatcaag aaaactacag    540
ggttggacta tttggattcc cttattcaaa agggggagaa ggattgcttc gactttgcat    600
tcgtggacgc agacaaagtg aactacgtga actatcatcc acggctgatg aagttagtgc    660
gcgtgggggg cgtcataatt tacgacgaca ccctctggtt tggtctggtg ggaggaaagg    720
atccccacaa cctgcttaag aatgattaca tgaggacttc tctggagggt atcaaggcca    780
tcaactccat ggtagccaac gaccccaact tggaggtcgc cacagtcttt atgggatatg    840
gtgtcactgt ttgttaccgc actgcttagt tagctagtcc tccgtcattc tgctatgtat    900
gtatatgata atggcgtcga tttctgatat aggtggtttt tcaatgtttc tatcgtcatg    960
ttttctgttt agccagaatg tttcgatcgt catggtttct gttaaagcca gaataaaatt    1020
agccgcttgc agttcaaaaa aaaaaaaaaa aaaaaactcg agactagttc tcttc          1075
```

<210> SEQ ID NO 56
<211> LENGTH: 1961
<212> TYPE: DNA
<213> ORGANISM: Pinus radiata

<400> SEQUENCE: 56

```
gttttccgcc attttcgcc tgtttctgcg gagaatttga tcaggttcgg attgggattg    60
aatcaattga aaggttttta ttttcagtat ttcgatcgcc atggccaacg gaatcaagaa    120
```

```
ggtcgagcat ctgtacagat cgaagcttcc cgatatcgag atctccgacc atctgcctct      180
tcattcgtat tgctttgaga gagtagcgga attcgcagac agaccctgtc tgatcgatgg      240
ggcgacagac agaacttatt gcttttcaga ggtggaactg atttctcgca aggtcgctgc      300
cggtctggcg aagctcgggt tgcagcaggg gcaggttgtc atgcttctcc ttccgaattg      360
catcgaattt gcgtttgtgt tcatgggggc ctctgtccgg ggcgccattg tgaccacggc      420
caatcctttc tacaagccgg gcgagatcgc caaacaggcc aaggccgcgg gcgcgcgcga      480
tcatagttac cctggcagct tatgtggaga aactggccga tctgcagagc cacgatgtgc      540
tcgtcatcac aatcgatgat gctcccaagg aaggttgcca acatatttcc gttctgaccg      600
aagccgacga acccaatgc ccggccgtga caatccaccc ggacgatgtc gtggcgttgc       660
cctattcttc cggaaccacg gggctcccca agggcgtgat gttaacgcac aaaggcctgg      720
tgtccagcgt tgcccagcag gtcgatggtg aaaatcccaa tctgtatttc cattccgatg      780
acgtgatact ctgtgtcttg cctctttttcc acatctattc tctcaattcg gttctcctct      840
gcgcgctcag agccggggct gcgaccctga ttatgcagaa attcaacctc acgacctgtc      900
tggagctgat tcagaaatac aaggttaccg ttgccccaat tgtgcctcca attgtcctgg      960
acatcacaaa gagccccatc gtttcccagt acgatgtctc ggccgtccgg ataatcatgt     1020
ccggcgctgc gcctctcggg aaggaactcg aagatgccct cagagagcgt tttcccaagg     1080
ccattttcgg gcagggctac ggcatgacag aagcaggccc ggtgctggca atgaacctag     1140
ccttcgcaaa gaatcctttc cccgtcaaat ctggctcctg cggaacagtc gtccggaacg     1200
ctcaaataaa gatcctcgat acagaaactg gcgagtctct cccgcacaat caagccggcg     1260
aaatctgcat ccgcggaccc gaaataatga aaggatatat taacgacccg gaatccacgg     1320
ccgctacaat cgatgaagaa ggctggctcc acacaggcga cgtcgggtac attgacgatg     1380
acgaagaaat cttcatagtc gacagagtaa aggagattat caaatataag ggcttccagg     1440
tggctcctgc tgagctggaa gctttacttg ttgctcatcc gtcaatcgct gacgcagcag     1500
tcgttcctca aaagcacgag gaggcgggcg aggttccggt ggcgttcgtg gtgaagtcgt     1560
cggaaatcag cgagcaggaa atcaaggaat tcgtggcaaa gcaggtgatt ttctacaaga     1620
aaatacacag agtttacttt gtggatgcga ttcctaagtc gccgtccggc aagattctga     1680
gaaaggattt gagaagcaga ctggcagcaa atgaaaatg aatttccata tgattctaag     1740
attcctttgc cgataattat aggattcctt tctgttcact tctatttata taataaagtg     1800
gtgcagagta agcgccctat aaggagagag agagcttatc aattgtatca tatggattgt     1860
caacgcccta cactcttgcg atcgctttca atatgcatat tactataaac gatatatgtt     1920 tttttataa atttactgca cttctcgttc aaaaaaaaa a                           1961
```

<210> SEQ ID NO 57
<211> LENGTH: 1010
<212> TYPE: DNA
<213> ORGANISM: Pinus radiata

<400> SEQUENCE: 57

```
gacaaacttg gtcgtttgtt taggttttgc tgcaggtgaa cactaatatg gaaggccaga       60
ttgcagcatt aagcaaagaa gatgagttca tttttcacag cccttttcct gcagtacctg      120
ttccagagaa tataagtctt ttccagtttg ttctggaagg tgctgagaaa taccgtgata      180
aggtggccct cgtggaggcc tccacaggga aggagtacaa ctatggtcag gtgatttcgc      240
```

-continued

| | | |
|---|---|---|
| tcacaaggaa tgttgcagct gggctcgtgg acaaaggcat tcaaaagggc gatgttgtat | 300 |
| ttgttctgct tccaaatatg gcagaatacc ccattattgt gctgggaata atgttggccg | 360 |
| gcgcagtgtt ttctggggca aatccttctg cacacatcaa tgaagttgaa aaacatatcc | 420 |
| aggattctgg agcaaagatt gttgtgacag ttgggtctgc ttatgagaag gtgaggcaag | 480 |
| tgaaactgcc tgttattatt gcagataacg agcatgtcat gaacacaatt ccattgcagg | 540 |
| aaattttga gagaaactat gaggccgcag ggccttttgt acaaatttgt caggatgatc | 600 |
| tgtgtgcact cccttattcc tctggcacca caggggcctc taaaggtgtc atgctcactc | 660 |
| acagaaatct gattgcaaat ctgtgctcta gcttgtttga tgtccatgaa tctcttgtag | 720 |
| gaaatttcac cacgttgggg ctgatgccat tctttcacat atatggcatc acgggcatct | 780 |
| gttgcgccac tcttcgcaac ggaggcaagg tcgtggtcat gtccagattc gatctccgac | 840 |
| actttatcag ttctttgatt acttatgagg tcaacttcgc gcctattgtc ccgcctataa | 900 |
| tgctctccct ccggtttaaa aatcctatcg ttaacgagtt cgatctcagc cgcttgaaac | 960 |
| tccaaagctg ttcatgactg cggctgctcc actggcgccg gatctactgc | 1010 |

<210> SEQ ID NO 58
<211> LENGTH: 741
<212> TYPE: DNA
<213> ORGANISM: Pinus radiata

<400> SEQUENCE: 58

| | | |
|---|---|---|
| gaattcggca cgagaccatt tccagctaat attggcatag caattggtca ttctatcttt | 60 |
| gtcaaaggag atcaaacaaa ttttgaaatt ggacctaatg gtgtggaggc tagtcagcta | 120 |
| tacccagatg tgaaatatac cactgtcgat gagtacctca gcaaatttgt gtgaagtatg | 180 |
| cgagattctc ttccacatgc ttcagagata cataacagtt tcaatcaatg tttgtcctag | 240 |
| gcatttgcca aattgtgggt tataatcctt cgtaggtgtt tggcagaaca gaacctcctg | 300 |
| tttagtatag tatgacgagc taggcactgc agatccttca cacttttctc ttccataaga | 360 |
| aacaaatact cacctgtggt ttgttttctt tctttctgga actttggtat ggcaataatg | 420 |
| tcttggaaa ccgcttagtg tggaatgcta agtactagtg tccagagttc taagggagtt | 480 |
| ccaaaatcat ggctgatgtg aactggttgt tccagagggt gtttacaacc aacagttgtt | 540 |
| cagtgaataa ttttgttaga gtgtttagat ccatctttac aaggctattg agtaaggttg | 600 |
| gtgttagtga acggaatgat gtcaaatctt gatgggctga ctgactctct tgtgatgtca | 660 |
| aatcttgatg gattgtgtct ttttcaatgg taaaaaaaa aaaaaaaaa aaaaaaaaa | 720 |
| aaaaaaaaa aaaaaaaaa a | 741 |

<210> SEQ ID NO 59
<211> LENGTH: 643
<212> TYPE: DNA
<213> ORGANISM: Pinus radiata

<400> SEQUENCE: 59

| | | |
|---|---|---|
| ctcatctcgg agttgcaggc tgcagctttt ggcccaaagc atgatatcag atcaaacgac | 60 |
| gcagatgaag caaacggatc aaacagtttg cgttactgga gcagcgggtt tcattgcctc | 120 |
| atggcttgtc aagatgctcc tcatcagagg ttacactgtc agagcagcag ttcggaccaa | 180 |
| cccagctgat gataggtgga agtatgagca tctgcgagag ttggaaggag caaaagagag | 240 |
| gcttgagctt gtgaaagctg atattctcca ttaccagagc ttactcacag tcatcagagg | 300 |
| ttgccacggt gtctttcaca tggcttcagt tctcaatgat gaccctgagc aagtgataga | 360 |

```
accagcagtc gaagggacga ggaatgtgat ggaggcctgc gcagaaactg gggtgaagcg       420
cgttgttttt acttcttcca tcggcgcagt ttacatgaat cctcatagag acccgctcgc       480
gattgtccat gatgactgct ggagcgattt gactactgcg tacaaaccaa gaattggtat       540
tgctatgcaa aaaccttggc agagaaatct gcatgggata ttgctaaggg aaggaattta       600
gagcttgcag tgataaatcc aggcctggcc ttaggtccct tga                        643
```

<210> SEQ ID NO 60
<211> LENGTH: 441
<212> TYPE: DNA
<213> ORGANISM: Pinus radiata

<400> SEQUENCE: 60

```
gaattcggca cgagaatttt tctgtggtaa gcatatctat ggctcaaacc agagagaagg        60
acgatgtcag cataacaaac tccaaaggat tggtatgcgt gacaggagcg gctggttact       120
tggcatcttg gcttatcaag cgtctcctcc agtgtggtta ccaagtgaga ggaactgtgc       180
gggatcctgg caatgagaaa aagatggctc atttatggaa gttagatggg gcgaaagaga       240
gactgcaact aatgaaagct gatttaatgg acgagggcag cttcgatgag gtcatcagag       300
gctgccatgt gttttttcac acagcgtctc cagtcgtggg tgtcaaatca gatcccaaga       360
tatggtatgc tctggccaag actttagcag aaaaagcagc atgggatttt gcccaagaaa       420
accatctgga catggttgca g                                                441
```

<210> SEQ ID NO 61
<211> LENGTH: 913
<212> TYPE: DNA
<213> ORGANISM: Pinus radiata

<400> SEQUENCE: 61

```
gaattcggca cgaggaaaac atcatccagg cattttggaa atttagctcg ccggttgatt        60
caggatcctg caatggcttt tggcgaagag cagactgcct tgccacaaga aacgcctttg       120
aatcctccgg tccatcgagg aacagtgtgc gttacaggag ctgctgggtt catagggtca       180
tggctcatca tgcgattgct tgagcgagga tatagtgtta gagcaactgt gcgagacact       240
ggtaatcctg taaagacaaa gcatctgttg gatctgccgg gggcaaatga gagattgact       300
ctctggaaag cagatttgga tgatgaagga agctttgatg ctgccattga tgggtgtgag       360
ggtgttttcc atgttgccac tcccatggat ttcgagtccg aggatcccga gaatgagata       420
attaagccaa caatcaacgg ggtcttgaat gttatgagat cgtgtgcaaa agccaagtcc       480
gtgaagcgag ttgttttcac gtcatctgct gggactgtga attttacaga tgatttccaa       540
acaccaggca agttttttga cgaatcatgc tggaccaacg tggatctttg cagaaaagtt       600
aaaatgacag gatggatgta ctttgtatcg aagacattag cagagaaagc tgcttgggat       660
tttgcagagg agaacaagat cgatctcatt actgttatcc ccacattggt cgttggacca       720
ttcattatgc agaccatgcc accgagcatg atcacagcct ggcactgtt aacgcggaat       780 gaacccccact acatgatact gagacaggta cagctggttc acttggatga tctctgtatg       840
tcacatatct ttgtatatga acatcctgaa gcaaagggca gatacatctc ttccacatgt       900
gatgctaccc att                                                         913
```

<210> SEQ ID NO 62
<211> LENGTH: 680
<212> TYPE: DNA

<213> ORGANISM: Pinus radiata

<400> SEQUENCE: 62

| | | | | | |
|---|---|---|---|---|---|
| gaattcggca | cgagatcaat | ttttgcatat | tattaaaaag | taagtgtatt | cgttctctat | 60 |
| attgatcagt | cacagagtca | tggccagttg | tggttccgag | aaagtaagag | ggttgaatgg | 120 |
| agatgaagca | tgcgaagaga | acaagagagt | ggtttgtgta | actggggcaa | atgggtacat | 180 |
| cggctcttgg | ctggtcatga | gattactgga | acatggctat | tatgttcatg | gaactgttag | 240 |
| ggacccagaa | gacacaggga | aggttgggca | tttgctgcgg | ctcccagggg | caagtgagaa | 300 |
| gctaaagctg | ttcaaggcag | agcttaacga | cgaaatggcc | tttgatgatg | ctgtgagcgg | 360 |
| ttgtcaaggg | gtttccacg | ttgccaagcc | tgttaatctg | gactcaaacg | ctcttcaggg | 420 |
| ggaggttgtt | ggtcctgcgg | tgagggaac | agtaaatctg | cttcgagcct | gcgaacgatc | 480 |
| gggcactgtg | aaacgagtga | tacataccte | gtccgtttca | gcagtgagat | tcactgggaa | 540 |
| acctgacccc | cctgatactg | tgctggatga | atctcattgg | acttcggtcg | agtattgcag | 600 |
| aaagacaaag | atggtcggat | ggatgtacta | catcgccaac | acttatgcag | aagagggagc | 660 |
| ccataagttc | ggatcagaga | | | | | 680 |

<210> SEQ ID NO 63
<211> LENGTH: 492
<212> TYPE: DNA
<213> ORGANISM: Pinus radiata

<400> SEQUENCE: 63

| | | | | | |
|---|---|---|---|---|---|
| gaattcggca | cgaggctggt | tcaagtgtca | gcccaatggc | ctcccctaca | gagaatcccc | 60 |
| agatttcaga | agagctgcta | aatcatgaga | tccatcaagg | aagtacagta | tgtgtgacag | 120 |
| gagctgctgg | cttcatagga | tcatggctcg | tcatgcgttt | gcttgagcga | ggatatactg | 180 |
| ttagaggaac | tgtgcgagac | actggtaatc | cggtgaagac | gaagcatcta | ttggatctgc | 240 |
| ctggggcgaa | tgagaggtta | actctctgga | aagcagattt | ggatgatgaa | ggaagctttg | 300 |
| acgccgccat | tgatggttgt | gagggagttt | tccatgttgc | cactcccatg | gattttgaat | 360 |
| ccgaggaccc | cgagaacgag | ataattaaac | ccgctgtcaa | tgggatgttg | aatgttttga | 420 |
| gatcgtgtgg | gaaaaccaag | tctatgaagc | gagttgtttt | cacgtcgtct | gctgggactc | 480 |
| tgcttttac | gg | | | | | 492 |

<210> SEQ ID NO 64
<211> LENGTH: 524
<212> TYPE: DNA
<213> ORGANISM: Pinus radiata

<400> SEQUENCE: 64

| | | | | | |
|---|---|---|---|---|---|
| gaattcggca | cgagcttgtt | caaagtcaca | tatcttattt | tctttgtgat | atctgcaatt | 60 |
| tccaagcttt | tcgtctacct | ccctgaaaag | atgagcgagg | tatgcgtgac | aggaggcaca | 120 |
| ggcttcatag | ctgcttatct | cattcgtagt | cttctccaga | aaggttacag | agttcgcact | 180 |
| acagttcgca | acccagataa | tgtggagaag | tttagttatc | tgtgggatct | gcctggtgca | 240 |
| aacgaaagac | tcaacatcgt | gagagcagat | ttgctagagg | aaggcagttt | tgatgcagca | 300 |
| gtagatggtg | tagatggagt | attccatact | gcatcacctg | tcttagtccc | atataacgag | 360 |
| cgcttgaagg | aaaccctaat | agatccttgt | gtgaagggca | ctatcaatgt | cctcaggtcc | 420 |
| tgttcaagat | caccttcagt | aaagcgggtg | gtgcttacat | cctcctgctc | atcaataccg | 480 |
| atacgactat | aatagcttag | agcgttccct | gctggactga | gtca | | 524 |

<210> SEQ ID NO 65
<211> LENGTH: 417
<212> TYPE: DNA
<213> ORGANISM: Pinus radiata

<400> SEQUENCE: 65

| tcctaattgt | tcgatcctcc | cttttaaagc | ccttccctgg | ccttcattcc | aggtcacaga | 60 |
| gttgttcatg | cagtgctagc | aggaggagca | gcgttgcaat | ggggaaaat  | tccaaaatca | 120 |
| ataacgagag | gacagaagta | agtttgtgga | aatagcaacc | atgccggtgt | ttccttctgg | 180 |
| tctggacccc | tctgaggaca | atggcaagct | cgtttgtgtc | atggatgcgt | ccagttatgt | 240 |
| aggtttgtgg | attgttcagg | gccttcttca | acgaggctat | tcagtgcatg | ccacggtgca | 300 |
| gagagacgct | ggcgaggttg | agtctctcag | aaaattgcat | ggggatcgat | tgcagatctt | 360 |
| ctatgcagat | gtcttggatt | atcacagcat | tactgatgcg | ctcaagggct | gttctgg    | 417 |

<210> SEQ ID NO 66
<211> LENGTH: 511
<212> TYPE: DNA
<213> ORGANISM: Pinus radiata

<400> SEQUENCE: 66

| atgacacgaa | tttgtgcctc | tctctgacca | gagcttgaag | ctctgtcttc | tctgatatcg | 60 |
| cttcattcca | tcatccagga | gcttctgtta | tatccatttc | ctcaaaatgg | atgcctacct | 120 |
| tgaagaaaat | ggatacggcg | cttccaattc | tcggaaatta | atgtgcctta | ccgggggctg | 180 |
| gagtttcctg | gggattcata | tcgcaagaat | gctgctcggc | cggggttact | cagtccgttt | 240 |
| cgcaattccg | gtaacgccag | aagaggcagg | ctcacttatg | gaatccgaag | aagcattatc | 300 |
| ggggaagctg | gagatatgcc | aagccgatct | cttggattat | cgcagcgttt | tcggcaacat | 360 |
| caatggttgc | tccggagtct | tccacgtccc | tgcgccctgt | gatcatctgg | atggattaca | 420 |
| ggagtatccg | gtatgattag | tttaatagat | tgacggggta | tcctgtatga | attagtttat | 480 |
| gaatttaagg | ttttcttaga | atttggatac | t          |            |            | 511 |

<210> SEQ ID NO 67
<211> LENGTH: 609
<212> TYPE: DNA
<213> ORGANISM: Pinus radiata

<400> SEQUENCE: 67

| cattgatagt | tgatggaaga | ccatcagtaa | agcatgaaaa | agaaattgtt | ccaaggtgaa | 60 |
| gaagtcagtt | gctccagcag | aacctttta  | gcaattgttt | ttgtatcctt | tttgcctttg | 120 |
| aatatgtaat | ccataaactt | atgcaggaag | tgcctcgtgc | cgaattcggc | acgagaatca | 180 |
| ctgaccttca | catatttatt | ccaattctaa | tatctctact | cgctgtctac | ctgattttc  | 240 |
| agtggcgaac | caacttgaca | gggttggaca | tggccaacag | cagcaagatt | ctgattattg | 300 |
| gaggaacagg | ctacattggt | cgtcatataa | ccaaagccag | ccttgctctt | ggtcatccca | 360 |
| cattccttct | tgtcagagag | acctccgctt | ctaatcctga | gaaggctaag | cttctggaat | 420 |
| ccttcaaggc | ctcaggtgct | attatactcc | atggatcttt | ggaggaccat | gcaagtcttg | 480 |
| tggaggcaat | caagaaagtt | gatgtagtta | tctcggctgt | caagggacca | cagctgacgg | 540 |
| ttcaaacagg | atatttatcc | aggtattta  | aagggagggt | tggaacccat | caagaagggt | 600 |
| tttggccaa  |            |            |            |            |            | 609 |

<210> SEQ ID NO 68
<211> LENGTH: 474
<212> TYPE: DNA
<213> ORGANISM: Pinus radiata

<400> SEQUENCE: 68

| | | | | | |
|---|---|---|---|---|---|
| gcaagatagg | ttttattctt | ctggagttgg | gtgaggcttg | gaaatttaag | taaaaagggt | 60 |
| gcatagcaat | taagcagttg | cagccatggc | ggtctgtgga | actgaagtag | ctcatactgt | 120 |
| gctctatgta | gctgcagaca | tggtggaaaa | caacacgtct | attgtgacca | cctctatggc | 180 |
| tgcagcaaat | tgtgagatgg | agaagcctct | tctaaattcc | tctgccacct | caagaatact | 240 |
| ggtgatggga | gccacaggtt | acattggccg | ttttgttgcc | caagaagctg | ttgctgctgg | 300 |
| tcatcctacc | tatgctctta | tacgcccgtt | tgctgcttgt | gacctggcca | agcacagcg | 360 |
| cgtccaacaa | ttgaaggatg | ccggggtcca | tatcctttat | gggtctttga | gtgatcacaa | 420 |
| cctcttagta | aatacattga | aggacatggg | ccgttgttat | ctctaccatt | ggag | 474 |

<210> SEQ ID NO 69
<211> LENGTH: 474
<212> TYPE: DNA
<213> ORGANISM: Pinus radiata

<400> SEQUENCE: 69

| | | | | | |
|---|---|---|---|---|---|
| gcaagatagg | ttttattctt | ctggagttgg | gtgaggcttg | gaaatttaag | taaaaagggt | 60 |
| gcatagcaat | taagcagttg | cagccatggc | ggtctgtgga | actgaagtag | ctcatactgt | 120 |
| gctctatgta | gctgcagaca | tggtggaaaa | caacacgtct | attgtgacca | cctctatggc | 180 |
| tgcagcaaat | tgtgagatgg | agaagcctct | tctaaattcc | tctgccacct | caagaatact | 240 |
| ggtgatggga | gccacaggtt | acattggccg | ttttgttgcc | caagaagctg | ttgctgctgg | 300 |
| tcatcctacc | tatgctctta | tacgcccgtt | tgctgcttgt | gacctggcca | agcacagcg | 360 |
| cgtccaacaa | ttgaaggatg | ccggggtcca | tatcctttat | gggtctttga | gtgatcacaa | 420 |
| cctcttagta | aatacattga | aggacatggg | ccgttgttat | ctctaccatt | ggag | 474 |

<210> SEQ ID NO 70
<211> LENGTH: 608
<212> TYPE: DNA
<213> ORGANISM: Pinus radiata

<400> SEQUENCE: 70

| | | | | | |
|---|---|---|---|---|---|
| cattgatagt | tgatggaaga | ccatcagtaa | agcatgaaaa | agaaattgtt | ccaaggtgaa | 60 |
| gaagtcagtt | gctccagcag | aacctttta | gcaattgttt | ttgtatcctt | tttgcctttg | 120 |
| aatatgtaat | ccataaactt | atgcaggaag | tgcctcgtgc | cgaattcggc | acgagaatca | 180 |
| ctgaccttca | aatatttatt | ccaattctaa | tatctctact | cgctgtctac | ctgattttc | 240 |
| agtggcgaac | caacttgaca | gggttggaca | tggccaacag | cagcaagatt | ctgattattg | 300 |
| gaggaacagg | ctacattggt | cgtcatataa | ccaaagccag | ccttgctctt | ggtcatccca | 360 |
| cattccttct | tgtcagagag | acctccgctt | ctaatcctga | gaaggctaag | cttctggaat | 420 |
| ccttcaaggc | ctcaggtgct | attatactcc | atggatcttt | ggaggaccat | gcaagtcttg | 480 |
| tggaggcaat | caagaaagtt | gatgtagtta | tctcggctgt | caagggacca | cagctgacgg | 540 |
| atcaaacagg | atatttatcc | agggtattta | aagggaggtt | ggaacccatc | aagaagggtt | 600 |
| ttggccaa | | | | | | 608 |

<210> SEQ ID NO 71
<211> LENGTH: 1474
<212> TYPE: DNA
<213> ORGANISM: Pinus radiata

<400> SEQUENCE: 71

| | | | | | |
|---|---|---|---|---|---|
| gaattcggca | cgagaaaacg | tccatagctt | ccttgccaac | tgcaagcaat | acagtacaag | 60 |
| agccagacga | tcgaatcctg | tgaagtggtt | ctgaagtgat | gggaagcttg | gaatctgaaa | 120 |
| aaactgttac | aggatatgca | gctcgggact | ccagtggcca | cttgtcccct | tacacttaca | 180 |
| atctcagaaa | gaaaggacct | gaggatgtaa | ttgtaaaggt | catttactgc | ggaatctgcc | 240 |
| actctgattt | agttcaaatg | cgtaatgaaa | tggacatgtc | tcattaccca | atggtccctg | 300 |
| ggcatgaagt | ggtggggatt | gtaacagaga | ttggcagcga | ggtgaagaaa | ttcaaagtgg | 360 |
| gagagcatgt | agggggttggt | tgcattgttg | ggtcctgtcg | cagttgcggt | aattgcaatc | 420 |
| agagcatgga | acaatactgc | agcaaggaga | tttggaccta | caatgatgtg | aaccatgacg | 480 |
| gcacacctac | tcagggcgga | tttgcaagca | gtatggtggt | tgatcagatg | tttgtggttc | 540 |
| gaatcccgga | gaatcttcct | ctggaacaag | cggcccctct | gttatgtgca | ggggttacag | 600 |
| ttttcagccc | aatgaagcat | ttcgccatga | cagagcccgg | gaagaaatgt | gggattttgg | 660 |
| gtttaggagg | cgtggggcac | atgggtgtca | agattgccaa | agccttggta | ctccacgtga | 720 |
| cggttatcag | ttcgtctgat | aaaaagaaag | aagaagccat | ggaagtcctc | ggcgccgatg | 780 |
| cttatcttgt | tagcaaggat | actgaaaaga | tgatggaagc | agcagagagc | ctagattaca | 840 |
| taatggacac | cattccagtt | gctcatcctc | tggaaccata | tcttgccctt | ctgaagacaa | 900 |
| atggaaagct | agtgatgctg | ggcgttgttc | cagagccgtt | gcacttcgtg | actcctctct | 960 |
| taatacttgg | gagaaggagc | atagctggaa | gtttcattgg | cagcatggag | gaaacacagg | 1020 |
| aaactctaga | tttctgtgca | gagaagaagg | tatcatcgat | gattgaggtt | gtgggcctgg | 1080 |
| actacatcaa | cacggccatg | gaaaggttgg | agaagaacga | tgtccgttac | agatttgtgg | 1140 |
| tggatgttgc | tagaagcaag | ttggataatt | agtctgcaat | caatcaatca | gatcaatgcc | 1200 |
| tgcatgcaag | atgaatagat | ctggactagt | agcttaacat | gaaagggaaa | ttaaattttt | 1260 |
| atttaggaac | tcgatactgg | ttttttgttac | tttagtttag | cttttgtgag | gttgaaacaa | 1320 |
| ttcagatgtt | tttttaactt | gtatatgtaa | agatcaattt | ctcgtgacag | taaataataa | 1380 |
| tccaatgtct | tctgccaaat | taatatatgt | attcgtattt | ttatatgaaa | aaaaaaaaa | 1440 |
| aaaaaaaaaa | aaaaaaaaaa | aaaaaaaaaa | aaaa | | | 1474 |

<210> SEQ ID NO 72
<211> LENGTH: 1038
<212> TYPE: DNA
<213> ORGANISM: Pinus radiata

<400> SEQUENCE: 72

| | | | | | |
|---|---|---|---|---|---|
| gaattcggca | cgagagaggg | ttatatatct | tgattctgac | ctgattgtcg | tcgacgacat | 60 |
| tgccaagctc | tgggccacgg | atttggaatc | tcgtgtcctc | ggggcaccag | agtactgcaa | 120 |
| ggcgaatttc | acaaagtatt | tcaccgataa | tttctggtgg | gatcccgcat | tatccaagac | 180 |
| ctttgaggga | aaaaaaccct | gctacttcaa | cacaggcgta | atggtgatcg | atcttgaaaa | 240 |
| atggcgggca | ggggaattca | caagaaagat | cgaaatctgg | atggacatac | agaaggaacg | 300 |
| ccgtatctat | gagctcggat | cattaccgcc | atttttactg | gtatttgctg | gtttggttaa | 360 |
| gcaagtcgat | catcgttgga | atcagcacgg | tttaggcgga | gataatttgc | aaggcctttg | 420 |

-continued

```
ccgagatctt caccctggac ctgtcagttt gttgcattgg agtggtaagg gcaaaccttg        480
gctacgcctg gaatgccaag cggacttgcc ctctggatac tttatgggct ccttatgatc        540
tttatcgatc aacgtattac ctaaatgggt gagagagcct ctctcctcgg ggtgcttttt        600
atcgaattaa acctgatttg ataaaatgcc aaatagaact ttacgcctat gcatctttca        660
gttttgaatt tcaattctgg taacgaatag aagaaaacaa tagcacagcc acaggcagga        720
caaatccatc atgagggacc aatcgtttga atttagtatt aataaggttg ttccatataa        780
cgcctgtgaa gaatgatatt gtggactgat ctatttatat ttgtactgcc atgccatcct        840
cagccagcag agaggcaagc aatgccgctg caagtcatgt agggaaggcg ttgtgaactc        900
aattttcggc gactgtacag gatgtaaatt tttggaacat taatatcatt atgataagtt        960
cctgaaccaa caactgtata ataccttata aatgtatctg caactccatt tttgcataaa       1020
aaaaaaaaaa aaaaaaaa                                                     1038

<210> SEQ ID NO 73
<211> LENGTH: 372
<212> TYPE: DNA
<213> ORGANISM: Pinus radiata

<400> SEQUENCE: 73 ctagggtct tggggggttc ctgatgccca attgttgctg tgcttggcat gaacccaaaa         60
catgcaagag atctgtagtc agtagtcttg ttggatctat agcttttaga aaagagtcac       120 gtcctttag ggtaacatca ttccaaccat atccagttcc accaccggct acaccttcaa       180
cgggaggagg agcaagatat tcagcattgc tttgggcacc agatggatag gcattatttt       240
ccatcggaat tcagccgagc tcgcccccctc agtccaatcg tcgtgaaaat ccctcaaaat       300
tgggcaattc tggctcgaaa tcgccaaatt atgggctaca acaggattaa aattgcacag       360
aaatctgcca gt                                                           372

<210> SEQ ID NO 74
<211> LENGTH: 545
<212> TYPE: DNA
<213> ORGANISM: Pinus radiata

<400> SEQUENCE: 74
aaagaattcg gcacgagggc aatccgagcc tagccaacca acttggcagc aaggagcaca        60
gggagttggc gagagaagct gttaggaaat cttttggtatt gttgaaaaat gggaagtcag      120
ccaacaagcc tttgctccct ttggagaaga atgcttccaa ggttcttgtt gcaggaaccc       180
atcctgataa tctgggttat cagtgtggtg gatggacgat ggaatggcaa ggattaagtg       240
gaaacataac cgtaggaact acaattctgg aagctatcaa actagctgtc agcccctcta       300
ctgaagtggt ttatgagcaa aatccagatg ctaactatgt caaaggacaa gggttttcat       360
atgccattgt ggttgtgggt gaggcaccat acgcagaaac gtttggagac aatcttaatt       420
tgaccattcc cctaggcgga ggggacacga ttaagacggt ctgtggctcc ttgaaatgcc       480
ttgtaatctt gatatctgga aggccacttg ttattgaacc ttatcttcca ttggtggatc       540
gtttt                                                                   545

<210> SEQ ID NO 75
<211> LENGTH: 463
<212> TYPE: DNA
<213> ORGANISM: Pinus radiata

<400> SEQUENCE: 75
```

```
gcaggtcgac actagtggat ccaaagaatt cggcacgaga aaaacaaat gttagctagc      60 ctagtgatga gctttacgta tacctggcct tttatacatg gatctgagtt tttatgcagg    120
tgtagagcct tttgttactc tgtatcactg ggacttgcca caagctctgg aggacgaata    180
cggtggattt cgtagcaaaa aagttgtgga tgactttggc atattctcag aagaatgctt    240
tcgtgctttt ggagaccgtg tgaagtactg ggtaactgtt aacgaaccgt tgatcttctc    300
atatttttct tacgatgtgg ggcttcacgc accgggccgc tgttcgcctg gatttggaaa    360
ctgcactgcg ggaaattcag cgacagagcc ttatattgta gcccataaca tgcttcttgc    420
acatagtacc gctgttaaaa atatatagca taaatacccca ggg                     463

<210> SEQ ID NO 76
<211> LENGTH: 435
<212> TYPE: DNA
<213> ORGANISM: Pinus radiata

<400> SEQUENCE: 76
acactagtgg atccaaagaa ttcggcacga ggctaccatc ttccctcata atattgggct     60
tggagctacc agggatcctg atctggctag aagaataggg gctgctacgg ctttggaagt    120
tcgagctact ggcattcaat acacatttgc tccatgtgtt gctgtttgca gagatcctcg    180
atggggccgc tgctatgaga gctacagtga ggatccaaaa attgtcaagg ccatgactga    240
gattatcgtt ggcctgcaag ggaatcctcc tgctaattct acaaaagggg ggccttttat    300
agctggacag tcaaatgttg cagcttgtgc taagcatttt gtgggttatg gtggaacaac    360
caaaggtatc gatgagaata atactgttat caactatcaa gggttatttc aacattccaa    420
attaccccca atttt                                                     435

<210> SEQ ID NO 77
<211> LENGTH: 451
<212> TYPE: DNA
<213> ORGANISM: Pinus radiata

<400> SEQUENCE: 77
gaattcggca cgagcctaga attctatggt gaaaattgtt gggacaaggc tgcccaagtt     60
tacaaaggaa cagtcccaaa tggttaaagg ttcaatagac tatctaggcg ttaaccaata    120
cactgcttat tacatgtatg atcctaaaca acctaaacaa aatgtaacag attaccagac    180
tggactggaa tacaggcttt gcatatgctc gcaatggagt gcctattgga ccaagggcga    240
actccaattg gctttacatt gtgccttggg gtctatacaa ggccgtcaca tacgtaaaag    300
aacactatgg aaatccaact atgattctct ctgaaaatgg aatggacgac ctggaaacgt    360
gacacttcca gcaggactgc atgataccat caggggtaac tactataaaa gctatttgca    420
aaatttgatt aatgcacgtg aatgaccggg g                                   451

<210> SEQ ID NO 78
<211> LENGTH: 374
<212> TYPE: DNA
<213> ORGANISM: Pinus radiata

<400> SEQUENCE: 78
ctgctctgca agcagtacta tgcacagcaa ggcctgctta actgaaaaca gagcgctgag     60
cttgaggaaa cgctcaagca ttgctgaggc caccgtttat ctaaatagcg caacataggg    120
cttcagaaaa atggcaatgg cacaagcatt cagaggccgt gtcttgcaag ctgcccgttt    180
```

-continued

```
gctccgccgc aacattctgc cggaggataa aagctttgga tccgctgctt ctcctagacg    240
agctcttagc ctgctctcat caaaagcctt catctctttc tctgttgaac ggcatcggct    300
agctgctaca aattcaacaa ttgtgttgca atctcgaaac ttttctgcaa aaggtaaaaa    360
gacaggacaa tctg                                                      374
```

```
<210> SEQ ID NO 79
<211> LENGTH: 457
<212> TYPE: DNA
<213> ORGANISM: Pinus radiata

<400> SEQUENCE: 79
gaagaatgga agagattaat ggtgataacg cagtaaggag gagctgcttt cctccaggtt     60
tcatgtttgg gatagcaact tctgcttatc agtgtgaagg agctgccaac gaaggtggaa    120
aaggcccaag catctgggac tcattttcac gaacaccagg caaaattctt gatgaagca    180 acggtgatgt agcagtggat cagtatcatc gttataaggc agatgtaaaa ctgatgaaag    240
atatgggcgt ggctacctac agattctcga tttcatggcc tcgtatattt ccaaagggaa    300
aaggagagat caatgaggaa ggagtagcct attacaataa cctcatcaat gaactcctcc    360
agaatggaat ccaagcgtct gtcaactttg tttcactggg atactcccca gtctctggag    420
gatgaatatg gcggatttct gaggccaacc attgtga                             457
```

```
<210> SEQ ID NO 80
<211> LENGTH: 346
<212> TYPE: DNA
<213> ORGANISM: Pinus radiata

<400> SEQUENCE: 80
ggtgtgatgg caggaattcc agtcctaagg ccattttgca tctgtttgct ttcagtctac     60
atgctgcaca ttgtagctgc agtagcttca ccaaggctag gtagaagcag cttcccaagg    120
ggtttcaaat ttggtgcagg gtcatctgct tatcaggcgg aaggagctgc tcatgagggt    180
ggcaaaggcc caagcatttg ggatacattc tcccacactc caggtaaaat cgctgatggg    240
aatattggga tgttgcagta gatcaatacc accgttataa ggaagatgtg cagcttctca    300
aatacatggg aatggacgtc tatcgtttct ctatctcctg gtcacg                   346
```

```
<210> SEQ ID NO 81
<211> LENGTH: 957
<212> TYPE: DNA
<213> ORGANISM: Pinus radiata

<400> SEQUENCE: 81
gaattcggca cgagaaagcc ctagaatttt ttcagcatgc tatcacagcc ccagcgacaa     60
ctttaactgc aataactgtg gaagcgtaca aaaagtttgt cctagtttct ctcattcaga    120
ctggtcaggt tccagcattt ccaaaataca cacctgctgt tgtccaaaga aatttgaaat    180
cttgcactca gccctacatt gatttagcaa acaactacag tagtgggaaa atttctgtat    240
tggaagcttg tgtcaacacg aacacagaga agttcaagaa tgatagtaat ttgggggttag    300 tcaagcaagt tttgtcatct ctttataaac ggaatattca gagattgaca cagacatatc    360
tgaccctctc tcttcaagac atagcaagta cggtacagtt ggagactgct aagcaggctg    420
aactccatgt tctgcagatg attcaagatg gtgagatttt tgcaaccata aatcagaaag    480
atgggatggt gagcttcaat gaggatcctg aacagtacaa aacatgtcag atgactgaat    540
atatagatac tgcaattcgg agaatcatgg cactatcaaa gaagctcacc acagtagatg    600
```

```
agcagatttc gtgtgatcat tcctacctga gtaaggtggg gagagagcgt tcaagatttg      660
acatagatga ttttgatact gttccccaga agttcacaaa tatgtaacaa atgatgtaaa      720
tcatcttcaa gactcgctta tattcattac tttctatgtg aattgatagt ctgttaacaa      780
tagtactgtg gctgagtcca gaaaggatct ctcggtatta tcacttgaca tgccatcaaa      840
aaaatctcaa atttctcgat gtctagtctt gattttgatt atgaatgcga cttttagttg      900
tgacatttga gcacctcgag tgaactacaa agttgcatgt taaaaaaaaa aaaaaaa       957
```

<210> SEQ ID NO 82
<211> LENGTH: 489
<212> TYPE: DNA
<213> ORGANISM: Pinus radiata

<400> SEQUENCE: 82

```
gcaggtcgac actagtggat ccaaagaatt cggcacgaga taagactaat tttccagaca       60
atcctccatt cccattcaat tacactggta ctccacccaa taatacacag gctgtgaatg      120
ggactagagt aaaagtcctt cccttaaca caactgttca attgattctt caagacacca      180
gcatcttcag cacagacagc caccctgtcc atctccatgg tttcaatttc tttgtggtgg      240
gccaaggtgt tggaaactac aatgaatcaa cagatgcacc aaattttaac ctcattgacc      300
ctgtcgagag aaacactgtg ggagttccca aaggaggttg ggctgctata agatttcgtg      360
cagacaatcc aggggtttgg ttcatgcact gtcatttgga ggttcacaca tcgtggggac      420
tgaaaatggc gtgggtagta aagaacggaa aagggcccat cgattttcca cccgggtggg      480
taccagtaa                                                             489
```

<210> SEQ ID NO 83
<211> LENGTH: 471
<212> TYPE: DNA
<213> ORGANISM: Pinus radiata

<400> SEQUENCE: 83

```
gaattcggca cgagaaaacc ttttcagacg aatgttctga tgctcggccc cggccagaca       60
acagacatac ttctcactgc caatcaggct acaggtagat actacatggc tgctcgagca      120
tattccaacg ggcaaggagt tcccttcgat aacaccacta ccactgccat tttagaatac      180
gagggaagct ctaagacttc aactccagtc atgcctaatc ttccattcta taacgacacc      240
aacagtgcta ctagcttcgc taatggtctt agaagcttgg gctcacacga ccacccagtc      300
ttcgttcctc agagtgtgga ggagaatctg ttctacacca tcggtttggg gttgatcaaa      360
tgtccggggc agtcttgtgg aggtccaacg gatcaagatt tgcagcaagt atgaatacat      420
atcatttgtc ccgcaaccac ttcttccaat ccttcaagct cagcattttg g               471
```

<210> SEQ ID NO 84
<211> LENGTH: 338
<212> TYPE: DNA
<213> ORGANISM: Pinus radiata

<400> SEQUENCE: 84

```
gttcggcact gagagatcca tttctttcaa tgttgagaca gtgagtagta ttagtttgat       60
atctctttca ggaatatatc gtgcttgcag gatctttagt ttctgcaaca atgtcgttgc      120
aatcagtgcg tctatcttct gctctccttg ttttgctact agcatttgtt gcttacttag      180
ttgctgtaac aaacgcagat gtccacaatt ataccttcat tattagaaag agacagttac      240
```

| | | |
|---|---|---|
| caggctatgc aataagcgta taatcgccac cgtcaatggc agctaccagg cccaactatt | 300 |
| catgtacgtg atggagacgt tgttaattat caaagctt | 338 |

<210> SEQ ID NO 85
<211> LENGTH: 1229
<212> TYPE: DNA
<213> ORGANISM: pinus radiata

<400> SEQUENCE: 85

| | | |
|---|---|---|
| agagaaataa ttatatttgt aaatttaagt ctacgtttat taaaaaacta caaccctaaa | 60 |
| tgcaggagaa aaaacaagca tgctgtctac tgaagcttac aaatcaaatc cctgcgatat | 120 |
| gtcttttctc gtgccgaatt cggcacgaga agatcttggt tcgagtctct cagctctctc | 180 |
| caaaggaatt ttgtgggtca tttgcaggtg aagacaccat ggtgaaggct tatcccaccg | 240 |
| taagcgagga gtacaaggct gccattgaca aatgcaagag gaagctccga gctctcattg | 300 |
| cagagaagaa ctgtgcgccg atcatggttc gaatcgcatg gcacagcgct gggacttacg | 360 |
| atgtcaagac caagaccgga gggcccttcg ggacgatgag atatgggggcc gagcttgccc | 420 |
| acggtgctaa cagtggtctg gacatcgcag ttaggctcct ggagccaatc aaggaacagt | 480 |
| tccccataat cacctatgct gacctttatc agttggctgg tgtggtggct gttgaagtga | 540 |
| ccggggggacc tgacattccg ttccatcctg aagagaaga caagcctgag cctccagaag | 600 |
| aaggccgcct tcctgatgct acaaaaggac ctgatcatct gagggatgtt tttggtcaca | 660 |
| tggggttgaa tgataaggaa attgtggcct tgtctggtgc ccacaccttg gggagatgcc | 720 |
| acaaggagag atctggtttt gaaggaccat ggacctctaa ccccccttatc tttgacaact | 780 |
| cttacttcac agagcttgtg actggagaga aggaaggcct gcttcagttg ccatctgata | 840 |
| aggcactgct tgctgatcct agttttgcag tttatgttca gaagtatgca caggacgaag | 900 |
| acgctttctt tgctgactat gcggaagctc acctgaagct ttctgaactt gggtttgctg | 960 |
| atgcgtagat tcataccttc tgcagagaca attccttgct agatagcttc gttttgtatt | 1020 |
| tcatctaatc ttttcgatta tatagtcaca tagaagttgg tgttatgcgc catagtgata | 1080 |
| cttgaaccta catgttttttg aaaagtatcg atgttcttta aaatgaacat tgaatacaac | 1140 |
| attttggaat ctggttgtgt tctatcaagc gcatatttta atcgaatgct tcgttcctgt | 1200 |
| taaaaaaaaa aataaaataa aaaaaaaa | 1229 |

<210> SEQ ID NO 86
<211> LENGTH: 1410
<212> TYPE: DNA
<213> ORGANISM: Pinus radiata

<400> SEQUENCE: 86

| | | |
|---|---|---|
| gaagatgggg ctgtgggtgg tgctggcttt ggcgctcagt gcgcactatt gcagtctcag | 60 |
| gcttacaatg tggtaagttc aagcaatgct actgggagtt acagtgagaa tggattggtg | 120 |
| atgaattact atggggactc ttgccctcag gctgaagaga tcattgctga acaagtacgc | 180 |
| ctgttgtaca aaagacacaa gaacactgca ttctcatggc ttagaaatat tttccatgac | 240 |
| tgtgctgtgg agtcatgtga tgcatcgctt ctgttggact caacaaggaa cagcatatca | 300 |
| gaaaaggaca ctgacaggag cttcggcctc cgcaacttta ggtatttgga taccatcaag | 360 |
| gaagccgtgg agagggagtg ccccgggtc gtttcctgtg cagatatact cgttctctct | 420 |
| gccagagatg gcgttgtatc gttgggagga ccatacattc ccctgaagac gggaagaaga | 480 |
| gatggacgga agagcagagc agatgtggtg gagaattacc tgcccgatca caatgagagc | 540 |

-continued

```
atctccactg ttctgtctcg cttcaaagcc atgggaatcg acacccgtgg ggttgttgca      600
ctgctggggg ctcacagcgt ggggaggact cactgcgtga agctggtgca caggctgtac      660
ccggaagtag atccgacact ggaccctggg cacgtggagc acatgaagca caagtgcccg      720
gacgcgatcc ccaacccgaa ggcagtgcag tatgtgcgga acgaccgggg aacgcctatg      780
aagctggaca caactactac cgtgaacctg atgaacaaca agggctcct aatagtggac       840 cagcaactgt atgcagattc gaggaccagg ccgtatgtga agaagatggc aaaaagccag      900
gaatacttct tcaaatactt ctcccgggcg ctcaccatcc tctctgagaa caatcctctc      960
accggcgctc gaggagaaat ccgtcggcag tgctcgctca aaacaaatt gcacacaaaa      1020 agcaagcgtt gagcgatagc tcaatgccgc agtggtggga gtgatagcgt gatgccacag     1080
tggtgggcat ttcatatata aattgcagtt tgcgttttta ttagataatc ataatggtgt     1140
ggtgtgacta tgccctgcga atcacatcga tgaaccacaa ccgaaccgtg aacagtagg      1200 cttattccct tatgtaagca gaacctttta ttataagcaa aaagacaat cctgtctgtt     1260 attctagtat aattttgtca tcagttaaag ttgctcatct gataataact ggaaacggta     1320
aaatatgaca actacgtatc ttctttggtc atctgataat aaccggaaac gataaaatat     1380
gacaactaca tatattcttt aaaaaaaaaa                                      1410
```

<210> SEQ ID NO 87
<211> LENGTH: 687
<212> TYPE: DNA
<213> ORGANISM: Pinus radiata

<400> SEQUENCE: 87

```
gtagtttcgt tttacaacaa tctcaggttt tgaatctcag aatagttgcg aaaggaagcg       60
atgacgaagt acgtgatcgt tagctccatt gtgtgtttct ttgtatttgt ttctgcgtgc      120
ataatttctg tcaatggatt agttgtccat gaagatgatc tgtcaaagcc tgtgcatggg      180
ctttcgtgga cattttataa ggacagttgc cccgacttgg aggccatagt gaaatcggta      240
cttgagccgg cgttggacga agatatcact caggccgcag gcttgctgag acttcatttc      300
catgactgtt ttgtgcaggg ttgcgatggg tccgtgttgc tgacaggaac taaaagaaac      360
cccagtgagc aacaggctca gccaaactta acactaagag cccgggcctt gcagctgatc      420
gacgaaatta aaaccgctgt agaagctagc tgcagtgggg ttgtaacttg tgcagacatt      480
ctggctttgg ctgctcgtga ctccgtccgc tcaggaggcc caaaatttcc agtaccactt      540
ggccgcagag atagcctaaa gtttgccagt caatccgtag ttctcgccaa tataccaact      600
ccaactttaa atttgacaca gctgatgaac atttttggct ccaaaggatt cagtttggcc      660
gaaatggttg ctcttcaggt ggcacac                                          687
```

<210> SEQ ID NO 88
<211> LENGTH: 688
<212> TYPE: DNA
<213> ORGANISM: Pinus radiata

<400> SEQUENCE: 88

```
gtagtttcgt tttacaacaa tctacaggtt ttgaatctca gaatagttgc gaaaggaagc       60
gatgacgaag tacgtgatcg ttagctccat tgtatgtttc tttgtatttg tttctgcgtg      120
cataatttct gtcaatggat tagttgtcca tgaagatgat ctgtcaaagc ctgtgcatgg      180
gctttcgtgg acattttata aggacagttg ccccgacttg gaggccatag tgaaatcggt      240
```

-continued

| | |
|---|---|
| acttgagccg gcgttggacg aagatatcac tcaggccgca ggttgctgag acttcatttc | 300 |
| catgactgtt ttgtgcaggg ttgcgatggg tccgtgttgc tgacaggaac taaaagaaac | 360 |
| ccccgagtga gcaacaggct cagccaaact taacactaag agcccgggcc ttgcagctga | 420 |
| tcgacgaaat taaaaccgct gtagaagcta gctgcagtgg ggttgtaact tgtgcagaca | 480 |
| ttctggcttt ggctgctcgt gactccgtcg ctcaggaggc ccaaaatttc cagtaccact | 540 |
| tggccgcaga gatagcctaa agtttgccag tcaatccgta gttctcgcca atataccaac | 600 |
| tccaacttta aatttgacac agctgatgaa cattttggc tccaaaggat tcagtttggc | 660 |
| cgaaatggtt gctcttcagg tggcacac | 688 |

<210> SEQ ID NO 89
<211> LENGTH: 278
<212> TYPE: DNA
<213> ORGANISM: Pinus radiata

<400> SEQUENCE: 89

| | |
|---|---|
| tcttcgaatt ctctttcacg actgcttcgt taatggctgc gatggctcga tattgttaga | 60 |
| tgataactca acgttcaccg gagaaaagac tgcaggccca aatgttaatt ctgcgagagg | 120 |
| attcgacgta atagacacca tcaaaactca agttgaggca gcctgcagtg gtgtcgtgtc | 180 |
| atgtgccgac attctcgcca ttgctgcacg cgattcagtc gtccaactgg ggggcccaac | 240 |
| atggacggta cttctgggag aaaagacgga tccgatca | 278 |

<210> SEQ ID NO 90
<211> LENGTH: 1960
<212> TYPE: DNA
<213> ORGANISM: Pinus radiata

<400> SEQUENCE: 90

| | |
|---|---|
| gttttccgcc attttcgcc tgtttctgcg gagaatttga tcaggttcgg attgggattg | 60 |
| aatcaattga aaggtttta ttttcagtat ttcgatcgcc atggccaacg gaatcaagaa | 120 |
| ggtcgagcat ctgtacagat cgaagcttcc cgatatcgag atctccgacc atctgcctct | 180 |
| tcattcgtat tgctttgaga gagtagcgga attcgcagac agaccctgtc tgatcgatgg | 240 |
| ggcgacagac agaacttatt gcttttcaga ggtggaactg atttctcgca aggtcgctgc | 300 |
| cggtctggcg aagctcgggt tgcagcaggg gcaggttgtc atgcttctcc ttccgaattg | 360 |
| catcgaattt gcgtttgtgt tcatggggc ctctgtccgg ggcgccattg tgaccacggc | 420 |
| caatcctttc tacaagccgg gcgagatcgc caaacaggcc aaggccgcgg gcgcgcgcat | 480 |
| catagttacc ctggcagctt atgtggagaa actggccgat ctgcagagcc acgatgtgct | 540 |
| cgtcatcaca atcgatgatg ctcccaagga aggttgccaa catatttccg ttctgaccga | 600 |
| agccgacgaa acccaatgcc cggccgtgac aatccacccg gacgatgtcg tggcgttgcc | 660 |
| ctattcttcc ggaaccacgg ggctccccaa gggcgtgatg ttaacgcaca aaggcctggt | 720 |
| gtccagcgtt gcccagcagg tcgatggtga aaatcccaat ctgtatttcc attccgatga | 780 |
| cgtgatactc tgtgtcttgc ctcttttcca catctattct ctcaattcgg ttctcctctg | 840 |
| cgcgctcaga gccggggctg cgaccctgat tatgcagaaa ttcaacctca cgacctgtct | 900 |
| ggagctgatt cagaaataca aggttaccgt tgccccaatt gtgcctccaa ttgtcctgga | 960 |
| catcacaaag agccccatcg tttcccagta cgatgtctcg gccgtccgga taatcatgtc | 1020 |
| cggcgctgcg cctctcggga aggaactcga agatgccctc agagagcgtt ttcccaaggc | 1080 |
| cattttcggg cagggctacg gcatgacaga agcaggcccg gtgctggcaa tgaacctagc | 1140 |

```
cttcgcaaag aatcctttcc ccgtcaaatc tggctcctgc ggaacagtcg tccggaacgc   1200
tcaaataaag atcctcgata cagaaactgg cgagtctctc ccgcacaatc aagccggcga   1260
aatctgcatc cgcggacccg aaataatgaa aggatatatt aacgacccgg aatccacggc   1320
cgctacaatc gatgaagaag gctggctcca cacaggcgac gtcgggtaca ttgacgatga   1380
cgaagaaatc ttcatagtcg acagagtaaa ggagattatc aaatataagg cttccaggt    1440 ggctcctgct gagctggaag ctttacttgt tgctcatccg tcaatcgctg acgcagcagt   1500
cgttcctcaa aagcacgagg aggcgggcga ggttccggtg gcgttcgtgg tgaagtcgtc   1560
ggaaatcagc gagcaggaaa tcaaggaatt cgtggcaaag caggtgattt tctacaagaa   1620
aatacacaga gtttactttg tggatgcgat tcctaagtcg ccgtccggca agattctgag   1680
aaaggatttg agaagcagac tggcagcaaa atgaaaatga atttccatat gattctaaga   1740
ttcctttgcc gataattata ggattccttt ctgttcactt ctatttatat aataaagtgg   1800
tgcagagtaa gcgccctata aggagagaga gagcttatca attgtatcat atggattgtc   1860
aacgccctac actcttgcga tcgctttcaa tatgcatatt actataaacg atatatgttt   1920
tttttataaa tttactgcac ttctcgttca aaaaaaaaa                          1960
```

<210> SEQ ID NO 91
<211> LENGTH: 701
<212> TYPE: DNA
<213> ORGANISM: Pinus radiata

<400> SEQUENCE: 91

```
gtagtttcgt tttacaacaa tctcaggttt tgaatctcag aatagttgcg aaaggaagcg     60
atgacgaagt acgtgatcgt tagctccatt gtatgtttct ttgtatttgt ttctgcgtgc    120
ataatttctg tcaatggatt agttgtccat gaagatgatc tgtcaaagcc tgtgcatggg    180 cttttcgtgga cattttataa ggacagttgc cccgacttgg aggccatagt gaaatcggta    240
cttgagccgg cgttggacga agatatcact caggccgcag gttgctgaga cttcatttcc    300
atgactgttt tgtgcagggt tgcgatgggt ccgtgttgct gacaggaact aaaagaaacc    360
ccgagtgagc aacaggctca gccaaactta acactaagag cccgggcctt gcagctgatc    420
gacgaaatta aaaccgctgt agaagctagc tgcagtgggg ttgtaacttg tgcagacatt    480
ctggctttgg ctgctcgtga ctccgtcgct caggaggccc aaaatttcca gtaccacttg    540
gccgcagaga tagcctaaag tttgccagtc aatccgtagt tctcgccaat ataccaactc    600
caactttaaa tttgacacag ctgatgaaca tttttggctc caaggattc agtttggccg    660 aaatggttgc tctttcaggt ggacacacaa tcggcattgg t                        701
```

<210> SEQ ID NO 92
<211> LENGTH: 626
<212> TYPE: DNA
<213> ORGANISM: Pinus radiata

<400> SEQUENCE: 92

```
gttgcaggtc gggatgatt tgaatcacag aaacctcagc gattttgcca agaaatatgg     60
caaaatcttt ctgctcaaga tgggccgagg aatcttgtg gtagtttcat ctcccgatct    120
cgccaaggag gtcctgcaca cccagggcgt cgagtttggg tctcgaaccc ggaacgtggt    180
gttcgatatc ttcacgggca aggggcagga catggtgttc accgtctatg gagatcactg    240
gagaaagatg cgcaggatca tgactgtgcc tttctttacg aataaagttg tccagcacta    300
```

-continued

```
cagattcgcg tgggaagacg agatcagccg cgtggtcgcg gatgtgaaat cccgcgccga    360
gtcttccacc tcgggcattg tcatccgtag cgcctccagc tcatgatgta taatattatg    420
tataggatga tgttcgacag gagattcgaa tccgaggacg acccgctttt cctcaagctc    480
aaggccctca acggagagcg aagtcgattg gcccagagct ttgagtacaa ttatggggat    540
ttcattccca gtcttaggcc cttcctcaga ggttatcaca gaatctgcaa tgagattaaa    600
gagaaacggc tctctctttt caagga                                         626
```

<210> SEQ ID NO 93
<211> LENGTH: 660
<212> TYPE: DNA
<213> ORGANISM: Pinus radiata
<220> FEATURE:
<221> NAME/KEY: unsure
<222> LOCATION: (1)...(660)
<223> OTHER INFORMATION: n at all occurrences indicates unsure

<400> SEQUENCE: 93

```
acccagtgac cttcaggcct gagagatttc ttgaggaaga tgttgatatt aagggccatg     60
attacaggct actgccattg gtgcagggcg caggatctgc cctggtgcac aattgggtat    120
taatttagtt cagtctatgt tgggacacct gcttcatcat ttcgtatggg cacctcctga    180
gggaatgaag gcagaagaca tagatctcac agagaatcca gggcttgtta ctttcatggc    240
caagcctgtg caggccattg ctattcctcg attgcctgat catctctaca agcgacagcc    300
actcaattga tcaattgatc tgatagtaag ttttgaatttt gttttgatac aaaacgaaat    360
aacgtgcagt ttctccttt ccatagtcaa catgcagctt tctttctctg aagcgcatgc    420
agctttcttt ctctgaagcc caacttctag caagcaataa ctgtatattt tagaacaaat    480
acctattcct caaattgagw atttctctgt aggggnngnt aattgtgcaa tttgcaagna    540
atagtaaagt ttantttagg gnatttaat agtcctangt aanangnggn aatgntagng    600
ggcattnaga aaccctaat agntgttggn ggnngntagg ntttttnacc aaaaaaaaaa    660
```

<210> SEQ ID NO 94
<211> LENGTH: 1012
<212> TYPE: DNA
<213> ORGANISM: Pinus radiata

<400> SEQUENCE: 94

```
ctttgaggca acctacattc attgaatccc aggatttctt cttgtccaaa caggtttaag     60
gaaatggcag gcacaagtgt tgctgcagca gaggtgaagg ctcagacaac ccaagcagag    120
gagccggtta aggttgtccg ccatcaagaa gtgggacaca aaagtctttt gcagagcgat    180
gccctctatc agtatatatt ggaaacgagc gtgtaccctc gtgagcccga gccaatgaag    240
gagctccgcg aagtgactgc caagcatccc tggaacctca tgactacttc tgccgatgag    300
ggtcaatttc tgggcctcct gctgaagctc attaacgcca agaacaccat ggagattggg    360
gtgtacactg gttactcgct tctcagcaca gcccttgcat gcccgatga tggaaagatt    420 ctagccatgg acatcaacag agagaactat gatatcggat tgcctattat tgagaaagca    480
ggagttgccc acaagattga cttcagagag ggccctgctc tgccagttct ggacgaactg    540
cttaagaatg aggacatgca tggatcgttc gattttgtgt tcgtggatgc ggacaaagac    600
aactatctaa actaccacaa gcgtctgatc gatctggtga aggttggagg tctgattgca    660
tatgacaaca ccctgtggaa cggatctgtg gtggctccac ccgatgctcc cctgaggaaa    720
tatgtgagat attacagaga tttcgtgatg gagctaaaca aggcccttgc tgtcgatccc    780
```

```
cgcattgaga tcagccaaat cccagtcggt gacggcgtca cccttttgcag gcgtgtctat    840 tgaaaacaat ccttgtttct gctcgtctat tgcaagcata aaggctctct gattataagg    900
agaacgctat aatatatggg gttgaagcca tttgttttgt ttagtgtatt gataataaag    960
tagtacagca tatgcaaagt ttgtatcaaa aaaaaaaaaa aaaaaaaaaa aa           1012
```

<210> SEQ ID NO 95
<211> LENGTH: 1460
<212> TYPE: DNA
<213> ORGANISM: Pinus radiata

<400> SEQUENCE: 95

```
aaaacgtcca tagcttcctt gccaactgca agcaatacag tacaagagcc agacgatcga     60
atcctgtgaa gtggttctga agtgatggga agcttggaat ctgaaaaaac tgttacagga    120
tatgcagctc gggactccag tggccacttg tccccttaca cttacaatct cagaaagaaa    180
ggacctgagg atgtaattgt aaaggtcatt tactgcggaa tctgccactc tgatttagtt    240
caaatgcgta atgaaatgga catgtctcat tacccaatgg tccctgggca tgaagtggtg    300
gggattgtaa cagagattgg cagcgaggtg aagaaattca agtgggaga gcatgtaggg    360 gttggttgca ttgttgggtc ctgtcgcagt tgcggtaatt gcaatcagag catggaacaa    420
tactgcagca agaggatttg gacctacaat gatgtgaacc atgacggcac acctactcag    480
ggcggatttg caagcagtat ggtggttgat cagatgtttg tggttcgaat cccggagaat    540
cttcctctgg aacaagcggc ccctctgtta tgtgcagggg ttacagtttt cagcccaatg    600
aagcatttcg ccatgacaga gcccgggaag aaatgtggga ttttgggttt aggaggcgtg    660
gggcacatgg gtgtcaagat tgccaaagcc tttggactcc acgtgacggt tatcagttcg    720
tctgataaaa agaagaaga agccatgaa gtcctcggcg ccgatgctta tcttgttagc    780
aaggatactg aaaagatgat ggaagcagca gagagcctag attacataat ggacaccatt    840
ccagttgctc atcctctgga accatatctt gcccttctga agacaaatgg aaagctagtg    900
atgctgggcg ttgttccaga gccgttgcac ttcgtgactc ctctcttaat acttgggaga    960
aggagcatag ctggaagttt cattggcagc atggaggaaa cacaggaaac tctagatttc    1020
tgtgcagaga agaaggtatc atcgatgatt gaggttgtgg gcctggacta catcaacacg   1080
gccatggaaa ggttggagaa gaacgatgtc cgttacagat ttgtggtgga tgttgctaga   1140
agcaagttgg ataattagtc tgcaatcaat caatcagatc aatgcctgca tgcaagatga   1200
atagatctgg actagtagct taacatgaaa gggaaattaa atttttatttt aggaactcga   1260 tactggtttt tgttacttta gtttagcttt tgtgaggttg aaacaattca gatgtttttt   1320
taacttgtat atgtaaagat caattctctg tgacagtaaa taataatcca atgtcttctg    1380
ccaaattaat atatgtattc gtattttttat atgaaaaaaa aaaaaaaaaa aaaaaaaaa    1440 aaaaaaaaaa aaaaaaaaa                                                 1460
```

<210> SEQ ID NO 96
<211> LENGTH: 788
<212> TYPE: DNA
<213> ORGANISM: Pinus radiata

<400> SEQUENCE: 96

```
ataagactct cgagaaggtc tatgtccccg aggaggggt tctcaactta atcgcagaga     60
caccatttcc agctaatatt ggcatagcaa ttggtcattc tatctttgtc aaggagatc    120
```

-continued

| | |
|---|---|
| aaacaaattt tgaaattgga cctaatggtg tggaggctag tcagctatac ccagatgtga | 180 |
| aatataccac tgtcgatgag tacctcagca aatttgtgtg aagtatgcga gattctcttc | 240 |
| cacatgcttc agagatacat aacagtttca atcaatgttt gtcctaggca tttgccaaat | 300 |
| tgtgggttat aatccttcgt aggtgtttgg cagaacagaa cctcctgttt agtatagtat | 360 |
| gacgagctag gcactgcaga tccttcacac ttttctcttc cataagaaac aaatactcac | 420 |
| ctgtggtttg ttttctttct ttctggaact ttggtatggc aataatgtct ttggaaaccg | 480 |
| cttagtgtgg aatgctaagt actagtgtcc agagttctaa gggagttcca aaatcatggc | 540 |
| tgatgtgaac tggttgttcc agagggtgtt tacaaccaac agttgttcag tgaataattt | 600 |
| tgttagagtg tttagatcca tctttacaag gctattgagt aaggttggtg ttagtgaacg | 660 |
| gaatgatgtc aaatcttgat gggctgactg actctcttgt gatgtcaaat cttgatggat | 720 |
| tgtgtctttt tcaatggtaa aaaaaaaaaa aaaaaaaaaa aaaaaaaaaa aaaaaaaaaa | 780 |
| aaaaaaaa | 788 |

<210> SEQ ID NO 97
<211> LENGTH: 577
<212> TYPE: DNA
<213> ORGANISM: Pinus radiata

<400> SEQUENCE: 97

| | |
|---|---|
| gcccgacggc cacttgttgg acgccatgga agctctccgg aaagccggga ttctggaacc | 60 |
| gtttaaactg cagcccaagg aaggactggc tctcgtcaac ggcacagcgg tgggatccgc | 120 |
| cgtggccgcg tccgtctgtt ttgacgccaa cgtgctgggc gtgctggctg agattctgtc | 180 |
| tgcgctcttc tgcgaggtga tgcaaggaa accggagttc gtagatccgt taacccacca | 240 |
| gttgaagcac cacccagggc agatcgaagc cgcggccgtc atggagttcc tcctcgacgg | 300 |
| tagcgactac gtgaaagaag cagcgcggct tcacgagaaa gacccgttga gcaaaccgaa | 360 |
| acaagaccgc tacgctctgc gaacatcgcc acagtggttg gggcctccga tcgaagtcat | 420 |
| ccgcgctgct actcactcca tcgagcggga gatcaattcc gtcaacgaca atccgttaat | 480 |
| cgatgtctcc agggacatgg ctctccacgg cggcaacttc cagggaacac ccatcggagt | 540 |
| ttccatggac aacatgcgaa tctctttggc agccgtc | 577 |

<210> SEQ ID NO 98
<211> LENGTH: 492
<212> TYPE: DNA
<213> ORGANISM: Pinus radiata

<400> SEQUENCE: 98

| | |
|---|---|
| tacctggcca accccgtcac gactcacgtc cagagcgccg aacaacacaa ccaggatgtc | 60 |
| aattccctcg gcttgatctc cgccagaaag actgccgagg ccgttgagat tttaaagctg | 120 |
| atgttcgcta catatctggt ggccttatgc caggcgatcg atctccggca cctggaagaa | 180 |
| aacatgcgat ccgttgtgaa gcacgtagtc ttgcaggccg caagaaagac actgtgcact | 240 |
| gcagaagacg gaagcctcca cgacaccgga ttttgcgaga aggagctcct gcaagtcatc | 300 |
| gatcatcagc ccgtttttctc gtacatcgac gatcccacaa atccatcata cgcgcttatg | 360 |
| ctccaactca gagaagtgct cgtagatgag gctctcaaat catcttgccc agacgggaat | 420 |
| gacgaatccg atcacaattt gcagcccgct gagagcgctg gagctgctgg aatattaccc | 480 |
| aattgggtgt tt | 492 |

<210> SEQ ID NO 99
<211> LENGTH: 391
<212> TYPE: DNA
<213> ORGANISM: Pinus radiata

<400> SEQUENCE: 99

| | | | | | | |
|---|---|---|---|---|---|---|
| cgttttccca | aaggccattt | tcgggcaggg | ctacggcgca | tgacagaagc | aggcccggtg | 60 |
| ctggcaatga | acctagcctt | cgcaaagaat | cctttccccg | ccaaatctgg | ctcctgcgga | 120 |
| acagtcgtcc | ggaacgctca | aataaagatc | ctcgattaca | ggaactggcg | agtctctccc | 180 |
| gcacaatcaa | gccggcgaaa | tctgcatccg | cggacccgaa | ataatgaaag | gatatattaa | 240 |
| cgacccggaa | tccacggccg | ctacaatcga | tgaagaaggc | tggctccaca | caggcgacgt | 300 |
| cgggtacatt | gacgatgacg | aagaaatctt | catagtcgac | agagtaaagg | agattatcaa | 360 |
| tataaaggct | tccaggtgga | tcctgctaat | c | | | 391 |

<210> SEQ ID NO 100
<211> LENGTH: 567
<212> TYPE: DNA
<213> ORGANISM: Eucalyptus grandis

<400> SEQUENCE: 100

| | | | | | | |
|---|---|---|---|---|---|---|
| ctgaattttc | cctaactaga | aataaagaga | ttatatacat | acacgagcaa | agcgctctcc | 60 |
| tccagttgtc | ttccttcgtt | cgctcatctc | tcctcgtaca | ttattagcat | acgacctctt | 120 |
| gtatcggacc | cggatccgct | atcgttaacg | tacacacgtt | ctagtgctga | atggagatgg | 180 |
| agagcaccac | cggcaccggc | aacggccttc | acagcctctg | cgccgccggg | agccaccatg | 240 |
| ccgacccact | gaactggggg | gcggcggcag | cagccctcac | agggagccac | ctcgacgagg | 300 |
| tgaagcggat | ggtcgaggag | taccggaggc | cggcggtgcg | cctcggcggg | gagtccctca | 360 |
| cgatagccca | ggtggcggcg | gtggcgagtc | aggaggggt | aggggtcgag | ctctcggagg | 420 |
| cggcccgtcc | cagggtcaag | gccagcagcg | actgggtcat | ggagagcatg | aacaagggaa | 480 |
| ctgacagcta | cggggtcaca | ccgggttcgg | cggcaacttc | tcaaccggag | gccgaagcaa | 540 |
| ggcggtcctt | ttcagaagga | acttata | | | | 567 |

<210> SEQ ID NO 101
<211> LENGTH: 612
<212> TYPE: DNA
<213> ORGANISM: Eucalyptus grandis

<400> SEQUENCE: 101

| | | | | | | |
|---|---|---|---|---|---|---|
| aaagcaacac | attgaactct | ctctctctct | ctctctctct | ctctctctct | cccccacccc | 60 |
| cccttcccaa | ccccacccac | atacagacaa | gtagatacgc | gcacacagaa | gaagaaaaga | 120 |
| tgggggtttc | aatgcagtca | atcgcactag | cgacggttct | ggccgtccta | acgacatggg | 180 |
| cgtggagggc | ggtgaactgg | gtgtggctga | ggccgaagag | gctcgagagg | cttctgagac | 240 |
| agcaaggtct | ctccggcaag | tcctacacct | tcctggtcgg | cgacctcaag | gagaacttgc | 300 |
| ggatgctcaa | ggaagccaag | tccaagccca | tcgccgtctc | cgatgacatc | aagcctcgtc | 360 |
| tcttgccttt | cttgcatcaa | tccttccaaa | cctatggcaa | agactcgttc | acatggatgg | 420 |
| gcccaacacc | aagagtgaac | attacgaacc | cggaacaaat | aaaggaggta | ttctctaaga | 480 |
| tatatgacta | tcccaagcca | gcctccaatc | ccctggtgaa | gttgctcgct | gatggactcg | 540 |
| cgaaccatga | gggcgagaaa | tgggctcggc | accgaaagat | tatcaatcca | gcattccaca | 600 |
| tggagaagtt | ga | | | | | 612 |

<210> SEQ ID NO 102
<211> LENGTH: 455
<212> TYPE: DNA
<213> ORGANISM: Eucalyptus grandis

<400> SEQUENCE: 102

```
tgtctctctc tctctctctc tctgtaaacc accatgctct tcctcactca tctcctagca      60
gttctagggg ttgtgttgct cctgctaatt ctatggaggg caagatcttc tccgaacaaa     120
cccaaaggta ctgccttacc cccggagctg ccgggcgcat ggccgatcat aggccacatc     180
cacttgctgg gcggcgagac cccgctggcc aggaccctgg ccgccatggc ggacaagcag     240
ggcccgatgt ttcggatccg tctcggagtc cacccggcga ccatcataag cagccgtgag     300
gcggtccggg agtgcttcac cacccacgac aaggacctcg cttctcgccc caaatccaag     360
gcgggaatcc acttgggcta cgggtatgcc ggttttggct tcgtagaata cggggacttt     420
tggcgcgaga tgaggaagat caccatgctc gagct                                 455
```

<210> SEQ ID NO 103
<211> LENGTH: 1866
<212> TYPE: DNA
<213> ORGANISM: Eucalyptus grandis

<400> SEQUENCE: 103

```
cgggctcgtg gctcggctcc ggcgcaagcc gcccttccca ccgggcccga ggggcctccc      60
ggtcatcggg aacatgctca tgatgggcga gctcacccac cgcggcctcg cgagtctggc     120
gaagaagtat ggcgggatct tccacctccg catgggcttc ctgcacatgg ttgccgtgtc     180
gtcccccgac gtgcccgcc aggtcctcca ggtccacgag gggatcttct cgaaccggcc     240
tgccaccatc gcgatcagct acctcacgta tgaccgggcc gacatggcct tcgcgcacta     300
cggcccgttc tggcggcaga tgcggaagct gtgcgtgatg aagctcttca gccggaagcg     360
ggctgagtcg tgggagtcgg tccgcgatga ggtggacacg atggtgcgca ccgtcgcggg     420
cagcgagggg accgccgtga acatcggcga gctcgtgttc gagctcacgc gggacatcat     480
ctaccgcgcg gccttcgcac gagctcgacc gagggccagg acgagttcat cagcatactg     540
caggagttct cgaaattatt tggcgccttc aacatagccg attttatccc gtacctgagc     600
tggatcgatc cgcaagggct caccgccagg cttgtcaagg cgcgccagtc gctggacggg     660
ttcatcgacc acattataga tgatcacatg gacaagaaga gaaacaagac gagttccggt     720
ggaggcgatc aagatgtcga taccgacatg gtcgacgatc tgctggcctt ctacagcgac     780
gaagcgaagg tgaacgagtc cgacgatttg cagaactcga tcaggctaac gagagacaac     840
atcaaggcca tcatcatgga cgtgatgttc ggcgggacgg agactgtggc gtcggctatc     900
gagtgggcca tggcggagct catgcgaagc cccgaggacc tgaagaaggt ccagcaagaa     960
ctcgcggatg tcgtgggcct agaccggaga gtcgaggaga gcgacttcga aagctgacc     1020
tatctcaagt gctgcctcaa agagaccctc cgcctccacc cgccgatccc gctgctcctc     1080
cacgagacgg cagaggacgc cgtgatctcc ggctaccgca tccccgcacg gtcccgggtc     1140
atgatcaatg catgggccat cggcgtgac cccggctcgt ggaccgaacc tgacaagttc     1200
aaaccgtccc ggttcctgga gtcaggcatg cccgactaca aggggagcaa cttcgagttc     1260
atccctttcg ggtcgggccg gaggtcgtgc caggggatgc agctcgggct ctacgcgctc     1320
gacatggccg tggcccacct cctgcactgc ttcacgtggg aactgccga cgggatgaag     1380
ccgagcgaga tggacatggg cgacgtcttc gggctcaccg cgccgaggtc cacccggctc     1440
```

```
gtggcggtgc cgactccgag gttggtgggg gctctatatt gagcaagcaa atggagggtc    1500
gggttggggg gtgcgaggag gggaacgtat ttttcagctc ctggagggct gcaagatttg    1560
gagtgcataa acccatccat acaagggcaa agagggtgg tgccaaaatg atttgcatgg     1620
atttttcgat ttttgttttg tattataaaa aaggtcaaat aaccgaagag acaagaaag     1680 acaagaaaaa gaattgagac ggaacttgaa tcaatgttgt tctgttctct ctttctattt    1740
ctttgtggat attacaagac ttatctcatt tggtgggctt ttcttttctt gtgatttctt    1800
tgatcttgtc atacacaaat aaatatggaa tgaagaaacc tttccatcaa aaaaaaaaa     1860 aaaaaa                                                               1866
```

<210> SEQ ID NO 104
<211> LENGTH: 519
<212> TYPE: DNA
<213> ORGANISM: Eucalyptus grandis

<400> SEQUENCE: 104

```
cacgagctcg tgagccttcc cggagacaag gccatcttac ttcgcaacaa attgcgtccg     60
cactcctttc tcaagaaacc tagtcatcca agaagcagag cattgcaact gcaaacagcc    120
aaagcccaaa ctcgtacaga aggagagaga gagagagaat agaagcatga gtgcatgcac    180
gaaccaagca atcacgacgg ccagtgaaga tgaagagttc ttgttcgcca tggaaatgaa    240
tgctctgata gcactcccct tggtcttgaa ggccaccatc gaactgggga tcctcgaaat    300
actggccgag tgcgggccta tggctccact ttcgcctgct cagattgcct cccgtctctc    360
cgcaaagaac ccggaagccc ccgtaaccct tgaccggatc ctccggtttc tcgccagcta    420
ctccatcctc tcttgcactc tcgcccaaga cacagaaggc aaccccctga ggctttacgg    480
tttgggaccc aaaagcaaac acttcgtcag agcccatgg                           519
```

<210> SEQ ID NO 105
<211> LENGTH: 594
<212> TYPE: DNA
<213> ORGANISM: Eucalyptus grandis

<400> SEQUENCE: 105

```
ccaaccctgg accaggtact tttggcaggc ggtccattgc ccttcaaacc ggtccaaacc     60
ggaccatcac tgtccttata tacgttgcat catgcctgct catagaactt aggtcaactg    120
caacatttct tgatcacaac atattacaat attcctaagc agagagagag agagagagag    180
agagagagag agagagagag tttgaatcaa tggccaccgc cggagaggag agccagaccc    240
aagccgggag gcaccaggag gttggccaca agtctctcct tcagagtgat gctctttacc    300
aatatatttt ggagaccagc gtgtacccaa gagagcctga gcccatgaag gagctcaggg    360
aaataacagc aaaacatcca tggaacataa tgacaacatc agcagacgaa gggcagttct    420
tgaacatgct tctcaagctc atcaacgcca agaacaccat ggagattggt gtcttcactg    480
gctactctct cctcgccacc gctcttgctc ttcctgatga cggaaagatt ttggctatgg    540
acattaacag agagagctat gaacttggcc tgccggtcat ccaaaaagcc ggtg           594
```

<210> SEQ ID NO 106
<211> LENGTH: 407
<212> TYPE: DNA
<213> ORGANISM: Eucalyptus grandis

<400> SEQUENCE: 106

```
ccgtttttatt tcctctgatt tcctttgctc gagtctcgcg gaagagagag aagagaggag       60
aggagagaat gggttcgacc ggatccgaga cccagatgac cccgacccaa gtctcggacg      120
aggaggcgaa cctcttcgcc atgcagctgg cgagcgcctc cgtgctcccc atggtcctca      180
aggccgccat cgagctcgac ctcctcgaga tcatggccaa ggccgggccg ggcgcgttcc      240
tctccccggg ggaagtcgcg gcccagctcc gacccagaa ccccgaggca cccgtaatgc       300
tcgaccggat cttccggctg ctggccagct actccgtgct cacgtgcacc ctccgcgacc      360
tccccgatgg caaggtcgag cggctctacg gcttagcgcc ggtgtgc                   407

<210> SEQ ID NO 107
<211> LENGTH: 1630
<212> TYPE: DNA
<213> ORGANISM: Eucalyptus grandis

<400> SEQUENCE: 107 ccgtttttatt tcctctgctt tcctttgctc gagtctcgcg gaagagagag aagagaggag      60
aggagagaat gggttcgacc ggatccgaga cccagatgac cccgacccaa gtctcggacg      120
aggaggcgaa cctcttcgcc atgcagctgg cgagcgcctc cgtgctcccc atggtcctca      180
aggccgccat cgagctcgac ctcctcgaga tcatggccaa ggccgggccg ggcgcgttcc      240
tctccccggg ggaagtcgcg gcccagctcc gacccagaa ccccgaggca cccgtcatgc       300
tcgaccggat cttccggctg ctggccagct actccgtgct cacgtgcacc ctccgcgacc      360
tccccgatgg caaggtcgag cggctctacg gcttagcgcc ggtgtgcaag ttcttggtca      420
agaacgagga cggggtctcc atcgccgcac tcaacttgat gaaccaggac aaaatcctca      480
tggaaagctg gtattacctg aaagatgcgg tccttgaagg cggaatccca ttcaacaagg      540
cgtacgggat gaccgcgttc gagtatcatg gcaccgaccc gcgattcaac aagatctttta    600 accggggaat gtctgatcac tccaccatta ctatgaagaa gatactggaa acatacaagg      660
gcttcgaggg cctcgagacc gtggtcgatg tcggaggcgg cactggggcc gtgctcagca      720
tgatcgttgc caaatcccca tcgatgaaag ggatcaactt cgacctgcct cacgtgattg      780
aagacgctcc acccttcct ggtgtcaagc acgtcggagg cgacatgttc gtcagcgttc       840
caaagggaga tgccattttc atgaagtgga tatgccatga ctggagtgac gaccattgcg      900
cgaagttcct caagaactgc tacgatgcgc ttcccaacaa tggaaaggtg atcgttgcag      960
agtgcgtact ccctgtgtac ccagacacga gcctagcgac caagaatgtg atccacatcg     1020
actgcatcat gttggcccac aacccaggcg ggaaagagag gacacagaag gagttcgagg     1080
cattggccaa aggggccgga tttcagggct tccaagtcat gtgctgcgct ttcggcactc     1140
acgtcatgga gttcctgaag accgcttgat ctgctcctct gtggtgatgt tcatggttct     1200
tggatttgaa aggtcgtgaa ggagccctt tctcacagtt ggcttcggca taccaagttc      1260
ttctcataaa aggaaacaat aagaagcgac tgtatgatgg cgcaagtgga agttacaaga     1320
tttgttgttt tatgtctata aagttttgag tcttctgcat actgatttca cagaatgtgt     1380
aacgaaacgg cgtatatgga tgtgcctgaa tgatggaaat tgtgatattc tgtcttcttt     1440
ttcagtaaat cacttcgaac aaaagttgtg ttgctcgtgg caaccaggaa aaaatctgtg     1500
ggtgactttg agtaaaagcc tgtcattcac aaaccccatg gcattgcctt tggtcagggg     1560
tcagccaagc cggaagcgtc aacgtgaaaa gatcctcaag ggtccattaa aatccccaca     1620
aacccagagc                                                             1630
```

<210> SEQ ID NO 108
<211> LENGTH: 1248
<212> TYPE: DNA
<213> ORGANISM: Eucalyptus grandis

<400> SEQUENCE: 108

| | | | | | |
|---|---|---|---|---|---|
| atcactaacc | atctgccttt | cttcatcttc | tttcttctgc | ttctcctccg | tttcctcgtt | 60 |
| tcgatatcgt | gaaaggagtc | cgtcgacgac | aatggccgag | aagagcaagg | tcctgatcat | 120 |
| cggagggacg | ggctacatcg | gcaagttcat | cgtggaagcg | agtgcaaaag | cagggcatcc | 180 |
| cacgttcgcg | ctggttaggc | agagcacggt | ctccgacccc | gtcaagggcc | agctcgtcga | 240 |
| gagcttcaag | aacttgggcg | tcactctgct | catcggtgat | ctgtacgatc | atgagagctt | 300 |
| ggtgaaggca | atcaagcaag | ccgacgtggt | gatatcgaca | gtggggcaca | tgcaaatggc | 360 |
| ggatcagacc | aagatcgtcg | acgccattaa | ggaagctggc | aacgttaaga | gattctttcc | 420 |
| ttccgaattc | ggcaatgatg | tggacagggt | gcatgctgtg | gagccagcga | agtctgcttt | 480 |
| tgaattgaag | gcccagatcc | gccgtgccgt | ggaggcggca | ggcatccctt | acacctacgt | 540 |
| cccatgtggc | tgcttcgccg | gctacttcct | cccaacactg | gcgcagcagg | aggtcactgc | 600 |
| tcctccgaag | gacaaagtca | ccgtcatggg | tgacggaaat | gcaaaggcaa | ttttcaacaa | 660 |
| ggaagatgac | attgcggcct | tcaccatcaa | ggctgtggat | gatccgagat | cgctgaacaa | 720 |
| gatcctttac | atcaggcctc | ctaagaacgt | ttactcattc | aatgagcttg | ttgccttgtg | 780 |
| ggagaagaaa | attggcaaga | ccctcgagaa | gatttacctt | cctgaagagc | aaatcctgaa | 840 |
| gcaaatccag | gagtccccaa | ttcccatcaa | tgtcatatta | gcagtgaacc | attcaatctt | 900 |
| tgttaagggc | gacggtgcca | attttgagat | cgaggagtct | tttggtgtcg | aggcttctga | 960 |
| gctgtaccca | gatgtgaagt | acactacagt | ggaagaatac | ctcgaaaatt | ttgtctaaat | 1020 |
| taaggccatg | cgtctcctgt | tcttcaagga | gtgagttacc | gtgactctgg | tggacagtcg | 1080 |
| atatgtatta | aaaggctgta | cacctaaaga | atatcaaagg | tcacggtctt | atttagaatt | 1140 |
| gtctctgatg | tcatattctt | cttggtcttc | ttggacatgt | atttgctttc | ctttgccgtg | 1200 |
| gtatccatga | atttcccagg | ttgttgaaat | taaaaaaaaa | aaaaaaaa | | 1248 |

<210> SEQ ID NO 109
<211> LENGTH: 481
<212> TYPE: DNA
<213> ORGANISM: Eucalyptus grandis

<400> SEQUENCE: 109

| | | | | | |
|---|---|---|---|---|---|
| gttaatggca | gtgcagcctc | aacaccaccc | accttcctcc | atctctctcc | tcccttcttc | 60 |
| tttctctgac | ttcaatggca | gccgactcca | tgcttgcgtt | cagtataaga | ggaaggtggg | 120 |
| gcagcctaaa | ggggcactgc | gggtcactgc | atcaagcaat | aagaagatcc | tcatcatggg | 180 |
| aggcacccgt | tcatcggtg | tgttttgtc | gagactactg | tcaaagaag | gtcatcaggt | 240 |
| cactttgttt | accagaggaa | aagcacccat | cactcaacaa | ttgcctggtg | agtcggacaa | 300 |
| ggacttcgct | gatttttcat | ccaagatcct | gcatttgaaa | ggagacagaa | aggatttga | 360 |
| ttttgttaaa | tctagtcttg | ctgcagaagg | ctttgacgtt | gtttatgaca | ttaacggcga | 420 |
| gaggcggatg | aagtcgcacc | aattttggat | gcctgccaaa | ccttgaacca | gtcaactact | 480 |
| g | | | | | | 481 |

<210> SEQ ID NO 110
<211> LENGTH: 458
<212> TYPE: DNA

-continued

<213> ORGANISM: Eucalyptus grandis

<400> SEQUENCE: 110

| cataagctct | cccgtaatcc | tcacatcaca | tggcgaagag | caaggtcctc | gtcgttggcg | 60 |
| gcactggcta | cctcgggcgg | aggttcgtga | gggcgagcct | ggaccagggc | caccccacgt | 120 |
| acgtcctcca | gcgtccggag | accggcctcg | acattgagaa | gctccagacg | ctactgcgct | 180 |
| tcaagaggcg | tggcgcccaa | ctcgtcgagg | cctcgttctc | agacctgagg | agcctcgtcg | 240 |
| acgctgtgag | gcgggtcgat | gtcgtcgtct | gtgccatgtc | gggggtccac | ttccggagcc | 300 |
| acaacatcct | gatgcagctc | aagctcgtgg | aggctatcaa | agaagctgga | aatgtcaagc | 360 |
| ggtttttgcc | gtcagagttc | ggaatggacc | cggccctcat | gggtcatgca | attgagccgg | 420 |
| gaagggtcac | gttcgatgag | aaatggaggt | gagaaaag | | | 458 |

<210> SEQ ID NO 111
<211> LENGTH: 448
<212> TYPE: DNA
<213> ORGANISM: Eucalyptus grandis

<400> SEQUENCE: 111

| aggaggcacc | tcctcgaaac | gaagaagaag | aaggacgaag | gacgaaggag | acgaaggcga | 60 |
| gaatgagcgc | ggcgggcggt | gccgggaagg | tcgtgtgcgt | gaccggggcg | tccggttaca | 120 |
| tcgcctcgtg | gctcgtcaag | ctcctcctcc | agcgcggcta | caccgtcaag | gccaccgtcc | 180 |
| gcgatccgaa | tgatccaaaa | aagactgaac | atttgcttgg | acttgatgga | gcgaaagata | 240 |
| gacttcaact | gttcaaagca | aacctgctgg | aagagggttc | atttgatcct | attgttgagg | 300 |
| gttgtgcagg | cgttttcac | actgcctctc | ccttttatca | tgatgtcaag | gatccgcagg | 360 |
| cagaattact | tgatccggct | gtgaagggaa | cactcaatgt | cctgaagtca | tgttccaaag | 420 |
| accttctctg | cagcgtgtgg | cttgacat | | | | 448 |

<210> SEQ ID NO 112
<211> LENGTH: 578
<212> TYPE: DNA
<213> ORGANISM: Eucalyptus grandis

<400> SEQUENCE: 112

| gttgaacctc | ccgtcctcgg | ctctgctcgg | ctcgtcaccc | tcttcgcgct | cccgcatact | 60 |
| ccaccaccgc | gtacagaaga | tgagctcgga | gggtggggaag | gaggattgcc | tcggttgggc | 120 |
| tgcccgggac | ccttctgggt | tcctctcccc | ctacaaattc | acccgcaggg | ccgtgggaag | 180 |
| cgaagacgtc | tcgattaaga | tcacgcactg | tggagtgtgc | tacgcagatg | tggcttggac | 240 |
| taggaatgtg | cagggacact | ccaagtatcc | tctggtgcca | gggcacgaga | tagttggaat | 300 |
| tgtgaaacag | gttggctcca | gtgtccaacg | cttcaaagtt | ggcgatcatg | tgggggtggg | 360 |
| aacttatgtc | aattcatgca | gagagtgcga | gtattgcaat | gacaggctag | aagtccaatg | 420 |
| tgaaaagtcg | gttatgactt | ttgatggaat | tgatgcagat | ggtacagtga | caaagggagg | 480 |
| atattctagt | cacattgtcg | tccatgaaag | gtattgcgtc | aggattccag | aaaactaccc | 540 |
| gatggatcta | gcagcgcatt | tgctctgtgc | tggatcac | | | 578 |

<210> SEQ ID NO 113
<211> LENGTH: 454
<212> TYPE: DNA
<213> ORGANISM: Eucalyptus grandis

<400> SEQUENCE: 113

```
aactcatctt gaaatgtcat tggagtcatc atcctctagt gagaagaaac aaatgggttc      60
cgccggattc gaatcggcca caaagccgca cgccgttttgc attccctacc ctgcacaaag   120
ccacattggc gccatgctca agctagcaaa gctcctccat cacaagggct tccacatctc   180
cttcgtcaac accgagttca accaccggcg gctcgccagg gctcgaggcc ccgagttcac   240
aaatggaatg ctgagcgact ttcagttcct gacaatcccc gatggtcttc ctccttcgga   300
cttggatgcg atccaagaca tcaagatgct ctgcgaatcg tccaggaact atatggtcag   360
ccccatcaac gatcttgtat cgagcctggg ctcgaacccg agcgtccctc cggtgacttg   420
catcaatctc ggatggtttc atgacactcg tgac                                454
```

<210> SEQ ID NO 114
<211> LENGTH: 479
<212> TYPE: DNA
<213> ORGANISM: Eucalyptus grandis

<400> SEQUENCE: 114

```
catgattgag ggaatcaagg actcttcagg actcatcctg aacacatttg aagatctcga      60
gcagcccgct ctttctttac tccgccaaga agatccaatc gcagttttcg caattggccc   120
attacacaaa tgcggtccat cttcatcggg aagtctcttg gcagaagacc ggagttgcat   180
ttcctggctg acaagcaag cccctaactc agtggtctat gtgagtttg ggagcatcgc    240
ctctgtgaac gagtcggaat tttccgaaat agctttaggt ttagccgata gccagcagcc   300
attcttgtgg gtggttcgac ccgggtcagt gagcggctcg gaactcttag agaatttgcc   360
cggttgcttt ctggaggcat tacaggagag ggggaagatt gtgaaatggg cgcctcaaca   420
tgaagtgctg gctcatcggg gtgtcggagc gttttggact cacaatggat ggaactcca    479
```

<210> SEQ ID NO 115
<211> LENGTH: 420
<212> TYPE: DNA
<213> ORGANISM: Eucalyptus grandis

<400> SEQUENCE: 115

```
caacattgtg tttagagaga ggagagagaa ggcaaacacg cccgttttcg ttttactaag      60
agaagatggt gagcgttgtg gctggtagag tcgagagctt gtcgagcagt ggcattcagt   120
cgatcccgca ggagtatgtg aggccgaagg aggagctcac aagcattggc gacatcttcg   180
aggaggagaa gaagcatgag ggccctcagg tcccgaccat cgacctcgag gacatagcgt   240
ctaaagaccc cgtggtgagg gagaggtgcc acgaggagct caggaaggct gccaccgact   300
ggggcgtcat gcacctcgtc aaccatggga tccccaacga cctgattgag cgtgtcaaga   360
aggctggcga ggtgttcttc aacctcccga tcgaggagaa ggagaagcat gccaacgacc   420
```

<210> SEQ ID NO 116
<211> LENGTH: 679
<212> TYPE: DNA
<213> ORGANISM: Eucalyptus grandis

<400> SEQUENCE: 116

```
ctaagagagg agaggagagg agcaagatgg cactagcagg agctgcactg tcaggaaccg      60
tggtgagctc cccctttgtg aggatgcagc ctgtgaacag actcagggca ttccccaatg   120
tgggtcaggc cctgtttggt gtcaactctg gccgtggcag agtgactgcc atggccgctt   180
acaaggtcac cctgctcacc cctgaaggca agtcgaact cgacgtcccc gacgatgttt   240
```

-continued

| | |
|---|---|
| acatcttgga ctacgccgag gagcaaggca tcgacttgcc ctactcctgc cgtgccggct | 300 |
| cttgctcctc ctgcgcgggc aaggtcgtgg cggggagcgt cgaccagagc gacggcagct | 360 |
| tcctggatga tgatcagatt gaggaaggtt gggtcctcac ttgtgtcgcc tacctaagt | 420 |
| ctgaggtcac cattgagacc cacaaggaag aggagctcac tgcttgaagc tctcctatat | 480 |
| ttgcttttgc ataaatcagt ctcactctac gcaactttct ccactctctc ccccttcac | 540 |
| tacatgtttg ttagttcctt tagtctcttc ctttttact gtacgaggga tgatttgatg | 600 |
| ttattctgag tctaatgtaa tggcttttct ttttcctatt tctgtatgag gaaataaaac | 660 |
| tcatgctcta aaaaaaaaa | 679 |

<210> SEQ ID NO 117
<211> LENGTH: 763
<212> TYPE: DNA
<213> ORGANISM: Eucalyptus grandis

<400> SEQUENCE: 117

| | |
|---|---|
| catacaacta cactgcgacg ccgccgcaga acgcgagcgt gccgaccatg aacggcacca | 60 |
| aggtctaccg gttgccgtat aacgctacgg tccagctcgt tttacaggac accgggataa | 120 |
| tcgcgccgga gacccacccc atccatctgc acggattcaa cttcttcggt gtgggcaaag | 180 |
| gagtggggaa ttatgaccca agaaggatc ccaagaagtt caatctggtt gacccagtgg | 240 |
| agaggaacac cattgaatc ccatctggtg gatggatagc catcagattc acagcagaca | 300 |
| atccaggagt ttggttcctg cactgccatc tggaagtgca cacaacttgg ggactgaaga | 360 |
| tggcattctt ggtggacaat gggaaggggc ctaagagac cctgcttcca cctccaagtg | 420 |
| atcttccaaa atgttgatca tttgatcatg aggacgacaa gcgattacta atgacaccaa | 480 |
| gttagtggaa tcttctcttt gaaaagaag aagaagagca agaagaataa gaaagatgag | 540 |
| gagagaagcc atagaagatt tgaccaagaa gagagaggga aataaaccaa agagacccctt | 600 |
| gagatcacga catcccgcaa ttgtttctag agtaatagaa ggatttactc cgacactgct | 660 |
| acaataaatt aaggaagaca aggaatttgg tttttttcat tggaggagtg taatttgttt | 720 |
| tttggcaagc tcatcacatg aatcacatgg aaaaaaaaa aaa | 763 |

<210> SEQ ID NO 118
<211> LENGTH: 538
<212> TYPE: DNA
<213> ORGANISM: Eucalyptus grandis

<400> SEQUENCE: 118

| | |
|---|---|
| atcaagagtt tgagtctaaa ccttgtctaa tcctctctcg catagtcatt tggagacgaa | 60 |
| gtgctgatcg gccgcagctg cattctcttc gtaaaacatg acggctgtcg gcaaaacctc | 120 |
| tttcctcttg ggagctctcc tcctcttctc tgtggcggtg acattggcag atgcaaaagt | 180 |
| ttactaccat gattttgtcg ttcaagcgac caaggtgaag aggctgtgca cgacccacaa | 240 |
| caccatcacg gtgaacgggc aattcccggg tccgactttg gaagttaacg acggcgacac | 300 |
| cctcgttgtc aatgtcgtca acaaagctcg ctacaacgtc accattcact ggcacggcgt | 360 |
| ccggcaggtg agatctggtt gggccgatgg gccggaattt gtgactcaat gcccgattag | 420 |
| acccggcgga agttacacgt accgtttcac catccaagga caggtaggaa cgctgtggtg | 480 |
| gcatgcacat agctcttggc taagagcgac tgtgtatggt gctctggcat tcgtccaa | 538 |

<210> SEQ ID NO 119
<211> LENGTH: 515

```
<212> TYPE: DNA
<213> ORGANISM: Eucalyptus grandis

<400> SEQUENCE: 119
ctctctctct ctctctctct gtgtgttcat tctcgttgag ctcgtggtcg cctcccgcca      60
tggatccgca caagtaccgt ccatccagtg ctttcaacac ttctttctgg actacgaact     120
ctggtgctcc tgtctggaac aataactctt cgttgactgt tggaagcaga ggtccaattc     180
ttcttgagga ttatcacctc gtggagaaac ttgccaactt tgatagggag aggattccag     240
agcgtgtggt gcatgccaga ggagccagtg caaagggatt ctttgaggtc actcatgaca     300
tttcccagct tacctgtgct gatttccttc gggcaccagg agttcaaaca cccgtgattg     360
tccgtttctc cactgtcatc cacgaaaggg gcagccctga aaccctgagg gaccctcgag     420
gttttgctgt gaagttctac acaagagagg gtaactttga tctggtggga aacaatttcc     480
ctgtcttctt tgtccgtaat gggataaatt ccccg                                515

<210> SEQ ID NO 120
<211> LENGTH: 458
<212> TYPE: DNA
<213> ORGANISM: Eucalyptus grandis

<400> SEQUENCE: 120
gctccctctc gtactgccat actcctgggc cgggattcgg atagggtttt gcggcgatcc      60
atttctcgat tcaaggggaa gaatcatggg gaagtcctac ccgaccgtga gcgaggagta     120
caagaaggct gtcgagaaat gcaagaagaa gttgagaggc ctcatcgctg agaagagctg     180
cgctccgctc atgctccgca tcgcgtggca ctccgccggt accttcgatg tgaagacgaa     240
gaccggaggc ccgttcggga ccatgaagca cgccgcggag ctcagccacg gggccaacag     300
cgggctcgac gttgccgatc aggtcttgca gccgatcaag gatcagttcc ccgtcatcac     360
ttatgctgat ttctaccagc tggctggcgt cgttgctgtg gaagttactg gtggacctga     420
agttgctttt cacccaggaa gagaggcaaa ccacaacc                             458

<210> SEQ ID NO 121
<211> LENGTH: 1243
<212> TYPE: DNA
<213> ORGANISM: Eucalyptus grandis

<400> SEQUENCE: 121
ctcccacttc tgtctcgcca ccattactag cttcaaagcc cagatctcag tttcgtgctc      60
tcttcgtcat ctctgcctct tgccatggat ccgtacaagt atcgcccgtc cagcgcttac     120
gattccagct tttggacaac caactacggt gctcccgtct ggaacaatga ctcatcgctg     180
actgttggaa ctagaggtcc gattctcctg gaggactacc atctgattga gaaacttgcc     240
aacttcgaga gagagaggat tcctgagcgg gtggtccatg cacggggagc cagcgcgaaa     300
gggttcttcg aggtcaccca cgacatctct cacttgacct gtgctgattt cctccgggct     360
cctggagtcc agacgcccgt catcgtccgt ttctccaccg tcatccacga gcgcggcagc     420
cccgaaaccc tcagggaccc tcgtggtttt gcagtgaagt tctacaccag agagggaaac     480
tttgatctgg tggggaacaa tttcccagtc ttcttcgttc gcgatgcaat gaaattcccg     540
gacgcgatcc atgcgttcaa gccgaacccg aagtctaaca tccaggagat gtggagaatc     600
atcgatttct ctcccacca gcccgagagt ctgtccacgt tcgcgtggtt cttcgatgat     660
gtgggcattc ctcaggacta caggcacatg gagggattcg gtgtgcacgc tttcaccttc     720
```

```
atcaacaaga ccggaaagac gaattacgtt aaattccact ggaagccaac ttgcggggtg      780
aagtgcttgc tggaggagga ggcgatcctc attggaggat cgaaccacag ccatgcgacc      840
aaggatcttt atgactcgat cgctgctggc aactacccgg agtggaagct ctacatccaa      900
gtgatggatc cwgctcttga agacagcttc gacttcgatc cgctggatat gacgaaggaa      960
tggcctgagg acatcttgcc tctgcaacca gtaggccgct tggtgctgaa caaaaacgtc     1020
gataacttct cgctgagaa tgagcagcta gcgtttaacc cagcatttgt ggtccctggc      1080
atctattact ccaatgataa gcttctccaa gctaggattt cgcctattc tgatactcac      1140 cgatatcgcc ttggaccaaa ctaccttcaa ctccccgtta atgtcccaag tgcgtcatca     1200
caacaaccac catgatggtt tcatgaatat catgcacagg gat                        1243
```

<210> SEQ ID NO 122
<211> LENGTH: 404
<212> TYPE: DNA
<213> ORGANISM: Pinus radiata

<400> SEQUENCE: 122

```
gacaaggtca taggccctct cttcaaatgc ttggatgggt ggaaaggaac tcctggccca       60
ttctgaaata aataatcttc caagatcgcc tttatacaac gactgctatg atttgagtcc      120
tcggatcttt tgttgatgc agttgtttac cgatctggaa tttgattggt cataaagctt      180
gattttgttt ttctttcttt tgttttatac tgctggattt gcatcccatt ggatttgcca      240
gaaatatgta agggtggcag atcatttggg tgatctgaaa catgtaaaag tggcggatca      300
tttgggtagc atgcagatca gttgggtgat cgtgtactgc tttcactatt acttacatat      360
ttaaagatcg ggaataaaaa catgatttta attgaaaaaa aaaa                       404
```

<210> SEQ ID NO 123
<211> LENGTH: 415
<212> TYPE: DNA
<213> ORGANISM: Pinus radiata

<400> SEQUENCE: 123

```
caaggaagaa aatatggttg cagcagcaga aattacgcag gccaatgaag ttcaagttaa       60
aagcactggg ctgtgcacgg acttcggctc gtctggcagc gatccactga actgggttcg      120
agcagccaag gccatggaag gaagtcactt tgaagaagtg aaagcgatgg tggattcgta      180
tttgggagcc aaggagattt ccattgaagg gaaatctctg acaatctcag acgttgctgc      240
cgttgctcga agatcgcaag tgaaagtgaa attggatgct gcggctgcca aatctagggt      300
cgaggagagt tcaaactggg ttctcaccca gatgaccaag gggacggata cctatggtgt      360
cactactggt ttcggagcca cttctcacag gagaacgaac cagggagccg agctt          415
```

<210> SEQ ID NO 124
<211> LENGTH: 1659
<212> TYPE: DNA
<213> ORGANISM: Pinus radiata

<400> SEQUENCE: 124

```
gttgcaggtc ggggatgatt tgaatcacag aaacctcagc gattttgcca agaaatatgg       60
caaaatcttt ctgctcaaga tgggccagag gaatcttgtg gtagtttcat ctcccgatct      120
cgccaaggag gtcctgcaca cccagggcgt cgagtttggg tctcgaaccc ggaacgtggt      180
gttcgatatc ttcacgggca aggggcagga catggtgttc accgtctatg agatcactg       240 gagaaagatg cgcaggatca tgactgtgcc tttctttacg aataaagttg tccagcacta      300
```

```
cagattcgcg tgggaagacg agatcagccg cgtggtcgcg gatgtgaaat cccgcgccga      360
gtcttccacc tcgggcattg tcatccgtag gcgcctccag ctcatgatgt ataatattat      420
gtataggatg atgttcgaca ggagattcga atccgaggac gacccgcttt tcctcaagct      480
caaggccctc aacggagagc gaagtcgatt ggcccagagc tttgagtaca attatgggga      540
tttcattccc attcttaggc ccttcctcag aggttatctc agaatctgca atgagattaa      600
agagaaacgg ctctctcttt tcaaggacta cttcgtggaa gagcgcaaga agctcaacag      660
taccaagact agtaccaaca ccggggagct caagtgtgca atggaccata ttttagatgc      720
tcaggacaag ggagagatca atgaggataa tgttttgtac atcgttgaga acatcaacgt      780
tgcagcaatt gagacaacgc tgtggtcgat ggaatgggga atagcggagc tggtgaacca      840
ccaggacatt cagagcaagg tgcgcgcaga gctggacgct gttcttggac caggcgtgca      900
gataacggaa ccagacacga caaggttgcc ctaccttcag gcggttgtga aggaaaccct      960
tcgtctccgc atggcgatcc cgttgctcgt ccccacatg aatctccacg acgccaagct      1020
cgggggctac gatattccgg cagagagcaa gatcctggtg aacgcctggt ggttggccaa      1080
caaccccgcc aactggaaga accccgagga gttccgcccc gagcggttct cgaggagga      1140 gaagcacacc gaagccaatg caacgactt caaattcctg ccttgcggtg tggggaggag      1200
gagctgcccg ggaatcattc tggcgctgcc tctcctcgca ctctccatcg gaagacttgt      1260
tcagaacttc caccttctgc cgccgcccgg gcagagcaaa gtggatgtca ctgagaaggg      1320
cgggcagttc agccttcaca ttctcaacca ttctctcatc gtcgccaagc ccatagcttc      1380
tgcttaatcc caacttgtca gtgactggta tataaatgcg cgcacctgaa caaaaaacac      1440
tccatctatc atgactgtgt gtgcgtgtcc actgtcgagt ctactaagag ctcatagcac      1500
ttcaaaagtt tgctaggatt tcaataacag acaccgtcaa ttatgtcatg tttcaataaa      1560
agtttgcata aattaaatga tatttcaata tactattttg actctccacc aattggggaa      1620
ttttactgct aaaaaaaaaa aaaaaaaaaa aaaaaaaa                              1659
```

<210> SEQ ID NO 125
<211> LENGTH: 461
<212> TYPE: DNA
<213> ORGANISM: Pinus radiata

<400> SEQUENCE: 125

```
atttccatgg cgattccgtt tggcttcaat tcgtttcctc tggctgtcct cgtcctcgtt       60
ttccttgttc ttcctccgac tttttctctg gaagatatgg cgtaatagga acctgccgcc      120 aggaccccg gcatggccga tcgtagggaa cgtccttcag attggatttt ccagcggcgc      180
gttcgagacc tcagtgaaga aattccatga gagatacggt ccaatattca ctgtgtggct      240
cggttcccgc cctctgctga tgatcaccga ccgcgagctt gcccacgagg cgctcgtaca      300
gaagggctcc gtcttcgctt gaccgcccgc ccgccctcgg gatgcagaaa atcttcagta      360
gcaaccagca caacatcact tcggctgaat acgcccgct gtggcggagc ttcgcaggaa      420
tctggttaaa gaagccctga gacttcggcg atgaaggctt t                          461
```

<210> SEQ ID NO 126
<211> LENGTH: 569
<212> TYPE: DNA
<213> ORGANISM: Pinus radiata

<400> SEQUENCE: 126

-continued

| | |
|---|---|
| acccagtgac cttcaggcct gagagatttc ttgaggaaga tgttgatatt aagggccatg | 60 |
| attacaggct actgccattc ggtgcagggc gcaggatctg ccctggtgca caattgggta | 120 |
| ttaatttagt tcagtctatg ttgggacacc tgcttcatca tttcgtatgg gcacctcctg | 180 |
| agggaatgaa ggcagaagac atagatctca cagagaatcc agggcttgtt actttcatgg | 240 |
| ccaagcctgt gcaggccatt gctattcctc gattgcctga tcatctctac aagcgacagc | 300 |
| cactcaattg atcaattgat ctgatagtaa gtttgaattt tgttttgata caaaacgaaa | 360 |
| taacgtgcag tttctccttt tccatagtca acatgcagct ttctttctct gaagcgcatg | 420 |
| cagctttctt tctctgaagc ccaacttcta gcaagcaata actgtatatt ttagaacaaa | 480 |
| tacctattcc tcaaattgag tatttctctg taggcgatgt tcacttgtgc aatttgcaag | 540 |
| atatagtaaa gtttactcta aaaaaaaaa | 569 |

<210> SEQ ID NO 127
<211> LENGTH: 661
<212> TYPE: DNA
<213> ORGANISM: Pinus radiata

<400> SEQUENCE: 127

| | |
|---|---|
| gttttatctg aaggacgctg tgcttgaagg ctcccagcca ttcaccaaag cccatggaat | 60 |
| gaatgcgttc gagtacccgg ccatcgatca gagattcaac aagattttca acagggctat | 120 |
| gtctgagaat tctaccatgt tgatgaacaa gattttggat acttacgagg gttttaagga | 180 |
| ggttcaggag ttggtggatg tgggaggagg tattgggtcg actctcaatc tcatagtgtc | 240 |
| taggtatccc cacatttcag gaatcaactt cgacttgtcc catgtgctgg ccgatgctcc | 300 |
| tcactaccca gctgtgaaac atgtgggtgg agacatgttt gatagtgtac caagtggcca | 360 |
| agctattttt atgaagtgga ttctgcatga ttggagcgat gatcattgca ggaagctttt | 420 |
| gaagaattgt cacaaggcgt tgccagagaa ggggaaggtg attgcggtgg acaccattct | 480 |
| cccagtggct gcagagacat ctccttatgc tcgtcaggga tttcatacag atttactgat | 540 |
| gttggcatac aacccagggg gcaaggaacg cacagagcaa gaatttcaag atttagctaa | 600 |
| ggagacggga tttgcaggtg gtgttgaacc tgtatgttgt gtcaatggaa tgtgggtaat | 660 |
| g | 661 |

<210> SEQ ID NO 128
<211> LENGTH: 427
<212> TYPE: DNA
<213> ORGANISM: Pinus radiata

<400> SEQUENCE: 128

| | |
|---|---|
| aatttttctg tggtaagcat atctatggct caaaccagag agaaggacga tgtcagcata | 60 |
| acaaactcca aaggattggt atgcgtgaca ggagcggctg gttacttggc atcttggctt | 120 |
| atcaagcgtc tcctccagtg tggttaccaa gtgagaggaa ctgtgcggga tcctggcaat | 180 |
| gagaaaaaga tggctcattt atggaagtta gatgggcgaa agagagact gcaactaatg | 240 |
| aaagctgatt taatggacga gggcagcttc gatgaggtca tcagaggctg ccatggtgtt | 300 |
| tttcacacag cgtctccagt cgtgggtgtc aaatcagatc ccaagatatg gtatgctctg | 360 |
| gccaagactt tagcagaaaa agcagcatgg gattttgccc aagaaaacca tctggacatg | 420 |
| gttgcag | 427 |

<210> SEQ ID NO 129
<211> LENGTH: 1412

<212> TYPE: DNA
<213> ORGANISM: Pinus radiata

<400> SEQUENCE: 129

```
gaaaacatca tccaggcatt ttggaaattt agctcgccgg ttgattcagg atcctgcaat      60
ggcttttggc gaagagcaga ctgccttgcc acaagaaacg cctttgaatc ctccggtcca     120
tcgaggaaca gtgtgcgtta caggagctgc tgggttcata gggtcatggc tcatcatgcg     180
attgcttgag cgaggatata gtgttagagc aactgtgcga gacactggta atcctgtaaa     240
gacaaagcat ctgttggatc tgccggggc aaatgagaga ttgactctct ggaaagcaga     300
tttggatgat gaaggaagct ttgatgctgc cattgatggg tgtgagggtg ttttccatgt     360
tgccactccc atggatttcg agtccgagga tcccgagaat gagataatta agccaacaat     420
caacggggtc ttgaatgtta tgagatcgtg tgcaaaagcc aagtccgtga agcgagttgt     480
tttcacgtca tctgctggga ctgtgaattt tacagatgat ttccaaacac caggcaaagt     540
ttttgacgaa tcatgctgga ccaacgtgga tctttgcaga aaagttaaaa tgacaggatg     600
gatgtacttt gtatcgaaga cattagcaga gaaagctgct tgggattttg cagaggagaa     660
caagatcgat ctcattactg ttatccccac attggtcgtt ggaccattca ttatgcagac     720
catgccaccg agcatgatca cagccttggc actgttaacg cggaatgaac cccactacat     780
gatactgaga caggtacagc tggttcactt ggatgatctc tgtatgtcac atatctttgt     840
atatgaacat cctgaagcaa agggcagata catctcttcc acatgtgatg ctaccattgt     900
ccaagtggcc aagatgctgg ctcagaaata cccagagtac aatgtaccaa ccacgttcaa     960
ggatgcggat gagtccctgc cggccgtgcc attttcgtca aagaagctcc ttgatttggg    1020
cttcaagttc aactacacca tggaagagat gtttgatggg gccattaagt gctgcagaga    1080
gaaaggattg ctgcctgaga aagcatcttt ctgataagta tctactgatg cagcatacac    1140
acaccgttgg catgtgtggt ttgtgtaaga catggtggca gtggagaaat aatggatcaa    1200
atttggttta tagaaaacag caggaattac tacttgcaag agtgacttat gtgacatgat    1260
atagaaataa gaagaatacc ggctgatcgc tgttgtttat taatgcgaat tttattgatg    1320
ttgacaaggt cataccaggg ctcctggaat gctacatatg tacggctgat tctagctcca    1380
gtaatataat ttttcaaatt ctaaaaaaaa aa                                   1412
```

<210> SEQ ID NO 130
<211> LENGTH: 666
<212> TYPE: DNA
<213> ORGANISM: Pinus radiata

<400> SEQUENCE: 130

```
atcaattttt gcatattatt aaaaagtaag tgtattcgtt ctctatattg atcagtcaca      60
gagtcatggc cagttgtggt tccgagaaag taagagggtt gaatggagat gaagcatgcg     120
aagagaacaa gagagtggtt tgtgtaactg gggcaaatgg gtacatcggc tcttggctgg     180
tcatgagatt actggaacat ggctattatg ttcatggaac tgttagggac ccagaagaca     240
cagggaaggt tgggcatttg ctgcggctcc caggggcaag tgagaagcta agctgttca     300
aggcagagct taacgacgaa atggccttg atgatgctgt gagcggttgt caggggttt     360
tccacgttgc caagcctgtt aatctggact caaacgctct tcaggggag ttgttggtc     420
ctgcggtgag gggaacagta atctgcttc gagcctgcga acgatcgggc actgtgaaac     480
gagtgataca tacctcgtcc gtttcagcag tgagattcac tgggaaacct gaccccctg     540
```

| | |
|---|---|
| atactgtgct ggatgaatct cattggactt cggtcgagta ttgcagaaag acaaagatgg | 600 |
| tcggatggat gtactacatc gccaacactt atgcagaaga gggagcccat aagttcggat | 660 |
| cagaga | 666 |

<210> SEQ ID NO 131
<211> LENGTH: 478
<212> TYPE: DNA
<213> ORGANISM: Pinus radiata

<400> SEQUENCE: 131

| | |
|---|---|
| gctggttcaa gtgtcagccc aatggcctcc cctacagaga atccccagat ttcagaagag | 60 |
| ctgctaaatc atgagatcca tcaaggaagt acagtatgtg tgacaggagc tgctggcttc | 120 |
| ataggatcat ggctcgtcat gcgtttgctt gagcgaggat atactgttag aggaactgtg | 180 |
| cgagacactg gtaatccggt gaagacgaag catctattgg atctgcctgg ggcgaatgag | 240 |
| aggttaactc tctggaaagc agatttggat gatgaaggaa gctttgacgc cgccattgat | 300 |
| ggttgtgagg gagttttcca tgttgccact cccatggatt ttgaatccga gaccccgag | 360 |
| aacgagataa ttaaacccgc tgtcaatggg atgttgaatg ttttgagatc gtgtgggaaa | 420 |
| accaagtcta tgaagcgagt tgttttcacg tcgtctgctg ggactctgct ttttacgg | 478 |

<210> SEQ ID NO 132
<211> LENGTH: 510
<212> TYPE: DNA
<213> ORGANISM: Pinus radiata

<400> SEQUENCE: 132

| | |
|---|---|
| cttgttcaaa gtcacatatc ttattttctt tgtgatatct gcaatttcca agcttttcgt | 60 |
| ctacctccct gaaaagatga gcgaggtatg cgtgacagga ggcacaggct tcatagctgc | 120 |
| ttatctcatt cgtagtcttc tccagaaagg ttacagagtt cgcactacag ttcgcaaccc | 180 |
| agataatgtg gagaagttta gttatctgtg ggatctgcct ggtgcaaacg aaagactcaa | 240 |
| catcgtgaga gcagatttgc tagaggaagg cagttttgat gcagcagtag atggtgtaga | 300 |
| tggagtattc catactgcat cacctgtctt agtcccatat aacgagcgct tgaaggaaac | 360 |
| cctaatagat cctttgtgtga aggcactat caatgtcctc aggtcctgtt caagatcacc | 420 |
| ttcagtaaag cgggtggtgc ttacatcctc ctgctcatca ataccgatac gactataata | 480 |
| gcttagagcg ttccctgctg gactgagtca | 510 |

<210> SEQ ID NO 133
<211> LENGTH: 890
<212> TYPE: DNA
<213> ORGANISM: Pinus radiata

<400> SEQUENCE: 133

| | |
|---|---|
| tcctaattgt tcgatcctcc cttttaaagc ccttcctgg ccttcattcc aggtcacaga | 60 |
| gttgttcatg cagtgctagc aggaggagca gcgttgcaat tggggaaaat tccaaaatca | 120 |
| ataacgagag gacagaagta agtttgtgga aatagcaacc atgccggtgt ttccttctgg | 180 |
| tctggacccc tctgaggaca atggcaagct cgtttgtgtc atggatgcgt ccagttatgt | 240 |
| aggtttgtgg attgttcagg gccttcttca acgaggctat tcagtgcatg ccacggtgca | 300 |
| gagagacgct ggcgaggttg agtctctcag aaaattgcat ggggatcgat tgcagatctt | 360 |
| ctatgcagat gtcttggatt atcacagcat tactgatgcg ctcaagggct gttctggtct | 420 |
| gtctataccct tgagcaccc tcagagtgct gcaggctatg atgaagtgat ggcagaaatt | 480 |

```
gaagtacaag cagcccacaa tgcactggaa gcgtgtgctc agactgagac cattgagaaa      540
gttgtgttca cttcttctgt ggctgcagca atttggagag aagatggaga ctacaaggtt      600
aatgcccttg acgagaggca ttggagtgat gcaaatcttt gcaggaaatt gaagttgtgg      660
tacgcattag ccaagacact gtcagagaag gctgcatggg cgctggcaat ggacagaggg      720
ttgaatatgg tgacaatcaa cgcatctctg attgtaggac ctggcatcac atacaaaagc      780
tcaggatcta ccattgcata tcttaaaggg gctgcacaaa tgtatgagaa gggcacttta      840
gctagtgtgg acataaggtt tctagcggat gcacatatat gcgcttatga              890
```

<210> SEQ ID NO 134
<211> LENGTH: 955
<212> TYPE: DNA
<213> ORGANISM: Pinus radiata

<400> SEQUENCE: 134

```
aatcactgac cttcacatat ttattccaat tctaatatct ctactcgctg tctacctgat       60
ttttcagtgg cgaaccaact tgacagggtt ggacatggcc aacagcagca agattctgat      120
tattggagga acaggctaca ttggtcgtca tataaccaaa gccagccttg ctcttggtca      180
tcccacattc cttcttgtca gagagacctc cgcttctaat cctgagaagg ctaagcttct      240
ggaatccttc aaggcctcag gtgctattat actccatgga tctttggagg accatgcaag      300
tcttgtggag gcaatcaaga agttgatgt agttatctcg gctgtcaagg accacagct       360 gacggatcaa cagaatatta tcaaggctat taaggaggtt ggaaccatca gaggttttt      420 gccatctgag ttcgggaatg acgttgatag aacccatgca gtggagcctg caaagaccat      480
gtttgctacc aaagcgaaaa ttcgcagggc cattgaggca gaaggcatcc cttacacatt      540
tgtctctagc aactgttttg ctgggttgtt cttgccaagt ttggggcagc caggccttac      600
cgccccgcca agggataaag ttgtgatatc tggagatgga aatgccaaag ttgttttgt       660 gaaggaggag gatataggga cattcaccat caaggcagtg gatgacccta gaactctaaa      720
caagatcctg tatttgaggc ttcctgccaa cacatattct cttaacgagc ttgtagctgt      780
gtgggagaag aagattggca agtctctgga gaagacctat ataccagagg aagaggtcct      840
gaaaaaaatt gcagagtcgc cattcccact caatgctata atgtcaaccg gccactctat      900
ttttgtgaaa ggggatcaaa caaattttga aatcggacct gatggtgtgg aggct          955
```

<210> SEQ ID NO 135
<211> LENGTH: 1024
<212> TYPE: DNA
<213> ORGANISM: Pinus radiata

<400> SEQUENCE: 135

```
agagggttat atatcttgat tctgacctga ttgtcgtcga cgacattgcc aagctctggg       60
ccacggattt ggaatctcgt gtcctcgggg caccagagta ctgcaaggcg aatttcacaa      120
agtatttcac cgataatttc tggtgggatc ccgcattatc caagaccttt gagggaaaaa      180
aaccctgcta cttcaacaca ggcgtaatgg tgatcgatct tgaaaatgg cgggcagggg      240 aattcacaag aaagatcgaa atctggatgg acatacagaa ggaacgccgt atctatgagc      300
tcggatcatt accgccattt ttactggtat ttgctggttt ggttaagcaa gtcgatcatc      360
gttggaatca gcacggtttta ggcggagata atttgcaagg cctttgccga gatcttcacc      420
ctggacctgt cagtttgttg cattggagtg gtaagggcaa accttggcta cgcctggaat      480
```

```
gccaagcgga cttgccctct ggatacttta tgggctcctt atgatcttta tcgatcaacg    540
tattacctaa atgggtgaga gagcctctct cctcggggtg cttttatcg aattaaacct     600 gatttgataa aatgccaaat agaactttac gcctatgcat ctttcagttt tgaatttcaa    660
ttctggtaac gaatagaaga aaacaatagc acagccacag gcaggacaaa tccatcatga    720
gggaccaatc gtttgaattt agtattaata aggttgttcc atataacgcc tgtgaagaat    780
gatattgtgg actgatctat ttatatttgt actgccatgc catcctcagc cagcagagag    840
gcaagcaatg ccgctgcaag tcatgtaggg aaggcgttgt gaactcaatt ttcggcgact    900
gtacaggatg taaatttttg gaacattaat atcattatga taagttcctg aaccaacaac    960
tgtataatac cttataaatg tatctgcaac tccatttttg cataaaaaaa aaaaaaaaaa   1020
aaaa                                                                1024
```

<210> SEQ ID NO 136
<211> LENGTH: 497
<212> TYPE: DNA
<213> ORGANISM: Pinus radiata

<400> SEQUENCE: 136

```
agaacataaa tccgaacaat gaacttgcaa atttcctgca ttgccatcgc cagcccaaga     60
aacttttggc cgcaaagcaa tctgtacact ttctctctca ttccttgcta caagcatgga    120
tataggttct aggggtcttg ggggctcctg atgcccaatt gttgctgtgc ttggcatgac    180
ccaaacatgc aagagatctg tagtcagtag tcttgttgga tctatagctt ttagaaaaga    240
gtcacgtcct tttagggtaa catcattcca accatatcca gttccaccac cggctacacc    300
ttcaacggga ggaggagcaa gatattcagc attgctttgg gcaccagatg gataggcatt    360
attttccatc ggaattcagc cgagctcgcc ccctcagtcc aatcgtcgtg aaaatccctc    420
aaaattgggc aattctggct cgaaatcgcc aaattatggg ctacaacagg attaaaattg    480
cacagaaatc tgccagt                                                   497
```

<210> SEQ ID NO 137
<211> LENGTH: 528
<212> TYPE: DNA
<213> ORGANISM: Pinus radiata

<400> SEQUENCE: 137

```
ggcaatccga gcctagccaa ccaacttggc agcaaggagc acaggagtt ggcgagagaa      60 gctgttagga aatctttggt attgttgaaa atgggaagt cagccaacaa gcctttgctc      120
cctttggaga agaatgcttc caaggttctt gttgcaggaa cccatcctga taatctgggt     180
tatcagtgtg gtggatggac gatggaatgg caaggattaa gtggaaacat aaccgtagga     240
actacaattc tggaagctat caaactagct gtcagcccct ctactgaagt ggtttatgag     300
caaaatccag atgctaacta tgtcaaagga caagggtttt catatgccat tgtggttgtg     360
ggtgaggcac catacgcaga aacgtttgga gacaatctta atttgaccat tcccctaggc     420
ggaggggaca cgattaagac ggtctgtggc tccttgaaat gccttgtaat cttgatatct     480
ggaaggccac ttgttattga accttatctt ccattggtgg atcgttttt                 528
```

<210> SEQ ID NO 138
<211> LENGTH: 424
<212> TYPE: DNA
<213> ORGANISM: Pinus radiata

<400> SEQUENCE: 138

```
aaaaaacaaa tgttagctag cctagtgatg agctttacgt atacctggcc ttttatacat    60
ggatctgagt ttttatgcag gtgtagagcc ttttgttact ctgtatcact gggacttgcc   120
acaagctctg gaggacgaat acgtggatt tcgtagcaaa aaagttgtgg atgactttgg    180
catattctca gaagaatgct ttcgtgcttt tggagaccgt gtgaagtact gggtaactgt   240
taacgaaccg ttgatcttct catatttttc ttacgatgtg gggcttcacg caccgggccg   300
ctgttcgcct ggatttggaa actgcactgc gggaaattca gcgacagagc cttatattgt   360
agcccataac atgcttcttg cacatagtac cgctgttaaa aatatatagc ataaatacccc  420 aggg                                                                424

<210> SEQ ID NO 139
<211> LENGTH: 404
<212> TYPE: DNA
<213> ORGANISM: Pinus radiata

<400> SEQUENCE: 139
gctaccatct tccctcataa tattgggctt ggagctacca gggatcctga tctggctaga    60
agaatagggg ctgctacggc tttggaagtt cgagctactg gcattcaata cacatttgct   120
ccatgtgttg ctgtttgcag agatcctcga tggggccgct gctatgagag ctacagtgag   180
gatccaaaaa ttgtcaaggc catgactgag attatcgttg gcctgcaagg gaatcctcct   240
gctaattcta caaaagggg gccttttata gctggacagt caaatgttgc agcttgtgct   300
aagcattttg tgggttatgg tggaacaacc aaaggtatcg atgagaataa tactgttatc   360
aactatcaag ggttatttca acattccaaa ttaccccccaa tttt                  404

<210> SEQ ID NO 140
<211> LENGTH: 437
<212> TYPE: DNA
<213> ORGANISM: Pinus radiata

<400> SEQUENCE: 140
cctagaattc tatggtgaaa attgttggga caaggctgcc caagtttaca aggaacagt     60 cccaaatggt taaaggttca atagactatc taggcgttaa ccaatacact gcttattaca   120
tgtatgatcc taaacaacct aaacaaaatg taacagatta ccagactgga ctggaataca   180
ggctttgcat atgctcgcaa tggagtgcct attggaccaa gggcgaactc caattggctt   240
tacattgtgc ctgggggtct atacaaggcc gtcacatacg taaaagaaca ctatggaaat   300
ccaactatga ttctctctga aaatggaatg gacgacctgg aaacgtgaca cttccagcag   360
gactgcatga taccatcagg ggtaactact ataaaagcta tttgcaaaat ttgattaatg   420
cacgtgaatg accgggg                                                 437

<210> SEQ ID NO 141
<211> LENGTH: 470
<212> TYPE: DNA
<213> ORGANISM: Pinus radiata

<400> SEQUENCE: 141
gatacatcca agctgagaat ggaagagatt aatggtgata acgcagtaag gaggagctgc    60
tttcctccag gtttcatgtt tgggatagca acttctgctt atcagtgtga aggagctgcc   120
aacgaaggtg gaaaaggccc aagcatctgg gactcatttt cacgaacacc aggcaaaatt   180
cttgatggaa gcaacggtga tgtagcagtg gatcagtatc atcgttataa ggcagatgta   240
```

```
aaactgatga aagatatggg cgtggctacc tacagattct cgatttcatg gcctcgtata      300
tttccaaagg gaaaggaga  gatcaatgag gaaggagtag cctattacaa taacctcatc      360
aatgaactcc tccagaatgg aatccaagcg tctgtcaact ttgtttcact gggatactcc      420
ccagtctctg gaggatgaat atggcggatt tctgaggcca accattgtga                470
```

<210> SEQ ID NO 142
<211> LENGTH: 413
<212> TYPE: DNA
<213> ORGANISM: Pinus radiata

<400> SEQUENCE: 142

```
ataagactaa ttttccagac aatcctccat tcccattcaa ttacactggt actccaccca       60
ataatacaca ggctgtgaat gggactagag taaaagtcct tcccttaac  acaactgttc      120 aattgattct tcaagacacc agcatcttca gcacagacag ccaccctgtc catctccatg      180
gtttcaattt ctttgtggtg ggccaaggtg ttggaaacta caatgaatca acagatgcac      240
caaattttaa cctcattgac cctgtcgaga gaaacactgt gggagttccc aaaggaggtt      300
gggctgctat aagatttcgt gcagacaatc caggggtttg gttcatgcac tgtcatttgg      360
aggttcacac atcgtgggga ctgaaaatgg cgtgggtagt aaagaacgga aaa             413
```

<210> SEQ ID NO 143
<211> LENGTH: 457
<212> TYPE: DNA
<213> ORGANISM: Pinus radiata

<400> SEQUENCE: 143

```
aaaaccttt  cagacgaatg ttctgatgct cggccccggc cagacaacag acatacttct       60
cactgccaat caggctacag gtagatacta catggctgct cgagcatatt ccaacgggca      120
aggagttccc ttcgataaca ccactaccac tgccatttta gaatacgagg gaagctctaa      180
gacttcaact ccagtcatgc ctaatcttcc attctataac gacaccaaca gtgctactag      240
cttcgctaat ggtcttagaa gcttgggctc acacgaccac ccagtcttcg ttcctcagag      300
tgtggaggag aatctgttct acaccatcgg tttggggttg atcaaatgtc cggggcagtc      360
ttgtggaggt ccaacggatc aagatttgca gcaagtatga atacatatca tttgtcccgc      420
aaccacttct tccaatcctt caagctcagc attttgg                               457
```

<210> SEQ ID NO 144
<211> LENGTH: 598
<212> TYPE: DNA
<213> ORGANISM: Pinus radiata

<400> SEQUENCE: 144

```
gttcggcact gagagatcca tttctttcaa tgttgagaca gtgagtagta ttagtttgat       60
atctctttca ggaatatatc gtgcttgcag gatctttagt ttctgcaaca atgtcgttgc      120
aatcagtgcg tctatcttct gttctccttg ttttgctact agcatttgtt gcttacttag      180
ttgctgtaac aaacgcagat gtccacaatt ataccttcat tattagaaag aagacagtta      240
ccaggctatg caataagcgt ataatcgcca ccgtcaatgg acagctacca ggcccaacta      300
ttcatgtacg tgatggagac gttgttaata tcaaagctta taacaaagct gggtacaatg      360
ccactcttca ctggcatgga gtcgagcagt tgcgtacagg atgggccgat ggacctgcat      420
atgttacaca gtgccccatt ccaccaggtg gtcgttatac atacagattc accatttctg      480
aacaggaagg caccgtgtgg tggcacgctc atgtgtcatg gctccgagct acggtgcatg      540
```

```
gagctttcgt aatccttcct aagagaggca aaccatatcc ctttcctaaa ccccgtgc        598

<210> SEQ ID NO 145
<211> LENGTH: 1080
<212> TYPE: DNA
<213> ORGANISM: Pinus radiata

<400> SEQUENCE: 145
aagatcttgg ttcgagtctc tcagctctct ccaaaggaat tttgtgggtc atttgcaggt        60
gaagacacca tggtgaaggc ttatcccacc gtaagcgagt agtacaaggc tgccattgac       120
aaatgcaaga ggaagctccg agctctcatt gcagagaaga actgtgcgcc gatcatggtt       180
cgaatcgcat ggcacagcgc tgggacttac gatgtcaaga ccaagaccgg agggcccttc       240
gggacgatga gatatggggc cgagcttgcc cacggtgcta acagtggtct ggacatcgca       300
gttaggctcc tggagccaat caaggaacag ttccccataa tcacctatgc tgacctttat       360
cagttggctg gtgtggtggc tgttgaagtg accgggggac ctgacattcc gttccatcct       420
ggaagagaag acaagcctga gcctccagaa gaaggccgcc ttcctgatgc tacaaaagga       480
cctgatcatc tgagggatgt ttttggtcac atggggttga atgataagga aattgtggcc       540
ttgtctggtg cccacacctt ggggagatgc acaaggaga gatctggttt tgaaggacca       600
tggacctcta acccccttat ctttgacaac tcttacttca cagagcttgt gactggagag       660
aaggaaggcc tgcttcagtt gccatctgat aaggcactgc ttgctgatcc tagttttgca       720
gtttatgttc agaagtatgc acaggacgaa gacgctttct ttgctgacta tgcggaagct       780
cacctgaagc tttctgaact tgggtttgct gatgcgtaga ttcataccttc tgcagagac       840
aattccttgc tagatagctt cgttttgtat ttcatctaat cttttcgatt atatagtcac       900
atagaagttg gtgttatgcg ccatagtgat acttgaacct acatgttttt gaaaagtatc       960
gatgttcttt aaaatgaaca ttgaatacaa cattttggaa tctggttgtg ttctatcaag      1020
cgcatatttt aatcgaatgc ttcgttcctg ttaaaaaaaa aaataaaata aaaaaaaaaa      1080

<210> SEQ ID NO 146
<211> LENGTH: 701
<212> TYPE: DNA
<213> ORGANISM: Pinus radiata

<400> SEQUENCE: 146
gtagtttcgt tttacaacaa tctcaggttt tgaatctcag aatagttgcg aaaggaagcg        60
atgacgaagt acgtgatcgt tagctccatt gtatgtttct ttgtatttgt ttctgcgtgc       120
ataatttctg tcaatggatt agttgtccat gaagatgatc tgtcaaagcc tgtgcatggg       180
ctttcgtgga cattttataa ggacagttgc cccgacttgg aggccatagt gaaatcggta       240
cttgagccgc cgttggacga agatatcact caggccgcag gttgctgaga cttcatttcc       300
atgactgttt tgtgcagggt tgcgatgggt ccgtgttgct gacaggaact aaaagaaacc       360
ccgagtgagc aacaggctca gccaaactta acactaagag cccgggcctt gcagctgatc       420
gacgaaatta aaaccgctgt agaagctagc tgcagtgggg ttgtaacttg tgcagacatt       480
ctggctttgg ctgctcgtga ctccgtcgct caggaggccc aaaatttcca gtaccacttg       540
gccgcagaga tagcctaaag tttgccagtc aatccgtagt tctcgccaat ataccaactc       600
caactttaaa tttgacacag ctgatgaaca tttttggctc caaaggattc agtttggccg       660
aaatggttgc tctttcaggt ggacacacaa tcggcattgg t                          701
```

<210> SEQ ID NO 147
<211> LENGTH: 338
<212> TYPE: DNA
<213> ORGANISM: Pinus radiata

<400> SEQUENCE: 147

```
ctcaattctg tgctgctctg ctcgctcagg gccgggtctg ctattctgct catgcacaag      60
tttgagatcg ggagcctgct ggatctggtg cagaggttca aggtcacggt agcgcctgtc     120
gtgcctccca ttgttctcgc ctttgccaag aacgcgctcg tggaaagcta tgatctgtcg     180
tccattaggg ttgtgctgtc cggtgccgcg cctctcggaa aggagctgga ggatgcatta     240
aggctacgac ttcccaaagc cacttttggt cagggatacg gtatgacaga ggcaggaccg     300
gtgctatcaa tgtgtctggc cttcgctaag gagcccctt                            338
```

<210> SEQ ID NO 148
<211> LENGTH: 357
<212> TYPE: DNA
<213> ORGANISM: Pinus radiata

<400> SEQUENCE: 148

```
ctcaattctg tgctgctctg ctcgctcagg gccgggtctg ctattctgct catgcacaag      60
tttgagatcg ggagcctgct ggatctggtg cagaggttca aggtcacggt agcgcctgtc     120
gtgcctccca ttgttctcgc ctttgccaag aacgcgctcg tggaaagcta tgatctgtcg     180
tccattaggg ttgtgctgtc cggtgccgcg cctctcggaa aggagctgga ggatgcatta     240
aggctacgac ttcccaaagc cacttttggt cagggatacg gtatgacaga ggcaggaccg     300
gtgctatcaa tgtgtctggc cttcgctaag gagccctttc cgatgaagtc cgggtcg       357
```

<210> SEQ ID NO 149
<211> LENGTH: 470
<212> TYPE: DNA
<213> ORGANISM: Eucalyptus grandis
<220> FEATURE:
<221> NAME/KEY: unsure
<222> LOCATION: (437)...(437)

<400> SEQUENCE: 149

```
gagaaattca caagcttcac agcacgagag ttaaagagcg agacacggtt tgatccagtg      60
aagggccggc ccccggagat ggcgaagacg ctcaccgcgc tggctggggg agaagaccct     120
ccagtccaaa gttcgtccgc gataaggatg agcgccccac ggtggcctac aaccagttca     180
gcaacgtgat ccccgtgata tccctggcgg ggattgacga ggccggcggc cggaagggcc     240
gagatctgca agaagatcgt ggaggcgtgc gaggactggg gcgtcttcca ggtggttgac     300
cacggggttg atacggggct catcactgac atgacccggc tcgcgcgtaa gtncttcgct     360
ctgccctcgg aggaaaagct ccggttcgac atgactggcg gaaaagggg gggttatcgt     420
ctccagcatc tcaaggngaa caagttcagg actggtgcaa aagtacgaac                470
```

<210> SEQ ID NO 150
<211> LENGTH: 380
<212> TYPE: DNA
<213> ORGANISM: Eucalyptus grandis

<400> SEQUENCE: 150

```
ggaggtcggt gacagagcag tacagcgaga agctcatggc cctcgcttgc aagctcttgg      60
aggtcctctc ggaggcaatg ggactggaga aggaggcact gaccaaggca tgcgtggaca     120
```

```
tggaccagaa ggtggtggtc aactactacc ccaaatgccc gcagcccgac ctcacgctcg      180
ggctgaagcg ccacactgac ccgggaacca tcactcttct gctccaggac caggtggggg      240
gcctccaggc caccagagat ggcggcaaga gctggatcac cgtccagcct gtggaagggg      300
cttttgtggt caacctaggc gatcatggtc atttcctgag caacgggagg ttcaagaacg      360
cggaccacca ggcggtggtg                                                  380
```

<210> SEQ ID NO 151
<211> LENGTH: 349
<212> TYPE: DNA
<213> ORGANISM: Pinus radiata
<220> FEATURE:
<221> NAME/KEY: unsure
<222> LOCATION: (212)...(212)

<400> SEQUENCE: 151

```
ttggactcca tacctctcgt ggacctccaa ggtcttttac gcgattctgc tagagcccac       60
gttattcaac aaattggccg ggcctgcgct gaatatggct tcttccagat aatcaatcat      120
ggcatcccag atgcagttat caacaggatg ctggaagtag cgaaggagtt tttcagaatg      180
cctgtggagg accgaatgga atactattcc gncgatccgt ccagaaaaac acgtttgtcg      240
acgagcttca acatccataa agaacaagtc ttcaactggg gggctatctc agacatcatt      300
gttatccgtt agaagatcat gttcacactt ggccttcaaa acctgcggg                 349
```

<210> SEQ ID NO 152
<211> LENGTH: 427
<212> TYPE: DNA
<213> ORGANISM: Pinus radiata
<220> FEATURE:
<221> NAME/KEY: unsure
<222> LOCATION: (234)...(234)
<221> NAME/KEY: unsure
<222> LOCATION: (240)...(240)

<400> SEQUENCE: 152

```
atggtctggg cagcatacgg aggacgatgg aagatggaac gcaaggtgtg caacatgcac       60
atgttgggag ggaaggcgtt ggaagattgg cagccggtga gggacgccga aatgggcttc      120
atgctccgga atattctcag tcactcgcag cgcggcgaga cggtgaatgt gccgacctc       180 ctgaacatct gcgccgccaa catgatcggg cagatcattc taagcaagcg ggtnttcgan      240
acagaagggg acgaggccaa cgagttcaag gacatggtgg tggaactcat gacctgcgct      300
ggatacttca atatcggaga cttcattcca tcgctagcgt ggatggactt gcaggcatt      360 cagcggggta tgaagaagct ccacaagaaa tgggacgcac tcatacagag gattattgat      420
taacacc                                                                427
```

<210> SEQ ID NO 153
<211> LENGTH: 298
<212> TYPE: DNA
<213> ORGANISM: Eucalyptus grandis
<220> FEATURE:
<221> NAME/KEY: unsure
<222> LOCATION: (214)...(214)

<400> SEQUENCE: 153

```
gttaccaaag ggcagcaacg tattcttaaa catgggttct atccacaggg atcccaagat       60
ttgggacaaa ccgttggagt ttagacccga gaggttcttg gaaggtccta gcaagtatga      120
tttctcaggt aacaacttcg catacatgcc attcggttct ggtcgaaggg tgtgtgcagg      180
```

-continued

```
gcttgcgctg gcagagagga tgctaccata tgtnttggcc tctcttttgc actcattcaa      240
gtgggaaata ccaccagggt ctgagctgga tttacctgga caagttcggc cttgtggt       298
```

<210> SEQ ID NO 154
<211> LENGTH: 251
<212> TYPE: DNA
<213> ORGANISM: Eucalyptus grandis

<400> SEQUENCE: 154

```
gacttcaaag ggcaggattt tgagctgata cccttcggtg caggtagaag gagctgcccg      60
gctattgcat ttggaaatgc cagtgttgag cttgctttag ctcaacttct tcacagtttc     120
gattgggagc ttcctgatgg gatccagcct agggacttgg atatgaccga agttttggc     180 atcacaatgc acagaattgc caacctcatg gttgtagcca aaccccgctt ctcctagacg     240
atactcgtgc c                                                          251
```

<210> SEQ ID NO 155
<211> LENGTH: 411
<212> TYPE: DNA
<213> ORGANISM: Pinus radiata
<220> FEATURE:
<221> NAME/KEY: unsure
<222> LOCATION: (198)...(198)

<400> SEQUENCE: 155

```
acggggctcc ggtgacgaga tactggcagg tcgttgaagc tggttggagg ttcgaatatc      60
cgagagggat cctgtttctt gtccccttac cttggttttc ctcatccttc cgaatgcagt     120
ctaattcgaa gaccgtggaa gagcggcgcc cggggcctgg gtaagagctt gctgagata     180 tctcggcttg actatgtntt ggctcttttc gtgaatggca aggggatct agggcgatg     240 atggggtcgg ctgtcgtttt gagggaaaat tcgcaactgt tgatggtctt gactacatct     300
ctggccgtct tgattggttg cgttttgttc tttgtttggc ggagaggggg atcggctccc     360
tcgaagcagc cggagaagcc aactcccctg gtgaaagaag aggaagagga g              411
```

<210> SEQ ID NO 156
<211> LENGTH: 404
<212> TYPE: DNA
<213> ORGANISM: Pinus radiata

<400> SEQUENCE: 156

```
gctgaagtta ataaaactaa gtacattgag gttgacatgg aggcagaatt ttcaaatcta      60
gctttggaca ttattggatt gtgtgtattt aactatgatt ttggatccgt tactcgagaa     120
tcaccagtaa tcaaggcagt ctatggtaca ttgtttgaag ctgagcatag atcaaccttt     180
tacataccat actggaaatt tccgctggca agatggttag ttcctcgcca acgaaagttc     240
catgaagacc taaaggtcat taatgaatgt cttgataatc tgatagcagg ggccaaggaa     300
acaagacagg aagacgatat cgaggctctt caaggaagag attactctaa agtgaaatat     360
gcaagtttgc tcagatttct agttgatatg agggagaaga tgtt                      404
```

<210> SEQ ID NO 157
<211> LENGTH: 259
<212> TYPE: DNA
<213> ORGANISM: Pinus radiata
<220> FEATURE:
<221> NAME/KEY: unsure
<222> LOCATION: (116)...(116)
<221> NAME/KEY: unsure
<222> LOCATION: (246)...(246)

<400> SEQUENCE: 157

```
ccaatcatcg gcaatttcca ccaagtgaga cttcctcttc accgtgctct caaaaatctt    60
gctgagaaat atggtccat tttgtttctg cgctttggct ctgtacccac tgtggntgtt    120
tcttcatctg agatggccaa acactttctt aaaactcatg atttgatatt tgccagccga   180
cctccaacat cggtaggaaa atatttcttc tataacttca agatattgc cttcagtcct    240
tatggngatc actggagga                                                259
```

<210> SEQ ID NO 158
<211> LENGTH: 338
<212> TYPE: DNA
<213> ORGANISM: Pinus radiata

<400> SEQUENCE: 158

```
aatggcagtt gggggtcaag gaaatgtggt ctcagcttgc aggcagccat ggaagctaca    60
atcgtctggt gggtgttttg gtagtaatag tttctctggc agttttttat ttgaagagta   120
gaggttcgaa gaagcgtctg cctccagggc cgaaggtggg cctctggttg gaaatttgtt   180
tcaggttgca ttctccggga agcccttcat gtatgtggtg cgagatctga gggagcagtt   240
tggctcgatt tcacgctcc aaatggggca aaaaacgccc caaattacca cctccccgaa    300
atttccaaca cggggcctct taaaaaagag ggggcccc                           338
```

<210> SEQ ID NO 159
<211> LENGTH: 539
<212> TYPE: DNA
<213> ORGANISM: Pinus radiata
<220> FEATURE:
<221> NAME/KEY: unsure
<222> LOCATION: (1)...(539)
<223> OTHER INFORMATION: n at all occurrences indicates unsure

<400> SEQUENCE: 159

```
aatgtggccg aggagttcct gnaagactca tggatctggc tttcgccagc agacctccaa    60
ccatcggtaa cgaatatttt ggtataattc ctccgacgtc gcattttccc cctatggtcc   120
ttactggagg cagatgcgta aaatctgtgt gttaaagttg ctgagctcaa gacgcataga   180
ttccttccgc cacataagag aagaggaagt ctcttctatg gttcgctcta ttgctaattc   240
ggatctgcat cctgtgaaca ttagcagggc cgtgtcagcc cttgggattg atataatctg   300
caggatggcc ttcggtaaaa agtactgtga ccaagaccta attggtggca ttgggatnaa   360
gtcaatgata aaggaaacgt ttgtgtnagc agggtcnttg aacatgggag atttttatacc   420
atacttggca tggattgatc ttcaaggtct caaccgtcga ttgaagaaca tacacaagat   480
ccaagacgac ttgttagggg aagatactag aggcacacgc ttcgccaacc gcagaataa   539
```

<210> SEQ ID NO 160
<211> LENGTH: 310
<212> TYPE: DNA
<213> ORGANISM: Pinus radiata
<220> FEATURE:
<221> NAME/KEY: unsure
<222> LOCATION: (16)...(16)

<400> SEQUENCE: 160

```
cgaatgggtg gtcggnaaag accgcacagt aaaggagtct gatttggtaa gtctgaaata    60
ccttcagtgt gtggtgaaag agacgctacg attataccg ggaggacctc tagcacttcc    120
ccatgagtct gtggaggctg tgacagtaga agggtactat atacctaaga agacgatgct   180
```

```
gttggtgaat gtgtgggcta taggaaggga ccccaaagtg tgggggattg atgcttcaga      240
attcaagcca gagagattta tggaggaatt aggtgggcat ctgcatgata atgtcatgga      300
tttagcaggc                                                            310
```

```
<210> SEQ ID NO 161
<211> LENGTH: 412
<212> TYPE: DNA
<213> ORGANISM: Eucalyptus grandis

<400> SEQUENCE: 161
cgccacctcc ctcctcctct tcccctcct cctgctcctc ctggtcgccc cgcaaaagcc       60
ctccgcctct gtccgcagtc accgccagcc atggatctcc tcctcctgga gaagaccctc     120
ctgggcctct tcgccgccgc catcgtggcc atcgcggtct ccaagctccg gggcaagcgg     180
ttccgcctcc cccgggccc cctccccgtg cccatcttcg gcaactggct ccaggtcggc     240
gacgacctca accaccgcaa cctcaccgac ctcgccaaga ggttcggcga catcctcctc     300
ctccgcatgg ggcagcgcaa cctcgtggtc gtctcgtccc cggacctctc caaggaggtg     360
ctccacacgc agggcgtcga gttcgggtcc cgcacccgga acgtcgtctt ct              412
```

```
<210> SEQ ID NO 162
<211> LENGTH: 329
<212> TYPE: DNA
<213> ORGANISM: Pinus radiata

<400> SEQUENCE: 162
acttttacaa tgagtgatca caaacaattt tttccaaaat tcataacaaa attttggata       60
cagtgcatat tcgggcaaac aatctgacgg acttcaaaac tactgacaac aaaacaaacc     120
atctggggat gaattacaat ggaaatccac acttcatttg gctgcaactg tatatataaa     180
gtgtttattg cttccagctc ctccagactt tggaagaaat tctatatttt ttttttcagga   240 tctgagcttc aggctattgg tttggccaca acaacggagt ggttgagaat gtgcaggctg     300
aattgccctc ctttctctgt cacatccac                                        329
```

```
<210> SEQ ID NO 163
<211> LENGTH: 475
<212> TYPE: DNA
<213> ORGANISM: Pinus radiata

<400> SEQUENCE: 163
atttgcgtca gtctctacct ttgcctgcaa cattcacagt cgctgatgga gggcctcccg       60
cagcaactgt cctgtgctta ctctgggctt tcttcatgat atggttttg ggcaagagaa      120 gaactagtgc cacgctgcca ccaggaccct atgcatggcc catcatagga aacctctacc     180
aattaatact gcccgctcac cgttctctta gaggccttgc tgacaaatat ggtcccatta     240
tgtttctgcg cttaggctct gtccctaccg tcgtcgtttc ttcttctgag acggccaaag     300
agtttctcaa aactcatgac ttgattttg ccagccgacc cccaacagcc gctgggagat      360
tgatgttttc caactctaaa gacgtggtgt tcgctccgta tggagatcac tggaggcaaa     420
tgagaaaaat atgcgtgtta gaactactga ctgccaaaag aatcgagctc gtgcc            475
```

```
<210> SEQ ID NO 164
<211> LENGTH: 372
<212> TYPE: DNA
<213> ORGANISM: Pinus radiata
<220> FEATURE:
```

```
<221> NAME/KEY: unsure
<222> LOCATION: (22)...(22)

<400> SEQUENCE: 164
tggaaataca gttcgactct gngatttcat aaaatatgat gaggaaagga gaatcaggtg    60
gatttgaggt taagggatgg gctgccatgg atgactccgg cgtcctctcg cctttcaact   120
ttactcgcag gaaaacggga tcccacgatg tactttcaag gtagcatact gtggaatctg   180
tcactccgat ctgcatcaaa ttcggaatga atggaaaaat tccctatacc caaatgggtt   240
ccaggccacg aaatcgtagg aactgttgct tgaagttcgg tcagaagtga agaattttgg   300
ctggctggag aatcggcggt gggtgtaagg gttgcatggg tttggaggtg ccagccaatt   360
ggtgaattct tg                                                        372

<210> SEQ ID NO 165
<211> LENGTH: 307
<212> TYPE: DNA
<213> ORGANISM: Eucalyptus grandis

<400> SEQUENCE: 165
tctctctctc tctccctctt gagagtgttg aagtgttagg atgaggattc gagtgccgtc    60
gatgctgttg ttgtggtcac tgttgggcct cgtggcgagg tcgacaatgg ccgaagagac   120
ggtgatcccc gagacaacgc gtttcgacac cggtgggctg agcagatcgg ccttcccgaa   180
gggcttcgtc tggggacgg cgacctcggc ttatcaagtc gaaggcatgg ccgacaaaga   240
gggacgcggg cctagcatct gggacgtctt cgtcaagatt ccaggaattg tggccggtaa   300
tgcaact                                                              307

<210> SEQ ID NO 166
<211> LENGTH: 454
<212> TYPE: DNA
<213> ORGANISM: Eucalyptus grandis

<400> SEQUENCE: 166
gaagaaatta ggtttcttgt tgcggctttt ggtagtgggt ctggtgatag cagagacggt    60
ccatggtgct tatgagttca gcagatacga ctttcctcct ggctttgtgt ttggtgctgg   120
cacttcagct tatcaggtcg aaggagcagc aaatgaggat gggaagactc caagtataat   180
ggacacctgg gcccactctg actcagggat tacaagcgga gcaaatggag atattgcctg   240
tgatcaatat cacaaataca aggtagatgt ccaactcatg gcagaaatgg gattagacgc   300
ataccggttt tccatctcat ggtcaaggct catcccaaat gggagaggct ctgtgaatcc   360
gaagggattg cagtactaca acaacctcat caatgaactg atcagccatg ggattgaacc   420
cgcacgtgac cctgcaccat tttgatctgc caca                                454

<210> SEQ ID NO 167
<211> LENGTH: 433
<212> TYPE: DNA
<213> ORGANISM: Pinus radiata

<400> SEQUENCE: 167
gagaagcaat aggaaaatat ggccctggag aatggtgaaa gaagcagagt actgatcatt    60
ggaggaaccg gttattttgg cagaaggtta gtgaaggcca gccttgcctt cggacatgag   120
acttatgtcc agtatcgtgc ccaggcagcc tctgatatca caaagtgga gacgcttatt   180 tccttcaaat ctcaaggagc acacctggtg gatgcttcca ttgacaatca cacaagcctc   240
```

| | |
|---|---|
| gtaaatgccg tgaaacgagt ggaagttgta atatcggcga tgggtgccga gggtctgaga | 300 |
| gaggggcagc tgaaagtgat cgaggccatt aaagaggcag gaaccgtcaa gcgctttctt | 360 |
| ccttctgagt tcgggatggc ccagacagaa tggtgcacgc catctatccg ggcaacgagg | 420 |
| ttttctctga taa | 433 |

<210> SEQ ID NO 168
<211> LENGTH: 330
<212> TYPE: DNA
<213> ORGANISM: Pinus radiata

<400> SEQUENCE: 168

| | |
|---|---|
| cggggagctt gacttgggac tggaaagcag cgggcatcgt ttcctgtggg ttctccgcgg | 60 |
| tcatccttcc aatccaaact tatctgcgct gctgccccg ggtttcgaac agcggaccaa | 120 |
| agatcgtggt ctcgtggtta cctcatgggc tccgcaggtt tctatccttg cacacccgtc | 180 |
| aacaggaggt tttgtgagtc actgcggttg gaactcgatg ctggagagca tttggtttgg | 240 |
| agttcccatt atcgcttggc ccctccaagc tgaccaaagg ccgatcgggt tactttctgg | 300 |
| tgaatgatag tagaatagac ggtaggcttg | 330 |

<210> SEQ ID NO 169
<211> LENGTH: 398
<212> TYPE: DNA
<213> ORGANISM: Eucalyptus grandis

<400> SEQUENCE: 169

| | |
|---|---|
| ggaaaatttg gtatcggtag agagatcctg tgagatcgac gcgtgggtcg accttcaaaa | 60 |
| tttgacccgt gaggtgatct ctcgaacagc gtttggcagt agcttcgaag aaggcaaaag | 120 |
| gatctccgaa cttcagggg aacaagccca gctcacgata atagcccttc aatcggtcta | 180 |
| catccctggt tggaggtttg tgccaactaa gatgaacagg aggatgaaga gcatagataa | 240 |
| ggaagtgcgg gctctgctca tggacatcat ccgcagaaga gagaaagcaa taagggaagg | 300 |
| ggaagctgct ggcgatgatc tgctgggggct gttgctggag tcaaacatga aggagaatgt | 360 |
| cgggatgagc cttcacgatg tgatggacgg agttgcag | 398 |

<210> SEQ ID NO 170
<211> LENGTH: 432
<212> TYPE: DNA
<213> ORGANISM: Eucalyptus grandis
<220> FEATURE:
<221> NAME/KEY: unsure
<222> LOCATION: (214)...(214)

<400> SEQUENCE: 170

| | |
|---|---|
| gttaccaaag ggcagcaacg tattcttaaa catgggttct atccacaggg atcccaagat | 60 |
| ttgggacaaa ccgttggagt ttagacccga gaggttcttg gaaggtccta gcaagtatga | 120 |
| tttctcaggt aacaacttcg catacatgcc attcggttct ggtcgaaggg tgtgtgcagg | 180 |
| gcttgcgctg gcagagagga tgcaaccata tgtnttggcc tctcttttgc actcattcaa | 240 |
| gtgggaaata ccaccagggt ctgagctgga tttactggac aagttcggcc ttgtggtcaa | 300 |
| gaaaatgaag ccccttgtcg ccattccaag accaagattg tccactctgg agctctacat | 360 |
| gtcgagatag atatttcatt agagtcccaa agctcttcat ttcaattcta agaaataaac | 420 |
| gtatcctgcc ag | 432 |

<210> SEQ ID NO 171

<211> LENGTH: 303
<212> TYPE: DNA
<213> ORGANISM: Eucalyptus grandis
<220> FEATURE:
<221> NAME/KEY: unsure
<222> LOCATION: (105)...(105)

<400> SEQUENCE: 171

| | | | | | |
|---|---|---|---|---|---|
| ccatcgcggc | cctggcccgg | acctacgggc | cgctcatgca | cctgcggctc | gggttcgtac | 60 |
| gacgtggtgg | tggccgcgtc | ggcctccgtg | gccgccgagt | tcctnaagac | ccacgacgcc | 120 |
| aacttctcga | gccggccgcc | caactccggg | gcgaacacat | cgcgtacaac | taccaggacc | 180 |
| tgatgttcgc | gccctacggc | cgcggtggc | ggatgctaag | gaagataagc | tccgtccacc | 240 |
| tcttctccgg | caaggctctt | aagcattaca | gacacgttcg | ccagaaaaag | gtcgcaatcc | 300 |
| tca | | | | | | 303 |

<210> SEQ ID NO 172
<211> LENGTH: 518
<212> TYPE: DNA
<213> ORGANISM: Pinus radiata

<400> SEQUENCE: 172

| | | | | | |
|---|---|---|---|---|---|
| cattagatat | atatatatag | acacgcattt | acgatatcat | tgcaacaatg | tcattggtag | 60 |
| gctgggttgt | ttttctaatc | gctttgattt | cgtatttggc | tgccatcaca | aatgcagcaa | 120 |
| tcgtcaatta | taccttcatc | attgaagcga | agacagttac | caggctatgc | aaggagaata | 180 |
| caataatcac | cgtcaatggg | cagctaccag | gtccgaccat | ctatgtccat | gacggagaca | 240 |
| ctgttattgt | tgaaacttat | aacaaggccg | agtacaatgc | cactcttcac | tggcatggag | 300 |
| tggagcagtt | gcgtacacca | tgggctgatg | gacctgcata | tgttactcaa | tgtcccattc | 360 |
| caccaggtgg | tcgttataca | tacagattca | acatctctgg | acaagaagga | accgtgtggt | 420 |
| ggcatgccca | ttactcatgg | ctccgagcta | cggtccatgg | agcttttgta | atccttccta | 480 |
| aggaaggaag | ctcatatccc | ttttctaaac | ccaatgcc | | | 518 |

<210> SEQ ID NO 173
<211> LENGTH: 309
<212> TYPE: DNA
<213> ORGANISM: Eucalyptus grandis
<220> FEATURE:
<221> NAME/KEY: unsure
<222> LOCATION: (284)...(284)
<221> NAME/KEY: unsure
<222> LOCATION: (294)...(294)

<400> SEQUENCE: 173

| | | | | | |
|---|---|---|---|---|---|
| gccgctgatc | ctaggattga | gatctgcatg | ctccccgtgg | gtgatggcat | cactctctgc | 60 |
| cgtcggatca | gctgagcatc | taatctcaag | tccttatgat | cagggttcat | tcttaatgta | 120 |
| gaacccacga | aaaagagagg | gatttatgta | tatcttgttg | ctgtttcttt | tccatgaacc | 180 |
| tagaaacggg | attcgcaatt | aaatgccaaa | ttatgttgct | gtttctcttt | agtgctctcg | 240 |
| atttcttttt | attttttaat | tttttgatc | agtttcttcg | aatnatctca | agtncttcca | 300 |
| aaaaaaaaa | | | | | | 309 |

<210> SEQ ID NO 174
<211> LENGTH: 381
<212> TYPE: DNA
<213> ORGANISM: Eucalyptus grandis

<400> SEQUENCE: 174

```
taagacgaag aaatggaaac aacggccaag ccatcgcgaa acgcctttcc gcatatggaa      60
tgcactatat ttgatcttcc gcatgtggtg gccaatttag aagttagcga gaacgtgaga     120
tgtgttcctg gggacatgtt tgagtccata ccaccagcag atgcaataat attgaagtgg     180
atactccatg attggagcga tgaagacgct gtgaagatac tgaagcgatg caaggaggcc     240
ttaggcaagg gcaagggcaa gaaacagaag gtaattataa ttgacatggt gatggacaac     300
acgaagagcg ccaaagagac ggtcgaaacc cagctcttct atgacatgtt gattgatgaa     360
ccctcgccgt cgggaaaggg g                                                381

<210> SEQ ID NO 175
<211> LENGTH: 236
<212> TYPE: DNA
<213> ORGANISM: Pinus radiata
<220> FEATURE:
<221> NAME/KEY: unsure
<222> LOCATION: (37)...(37)

<400> SEQUENCE: 175
tgaattacca catgcggctg atagatctgg tgaaggncgg aggattgatt gcgtatgaca      60
atactctgtg gcaaggatcc gttgcgcttc ccccagaagt cgccatgagc gaaggcatga     120
gttatgggga agacagagag catatgttgg aactaaacag ggcccttgct gcagaccctc     180
gcatcgagat tgctcagatc ccaattgccg atggagtgac gctgtgcagg cgcctt         236

<210> SEQ ID NO 176
<211> LENGTH: 404
<212> TYPE: DNA
<213> ORGANISM: Pinus radiata
<220> FEATURE:
<221> NAME/KEY: unsure
<222> LOCATION: (1)...(404)
<223> OTHER INFORMATION: n at all occurrences indicates unsure

<400> SEQUENCE: 176
gtcgggaatt ccacttacca gaccattaat tcacgattca tcccacctca gcctggaaat      60
ttggtctgaa tctggagccc aatactgtac aagtagcctt ggtctcttcg ggaatccgtg     120
tntggaaaga agaaattgag atccggccaa agatggttgc agggtcagac ctgggcgctg     180
tgcaggccaa tggaaatcaa aatggaaatg gatttcatca tgtgcattct gttgatctct     240
gcattcagaa tggnccagac cctctgaact gggggcaggc tgccaaggcc ctgcagggct     300
cccactttga agaagtgaag ctcatggtgg ngtcctattt cggatccgng gaagtttcca     360
ttgaaggcaa atcngtcaca atcgcggatg tgaccgcagt tgcc                      404

<210> SEQ ID NO 177
<211> LENGTH: 415
<212> TYPE: DNA
<213> ORGANISM: Pinus radiata
<220> FEATURE:
<221> NAME/KEY: unsure
<222> LOCATION: (20)...(20)

<400> SEQUENCE: 177
cccaacgcta tgcgtctgan caggcaactt tcttcagtgc atttgtggcg gccatggata      60
aattgggcag tgtgggtgta aaaactggca cacaggggga ggtcaggagg agatgtgatg     120
cgttcaattg agaagagtaa agttcaaatt ctctccatta ttaaggtggg attgtatgca     180
tggttgagat taatgaacgg aacaaagaaa atttaatgtt ttgtaactag tgagattgat     240
```

```
gaattgaata aagaattttt cctgtcctct gattcaacct gttttgcact ctgtgaagca      300
ctttacagtc tggactctgg aaggaatcca tcaaatcgtg actaagaaaa gggtaatgat      360
tttaaagaga ttccgttgcg ctcattccat tggggattc ctgaaaatat ctgcc           415

<210> SEQ ID NO 178
<211> LENGTH: 409
<212> TYPE: DNA
<213> ORGANISM: Pinus radiata

<400> SEQUENCE: 178
gatgggcgcg caattctttt cagccggctg gtgtagttgc tgttgaggtt acgggaggtc      60
ccacaattga gtttgtccct ggtcgtaagg attcactggc atcaccacga gaagggcggc     120
ttcctgatgc gaagaaaggt tcacaacacc taagggatat cttttatagg atgggcctat     180
ctgacaagga tatagttgct ctttctggag cgcacaccat tgggaaaagc acatccagaa     240
aggtcaggct ttgatggagc atggaccgag cagcctctga gtttgataa ttcatatttt      300 gtagagcttc tcaaaggcga gtctgaagga ttactccaat tgcctacgga caaatgcttg     360
gtagaggatc ccagtttccg cccttatgtg gatctttatg ccaaggatg                 409

<210> SEQ ID NO 179
<211> LENGTH: 411
<212> TYPE: DNA
<213> ORGANISM: Eucalyptus grandis
<220> FEATURE:
<221> NAME/KEY: unsure
<222> LOCATION: (393)...(393)

<400> SEQUENCE: 179
agagcttctc ccagagaggc ctctctatgg aagatctcgt cgctctttcg ggaggccaca      60
cactaggatt ttcccactgc tcctccttcg caggcaggat ccgcaacttc aacaccacgc     120
acgacatcga cccatcgatg cacccatccc tggcagcgag cctaagaggc gtgtgcccga     180
gcaagaacag gccaaaaaac gcagggacca ccatggaccc ttcctcgacc accttcgaca     240
acacgtacta cgggctgatc ctccagggga agggcctgtt ctcttcggac caggccctcc     300
tggcagtgcc caagacgaag gatctggtcg agaagttcgc aggctcgcac aaggaattca     360
cggatgcatt cgtcaagtcc atgatcaaga ttnagcagca tcacaggcgg a              411

<210> SEQ ID NO 180
<211> LENGTH: 334
<212> TYPE: DNA
<213> ORGANISM: Pinus radiata

<400> SEQUENCE: 180
gcatcatggg aagtacaact gggaagaaga gacagcctaa cagcaagcaa aacagcagca      60
aataacaaca ttccagcccc cacatcaaat gttgcaacac ttaactccaa gtttcagaat     120
gtaggcctca ctgaacaaga catggtcaca ctctcaggag cccatacaat aggaaaggcg     180
cgttgtgcaa cattcaactc taggctcacg ggacaaccgg atcccactct tcagaaagag     240
tttttgacat cgctccaaca aatctgcttt caagggctag ccagtaataa caacaccgta     300
acttcactgg atgtggagac tcccgtcatt tttg                                 334

<210> SEQ ID NO 181
<211> LENGTH: 343
<212> TYPE: DNA
<213> ORGANISM: Pinus radiata
```

```
<400> SEQUENCE: 181
atttcgctga actggatctg gatcgaagaa ggtattgcat atcaaagaaa gaggcaaata      60
tgactccggc cactgttttg ctttctatat ttgtgattgt atatggtagt gctgtgaacg     120
ctctgccaac tcccgtggcg ggtctttcgt ggacgttcta caacacaagt tgcccgtcat     180
tggagtcgat agtgcggaag cgcatggaag cctatttgag tgcagacatc acacaagctg     240
caggattgct gaggctccac ttccacgact gttttgtcca gggatgcgac gggtctgtgt     300
tgctgaactc aacatcgggg gagcaaacag ttgcgcccaa ctt                        343

<210> SEQ ID NO 182
<211> LENGTH: 443
<212> TYPE: DNA
<213> ORGANISM: Pinus radiata
<220> FEATURE:
<221> NAME/KEY: unsure
<222> LOCATION: (164)...(164)

<400> SEQUENCE: 182
atttcgctga actggatctg gatcgaagaa ggtattgcat atcaaagaaa gacgcaaata      60
tgactccggc cactgttttg ctttctatat ttgtgattgt atatggtagt gctgtgaacg     120
ctctgccaat tcccgtggcg ggtctttcgt ggaccgtttt acancacaag ttgcccgtca     180
ttggagtcga tagtgcggaa gcgcatggaa gcctatttga gtgcagacat cacacaagct     240
gcaggattgc tgaggctcca cttccacgac tgttttgtcc agggatgcga cgggtctgtg     300
ttgctgaact caacatcggg ggagcaaaca gttgcgccca acttatcact cagagcggag     360
gctctgaaaa tcatcaatga catcaaagag aacgtagaag cggcgtgcag cggaactgtg     420
tcgtgtgcag acattcttgc ctt                                             443

<210> SEQ ID NO 183
<211> LENGTH: 243
<212> TYPE: DNA
<213> ORGANISM: Pinus radiata

<400> SEQUENCE: 183
acattgatga ttgtgctacg cgtattttt tcaatctcta gcacttggga aggtctggag      60
gaggcggctc caaggttgcc tgagggccgt gaccgttctt cactataaac accatattca     120
gtccccatac taaatggtcg tctaaatggc agtggagaaa ccacactcct ggattgtcag     180
ctttgaatct tatcgcaacc caaccgctca caggagctat tactgtgttg cgtagtgggg     240
atc                                                                   243

<210> SEQ ID NO 184
<211> LENGTH: 1474
<212> TYPE: DNA
<213> ORGANISM: Pinus radiata

<400> SEQUENCE: 184
gaattcggca cgagaaaacg tccatagctt ccttgccaac tgcaagcaat acagtacaag      60
agccagacga tcgaatcctg tgaagtggtt ctgaagtgat gggaagcttg gaatctgaaa     120
aaactgttac aggatatgca gctcgggact ccagtgccca cttgtcccct tacacttaca     180
atctcagaaa gaaaggacct gaggatgtaa ttgtaaaggt catttactgc ggaatctgcc     240
actctgattt agttcaaatg cgtaatgaaa tggacatgtc tcattaccca atggtccctg     300
ggcatgaagt ggtgggggatt gtaacagaga ttggcagcga ggtgaagaaa ttcaaagtgg     360
```

```
gagagcatgt aggggttggt tgcattgttg ggtcctgtcg cagttgcggt aattgcaatc       420
agagcatgga acaatactgc agcaagagga tttggaccta caatgatgtg aaccatgacg       480
gcacacctac tcagggcgga tttgcaagca gtatggtggt tgatcagatg tttgtggttc       540
gaatcccgga gaatcttcct ctggaacaag cggcccctct gttatgtgca ggggttacag       600 tttcagccc aatgaagcat ttcgccatga cagagcccgg gaagaaatgt gggattttgg        660
gtttaggagg cgtggggcac atgggtgtca agattgccaa agcctttgga ctccacgtga       720
cggttatcag ttcgtctgat aaaaagaaag aagaagccat ggaagtcctc ggcgccgatg       780
cttatcttgt tagcaaggat actgaaaaga tgatggaagc agcagagagc ctagattaca       840
taatggacac cattccagtt gctcatcctc tggaaccata tcttgccctt ctgaagacaa       900
atggaaagct agtgatgctg ggcgttgttc cagagccgtt gcacttcgtg actcctctct       960
taatacttgg gagaaggagc atagctggaa gtttcattgg cagcatggag gaaacacagg      1020
aaactctaga tttctgtgca gagaagaagg tatcatcgat gattgaggtt gtgggcctgg      1080
actacatcaa cacggccatg gaaaggttgg agaagaacga tgtccgttac agatttgtgg      1140
tggatgttgc tagaagcaag ttggataatt agtctgcaat caatcaatca gatcaatgcc      1200
tgcatgcaag atgaatagat ctggactagt agcttaacat gaaagggaaa ttaaattttt      1260
atttaggaac tcgatactgg tttttgttac tttagtttag cttttgtgag gttgaaacaa      1320
ttcagatgtt tttttaactt gtatatgtaa agatcaattt ctcgtgacag taaataataa      1380
tccaatgtct tctgccaaat taatatatgt attcgtattt ttatatgaaa aaaaaaaaa       1440 aaaaaaaaa aaaaaaaaa aaaaaaaaa aaaa                                    1474

<210> SEQ ID NO 185
<211> LENGTH: 414
<212> TYPE: DNA
<213> ORGANISM: eucalyptus grandis

<400> SEQUENCE: 185
cacgctcgac gaattcggta ccccgggttc gaaatcgata agcttggatc caaagcaaca        60
cattgaactc tctctctctc tctctctctc tctctctctc tcccccaccc cccttccca       120 accccaccca catacagaca agtagatacg cgcacacaga agaagaaaag atggggggttt      180 caatgcagtc aatcgcacta gcgacggttc tggccgtcct aacgacatgg gcgtggaggg      240
cggtgaactg ggtgtggctg aggccgaaga ggctcgagag gcttctgaga cagcaaggtc      300
tctccggcaa gtcctacacc ttcctggtcg gcgacctcaa ggagaacctg cggatgctca      360
aggaagccaa gtccaagccc atcgccgtct ccgatgacat caagcctcgt ctct            414
```

PINUS RADIATA NUCLEIC ACIDS ENCODING O-METHYL TRANSFERASE AND METHODS FOR THE MODIFICATION OF PLANT LIGNIN CONTENT THEREWITH

CROSS-REFERENCE TO RELATED APPLICATIONS

This application is a continuation-in-part of U.S. patent application Ser. No. 08/975,316, filed Nov. 21, 1997, now U.S. Pat. No. 5,952,486 which is a continuation-in-part of U.S. patent application Ser. No. 08/713,000, filed Sep. 11, 1996, now U.S. Pat. No. 5,850,020.

TECHNICAL FIELD OF THE INVENTION

This invention relates to polynucleotides believed to be novel, including partial and extended sequences as well as probes and primers, constructs comprising the polynucleotides, biological materials, including plants, microorganisms and multicullular organisms incorporating the polynucleotides, polypeptides expressed by the polynucleotides, and methods for using the polynucleotides and polypeptides. The invention relates, more particularly, to the modification of lignin content and composition in biological materials including plants, to enzymes involved in the lignin biosynthetic pathway, and the polynucleotides encoding such enzymes.

BACKGROUND OF THE INVENTION

Lignin is an insoluble polymer that is primarily responsible for the rigidity of plant stems. Specifically, lignin serves as a matrix around the polysaccharide components of some plant cell walls. The higher the lignin content, the more rigid the plant. For example, tree species synthesize large quantities of lignin, with lignin constituting between 20% to 30% of the dry weight of wood. In addition to providing rigidity, lignin aids in water transport within plants by rendering cell walls hydrophobic and water impermeable. Lignin also plays a role in disease resistance of plants by impeding the penetration and propagation of pathogenic agents.

The high concentration of lignin in trees presents a significant problem in the paper industry wherein considerable resources must be employed to separate lignin from the cellulose fiber needed for the production of paper. Methods typically employed for the removal of lignin are highly energy- and chemical-intensive, resulting in increased costs and increased levels of undesirable waste products. In the U.S. alone, about 20 million tons of lignin are removed from wood per year.

Lignin is largely responsible for the digestibility, or lack thereof, of forage crops, with small increases in plant lignin content resulting in relatively high decreases in digestibility. For example, crops with reduced lignin content provide more efficient forage for cattle, with the yield of milk and meat being higher relative to the amount of forage crop consumed. During normal plant growth, the increase in dry matter content is accompanied by a corresponding decrease in digestibility. When deciding on the optimum time to harvest forage crops, farmers must therefore chose between a high yield of less digestible material and a lower yield of more digestible material.

For some applications, an increase in lignin content is desirable since increasing the lignin content of a plant would lead to increased mechanical strength of wood, changes in its color and increased resistance to rot. Mycorrhizal species composition and abundance may also be favorably manipulated by modifying lignin content and structural composition.

As discussed in detail below, lignin is formed by polymerization of at least three different monolignols that are synthesized in a multistep pathway, each step in the pathway being catalyzed by a different enzyme. It has been shown that manipulation of the number of copies of genes encoding certain enzymes, such as cinnamyl alcohol dehydrogenase (CAD) and caffeic acid 3-O-methyltransferase (COMT) results in modification of the amount of lignin produced; see, for example, U.S. Pat. No. 5,451,514 and PCT publication no. WO 94/23044. Furthermore, it has been shown that antisense expression of sequences encoding CAD in poplar leads to the production of lignin having a modified composition (Grand, C. et al. *Planta (Berl.)* 163:232–237 (1985)).

While polynucleotides encoding some of the enzymes involved in the lignin biosynthetic pathway have been isolated for certain species of plants, genes encoding many of the enzymes in a wide range of plant species have not yet been identified. Thus there remains a need in the art for materials useful in the modification of lignin content and composition in plants and for methods for their use.

SUMMARY OF THE INVENTION

Briefly, the present invention provides isolated polynucleotides identified in the attached Sequence Listing as SEQ ID NOS: 1–183, variants of those sequences, constructs comprising such sequences, extended sequences comprising the sequences of SEQ ID NOS: 1–183 and their variants, probes and primers corresponding to the sequences set out in SEQ ID NOS: 1–183 and their variants, polynucleotides comprising at least a specified number of contiguous residues of any of the polynucleotides identified as SEQ ID NOS: 1–183 (x-mers), all of which are referred to herein, collectively, as "polynucleotides of the present invention." Polynucleotides of the present invention are preferably obtainable from eucalyptus and pine species and preferably encode enzymes involved in the lignin biosynthetic pathway. Constructs incorporating such sequences, methods for using such sequences and constructs, and biological materials, including plant cells and plants having an altered genomic and/or lignin content and composition are also provided.

In one aspect, the present invention provides isolated polynucleotides encoding the following enzymes, or portions of the following enzymes: cinnamate 4-hydroxylase (C4H), coumarate 3-hydroxylase (C3H), phenolase (PNL), O-methyl transferase (OMT), cinnamyl alcohol dehydrogenase (CAD), cinnamoyl-CoA reductase (CCR), phenylalanine ammonia-lyase (PAL), 4-coumarate:CoA ligase (4CL), coniferol glucosyl transferase (CGT), coniferin beta-glucosidase (CBG), laccase (LAC) and peroxidase (POX), and ferulate-5-hydroxylase (F5H). In one embodiment, isolated polynucleotides comprise a nucleotide sequence selected from the group consisting of: (a) polynucleotides recited in SEQ ID NOS: 1–183; (b) complements of the polynucleotides recited in SEQ ID NOS: 1–183; (c) reverse complements of the sequences recited in SEQ ID NOS: 1–183; (d) reverse sequences of the sequences recited in SEQ ID NOS: 1–183; and (e) variants of the polynucleotides recited in SEQ ID NOS: 1–183. In another embodiment, polynucleotides comprise at least a specified number of contiguous residues (x-mers) of any of the polynucleotides of SEQ ID NOS: 1–183. In yet another aspect, polynucleotides comprise probes and primers corresponding to any of the polynucleotides of SEQ ID NOS: 1–183.

In another aspect, the present invention provides constructs comprising a polynucleotide of the present invention, either alone or in combination with one or more of the inventive sequences, or in combination with one or more known polynucleotides; together with host cells and transgenic cells comprising such constructs.

In a related aspect, the present invention provides constructs comprising, in the 5'-3' direction, a gene promoter sequence; an open reading frame coding for at least a functional portion of an enzyme encoded by a polynucleotide of the present invention; and a gene termination sequence. An open reading frame may be orientated in either a sense or antisense direction. DNA constructs comprising a non-coding region of a gene coding for an enzyme encoded by the above polynucleotides or a polynucleotide complementary to a non-coding region, together with a gene promoter sequence and a gene termination sequence, are also provided. Preferably, the gene promoter and termination sequences are functional in a host cell, such as a plant cell. Most preferably, the gene promoter and termination sequences are those of the original enzyme genes but others generally used in the art, such as the Cauliflower Mosaic Virus (CMV) promoter, with or without enhancers, such as the Kozak sequence or Omega enhancer, and *Agrobacterium tumefaciens* nopalin synthase terminator may be usefully employed in the present invention. Tissue-specific promoters may be employed in order to target expression to one or more desired tissues. In a preferred embodiment, the gene promoter sequence provides for transcription in xylem. The construct may further include a marker for the identification of transformed cells.

In a further aspect, transgenic cells, such as transgenic plant cells, comprising the constructs of the present invention are provided, together with plants comprising such transgenic cells, and fruits and seeds of such plants.

In yet another aspect, methods for modulating the lignin content and composition of a target organism such as a plant are provided, such methods including stably incorporating into the genome of the target plant a construct comprising a polynucleotide of the present invention. In a preferred embodiment, the target plant is a woody plant, preferably selected from the group consisting of eucalyptus and pine species, most preferably from the group consisting of *Eucalyptus grandis* and *Pinus radiata*. In a related aspect, a method for producing a plant having altered lignin content is provided, the method comprising transforming a plant cell with a construct comprising a polynucleotide of the present invention to provide a transgenic cell, and cultivating the transgenic cell under conditions conducive to regeneration and mature plant growth.

In yet a further aspect, the present invention provides methods for modifying the activity of an enzyme in a target organism such as a plant, comprising stably incorporating into the genome of the target organism a construct of the present invention. In a preferred embodiment, the target plant is a woody plant, preferably selected from the group consisting of eucalyptus and pine species, most preferably from the group consisting of *Eucalyptus grandis* and *Pinus radiata*.

The above-mentioned and additional features of the present invention and the manner of obtaining them will become apparent, and the invention will be best understood by reference to the following more detailed description, read in conjunction with the accompanying drawing.

DETAILED DESCRIPTION

Lignin is formed by polymerization of at least three different monolignols, primarily para-coumaryl alcohol, coniferyl alcohol and sinapyl alcohol. While these three types of lignin subunits are well known, it is possible that slightly different variants of these subunits may be involved in the lignin biosynthetic pathway in various plants. The relative concentration of these residues in lignin varies among different plant species and within species. In addition, the composition of lignin may also vary among different tissues within a specific plant. The three monolignols are derived from phenylalanine in a multistep process and are believed to be polymerized into lignin by a free radical mechanism.

Figure 1:
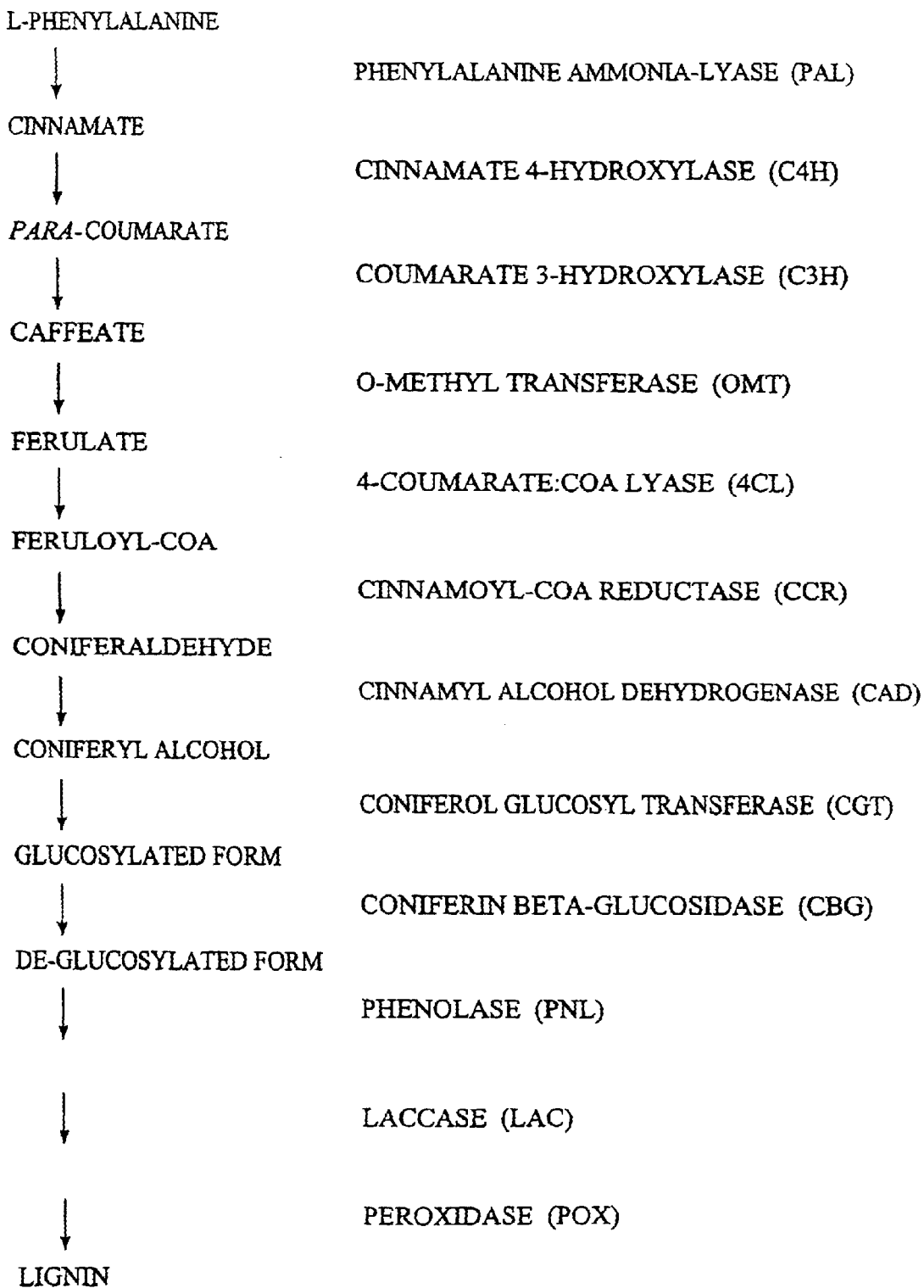
FIG. 1 is a schematic overview of the lignin biosynthetic pathway.

FIG. 1 shows the different steps in the biosynthetic pathway for coniferyl alcohol together with the enzymes responsible for catalyzing each step. para-Coumaryl alcohol and sinapyl alcohol are synthesized by similar pathways. Phenylalanine is first deaminated by phenylalanine ammonia-lyase (PAL) to give cinnamate which is then hydroxylated by cinnamate 4-hydroxylase (C4H) to form p-coumarate. p-Coumarate is hydroxylated by coumarate 3-hydroxylase to give caffeate. The newly added hydroxyl group is then methylated by O-methyl transferase (OMT) to give ferulate which is conjugated to coenzyme A by 4-coumarate:CoA ligase (4CL) to form feruloyl-CoA. Reduction of feruloyl-CoA to coniferaldehyde is catalyzed by cinnamoyl-CoA reductase (CCR). Coniferaldehyde is further reduced by the action of cinnamyl alcohol dehydrogenase (CAD) to give coniferyl alcohol which is then converted into its glucosylated form for export from the cytoplasm to the cell wall by coniferol glucosyl transferase (CGT). Following export, the de-glucosylated form of coniferyl alcohol is obtained by the action of coniferin beta-glucosidase (CBG). Finally, polymerization of the three monolignols to provide lignin is catalyzed by phenolase (PNL), laccase (LAC) and peroxidase (POX).

The formation of sinapyl alcohol involves an additional enzyme, ferulate-5-hydroxylase (F5H). For a more detailed review of the lignin biosynthetic pathway, see: Whetton, R. and Sederoff, R., *The Plant Cell,* 7:1001–1013 (1995).

Quantitative and qualitative modifications in plant lignin content are known to be induced by external factors such as light stimulation, low calcium levels and mechanical stress. Synthesis of new types of lignins, sometimes in tissues not normally lignified, can also be induced by infection with pathogens. In addition to lignin, several other classes of plant products are derived from phenylalanine, including flavonoids, coumarins, stilbenes and benzoic acid derivatives, with the initial steps in the synthesis of all these compounds being the same. Thus modification of the action of PAL, C4H, 4CL and other enzymes involved in the lignin biosynthetic pathway may affect the synthesis of other plant products in addition to lignin.

Using the methods and materials of the present invention, the lignin content of a plant may be modulated by modulating expression of polynucleotides of the present invention, or by modifying the polypeptides encoded by polynucleotides or the polynucleotides. The lignin content of a target organism, such as a plant, may be increased, for example, by incorporating additional copies of genes encoding enzymes involved in the lignin biosynthetic pathway into the genome of the target plant. Similarly, a decrease in lignin content can be obtained by transforming the target plant with antisense copies of such genes. In addition, the number of copies of genes encoding for different enzymes in the lignin biosynthetic pathway can be manipulated to modify the relative amount of each monolignol synthesized, thereby leading to the formation of lignin having altered composition. The alteration of lignin composition would be advantageous, for example, in applications of wood processing for paper, and may also be effective in altering the palatability of wood materials to rotting fungi.

In one embodiment, the present invention provides isolated complete or partial polynucleotides encoding, or partially encoding, enzymes involved in the lignin biosynthetic pathway, the polynucleotides preferably being obtainable from eucalyptus and pine species. Specifically, the present invention provides isolated polynucleotides encoding the enzymes CAD (SEQ ID NOS: 1, 7, 30, 71, 95, 112 and 164), PAL (SEQ ID NOS: 9–11, 16, 45–47, 97, 98, 100, 122, 123 and 176), C4H (SEQ ID NOS: 2, 3, 17, 48, 49, 92, 124, 125 and 153–163), C3H (SEQ ID NOS: 4, 18, 50–52, 93, 101, 126, 127 and 149–152), F5H (SEQ ID NOS: 19–21, 102, 103 and 169–171), OMT (SEQ ID NOS: 6, 22–25, 53–55, 94, 104–107 and 173–175), CCR (SEQ ID NOS: 8, 26–29, 58–70, 96, 108–111, 128–134 and 167), CGT (SEQ ID NOS: 31–33, 72, 113–115, 135 and 168), CBG (SEQ ID NOS: 34, 73–80, 136–141, 165 and 166), PNL (SEQ ID NOS: 5, 35, 36, 81, 116 and 183), LAC (SEQ ID NOS: 37–41, 82–84, 117, 118, 142–144 and 172), 4CL (SEQ ID NOS: 2, 56–57, 90, 147 and 158) and POX (SEQ ID NOS: 13, 42–44, 85–89, 91, 119–121, 145, 146, and 177–182).

Complements of such isolated polynucleotides, reverse complements of such isolated polynucleotides, and reverse sequences of such isolated polynucleotides, together with variants of such sequences, are also provided. The definition of the terms "complement", "reverse complement" and "reverse sequence", as used herein, is best illustrated by the following example. For the sequence 5' AGGACC 3', the complement, reverse complement and reverse sequence are as follows:

```
complement            3'TCCTGG 5'
reverse complement    3'GGTCCT 5'
reverse sequence      5'CCAGGA 3'.
```

The word "polynucleotide(s)," as used herein, means a polymeric collection of nucleotides and includes DNA and corresponding RNA molecules and both single and double stranded molecules, including HnRNA and mRNA molecules, sense and anti-sense strands of DNA and RNA molecules, and cDNA, genomic DNA, and wholly or partially synthesized polynucleotides. An HnRNA molecule contains introns and "corresponds to" a DNA molecule in a generally one-to-one manner. An mRNA molecule "corresponds to" an HnRNA and DNA molecule from which the introns have been excised. A polynucleotide of the present invention may be an entire gene, or any portion thereof. A gene is a DNA sequence which codes for a functional protein or RNA molecule. Operable anti-sense polynucleotides may comprise a fragment of the corresponding polynucleotide, and the definition of "polynucleotide" therefore includes all operable anti-sense fragments. Anti-sense polynucleotides and techniques involving anti-sense polynucleotides are well known in the art and are described, for example, in Robinson-Benion et al. (1995), Antisense techniques, *Methods in Enzymol.* 254(23): 363–375 and Kawasaki et al. (1996), *Artific. Organs* 20 (8): 836–848.

Identification of genomic DNA and heterologous species DNAs can be accomplished by standard DNA/DNA hybridization techniques, under appropriately stringent conditions, using all or part of a cDNA sequence as a probe to screen an appropriate library. Alternatively, PCR techniques using oligonucleotide primers that are designed based on known genomic DNA, cDNA and protein sequences can be used to amplify and identify genomic and cDNA sequences. Synthetic DNAs corresponding to the identified sequences and variants may be produced by conventional synthesis methods. All of the polynucleotides described herein are isolated and purified, as those terms are commonly used in the art.

As used herein, the term "oligonucleotide" refers to a relatively short segment of a polynucleotide sequence, generally comprising between 6 and 60 nucleotides, and comprehends both probes for use in hybridization assays and primers for use in the amplification of DNA by polymerase chain reaction.

As used herein, the term "x-mer," with reference to a specific value of "x," refers to a polynucleotide comprising at least a specified number ("x") of contiguous residues of any of the polynucleotides identified as SEQ ID NOS: 1–183. The value of x may be from about 20 to about 600, depending upon the specific sequence.

As used herein, the term "polypeptide" encompasses amino acid chains of any length, including full length proteins, wherein amino acid residues are linked by covalent peptide bonds. Polypeptides of the present invention may be naturally purified products, or may be produced partially or wholly using recombinant techniques. Such polypeptides may be glycosylated with mammalian or other eukaryotic carbohydrates or may be non-glycosylated.

According to one embodiment, "variants" of the polynucleotides of the present invention, including the polynucleotides set forth as SEQ ID NOS: 1–183, as that term is used herein, comprehends polynucleotides producing an "E" value of 0.01 or less, as described below, or having at least a specified percentage identity to a polynucleotide of the present invention, as described below. Polynucleotide variants of the present invention may be naturally occurring allelic variants, or non-naturally occurring variants.

Polynucleotides may be aligned and the "E" or Expectation values and percentage of identical nucleotides in a specified region measured against another polynucleotide using computer algorithms that are publicly available. Two exemplary algorithms for aligning and identifying the similarity of sequences are the BLASTN and FASTA algorithms. The BLASTN software is available on the NCBI anonymous FTP server. The BLASTN algorithm versio 2.0.4 [Feb. 24, 1998], set to the default parameters described in the documentation and distributed with the algorithm, is preferred for use in the determination of variants according to the present invention. The use of the BLAST family of algorithms, including BLASTN, is described at NCBI's website and in the publication of Altschul, Stephen F., et al. (1997), "Gapped BLAST and PSI-BLAST: a new generation of protein database search programs", *Nucleic Acids Res.* 25:3389–3402. The computer algorithm FASTA is available on the Internet. Version 2.0 u4, February 1996, set to the default parameters described in the documentation and distributed with the algorithm, is preferred for use in the determination of variants according to the present invention. The readme file for FASTA v2.0x that is distributed with the FASTA algorithm describes the use of the algorithm and describes the default parameters. The use of the FASTA algorithm is also described in W. R. Pearson and D. J. Lipman, "Improved Tools for Biological Sequence Analysis," PNAS 85:2444–2448 (1988) and W. R. Pearson, "Rapid and Sensitive Sequence Comparison with FASTP and FASTA," Methods in Enzymology 183:63–98 (1990).

The following running parameters are preferred for determination of alignments and similarities using BLASTN that contribute to the E values and percentage identity: Unix running command with default parameter values thus: blastall –p blastn –d embldb –e 10 –G 0 –E 0 –r 1 –v 30 –b 30 –i queryseq –o results; the Parameters are: –p Program Name [String]; –d Database [String]; –e Expectation value (E) [Real]; –G Cost to open a gap (zero invokes default behavior) [Integer]; –E Cost to extend a gap (zero invokes default behavior) [Integer]; –r Reward for a nucleotide match (blastn only) [Integer]; –v Number of one-line descriptions (V) [Integer]; –b Number of alignments to show (B) [Integer]; –i Query File [File In]; –o BLAST report Output File [File Out] Optional.

The "hits" to one or more database sequences by a queried sequence produced by BLASTN or FASTA or a similar algorithm align and identify similar portions of sequences. The hits are arranged in order of the degree of similarity and the length of sequence overlap. Hits to a database sequence generally represent an overlap over only a fraction of the sequence length of the queried sequence.

The BLASTN and FASTA algorithms produce "Expect" values for alignments. The Expect value (E) indicates the number of hits one can "expect" to see over a certain number of contiguous sequences by chance when searching a database of a certain size. The Expect value is used as a significance threshold for determining whether the hit to a database, such as the preferred EMBL database, indicates true similarity. For example, an E value of 0.1 assigned to a hit is interpreted as meaning that in a database of the size of the EMBL database, one might expect to see 0.1 matches over the aligned portion of the sequence with a similar score simply by chance. The aligned and matched portions of the sequences, then, have a probability of 90% of being the same by this criterion. For sequences having an E value of 0.01 or less over aligned and matched portions, the probability of finding a match by chance in the EMBL database is 1% or less using the BLASTN or FASTA algorithm.

According to one embodiment, "variant" polynucleotides, with reference to each of the polynucleotides of the present invention, preferably comprise sequences having the same number or fewer nucleotides than each of the polynucleotides of the present invention and producing an E value of 0.01 or less when compared to the polynucleotide of the present invention. That is, a variant polynucleotide is any sequence that has at least a 99% probability of being the same as the polynucleotide of the present invention, measured as having an E value of 0.01 or less using the BLASTN or FASTA algorithms set at the default parameters. According to a preferred embodiment, a variant polynucleotide is a sequence having the same number or fewer nucleotides than a polynucleotide of the present invention that has at least a 99% probability of being the same as the polynucleotide of the present invention, measured as having an E value of 0.01 or less using the BLASTN or FASTA algorithms set at the default parameters.

According to another preferred embodiment, variants of polynucleotides of the present invention are determined by aligning and comparing polynucleotides using the FASTA or BLASTN algorithms set at default parameters, as described above. Hits identified using the BLASTN or FASTA algorithms that are to a portion of a sequence representing less than 20%, preferably less than 10%, of the length of the queried sequence, are eliminated for purposes of determining variants. According to this embodiment, a variant polynucleotide is a sequence that has an E value of 0.01 or less using the BLASTN or FASTA algorithms set at default parameters after elimination of all hits representing less than 20%, preferably less than 10% of the length of the queried polynucleotide.

Alternatively, variant polynucleotides of the present invention may comprise a sequence exhibiting at least about 40%, more preferably at least about 60%, more preferably yet at least about 75%, and most preferably at least about 90% similarity to a polynucleotide of the present invention, determined as described below. The percentage similarity is determined by aligning sequences using one of the BLASTN or FASTA algorithms, set at default parameters; identifying the number of identical nucleotides over the aligned portions; dividing the number of identical nucleotides by the total number of nucleotides of the polynucleotide of the present invention; and then multiplying by 100 to determine the percentage similarity. For example, a polynucleotide of the present invention having 220 nucleic acids has a hit to a polynucleotide sequence in the EMBL database having 520 nucleotides over a stretch of 23 nucleotides in the alignment produced by the BLASTN algorithm using the default parameters. The 23 nucleotide hit includes 21 identical nucleotides, one gap and one different nucleotide. The percentage similarity of the polynucleotide of the present invention to the hit in the EMBL library is thus 21/220 times 100, or 9.5%. The polynucleotide sequence in the EMBL database is thus not a variant of a polynucleotide of the present invention.

Alternatively, variant polynucleotides of the present invention hybridize to a polynucleotide of the present invention under stringent hybridization conditions. As used herein, "stringent conditions" mean prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

The polynucleotides of the present invention, including variants, may be isolated from various libraries assembled from plant or non-plant organisms, or may be synthesized using techniques that are well known in the art. Polynucleotides of the present invention may be isolated by high throughput sequencing of cDNA libraries prepared from *Eucalyptus grandis* and *Pinus radiata* as described below in Examples 1 and 2. Alternatively, oligonucleotide probes based on the sequences provided in SEQ ID NO: 1–183 may be synthesized and used to identify positive clones in either cDNA or genomic DNA libraries from *Eucalyptus grandis* and *Pinus radiata* by means of hybridization or PCR techniques. Probes may be shorter than the sequences provided herein but should be at least about 10, preferably at least about 15 and most preferably at least about 20 nucleotides in length. Hybridization and PCR techniques suitable for use with such oligonucleotide probes are well known in the art. Positive clones may be analyzed by restriction enzyme digestion, DNA sequencing or the like.

The polynucleotides of the present invention may be synthesized, for example, using automated oligonucleotide synthesizers (e.g. Beckman Oligo 1000M DNA Synthesizer) to obtain polynucleotide segments of up to 50 or more nucleotides. A plurality of such polynucleotide segments may then be ligated using standard DNA manipulation techniques that are well known in the art of molecular biology. One conventional and exemplary polynucleotide synthesis technique involves synthesis of a single stranded polynucleotide segment having, for example, 80 nucleotides, and hybridizing that segment to a synthesized complementary 85 nucleotides segment to produce a 5 nucleotide overhang. The next segment may then be synthesized in a similar fashion, with a 5 nucleotide overhang on the opposite strand. The "sticky" ends ensure proper ligation when the two portions are hybridized. In this way, a complete polynucleotide of the present invention may be synthesized entirely in vitro.

Variants of the polynucleotides of the present invention derived from other eucalyptus and pine species, as well as from other commercially important species utilized by the lumber industry, are contemplated. These include the following gymnosperms, by way of example: loblolly pine *Pinus taeda*, slash pine *Pinus elliotti*, sand pine *Pinus clausa*, longleaf pine *Pinus palustrus*, shortleaf pine *Pinus echinata*, ponderosa pine *Pinus ponderosa*, Jeffrey pine *Pinus jeffrey*, red pine *Pinus resinosa*, pitch pine *Pinus rigida*, jack pine *Pinus banksiana*, pond pine *Pinus serotina*, Eastern white pine *Pinus strobus*, Western white pine *Pinus monticola*, sugar pine *Pinus lambertiana*, Virginia pine *Pinus virginiana*, lodgepole pine *Pinus contorta*, Caribbean pine *Pinus caribaea*, *P. pinaster*, Calabrian pine *P. brutia*, Afghan pine *P. eldarica*, Coulter pine *P. coulteri*, European pine *P. nigra* and *P. sylvestris*; Douglas-fir *Pseudotsuga menziesii*; the hemlocks which include Western hemlock *Tsuga heterophylla*, Eastern hemlock *Tsuga canadensis*, Mountain hemlock *Tsuga mertensiana*; the spruces which include the Norway spruce *Picea abies*, red spruce *Picea rubens*, white spruce *Picea glauca*, black spruce *Picea mariana*, Sitka spruce *Picea sitchensis*, Englemann spruce *Picea engelmanni*, and blue spruce *Picea pungens*; redwood *Sequoia sempervirens*; the true firs include the Alpine fir *Abies lasiocarpa*, silver fir *Abies amabilis*, grand fir *Abies grandis*, nobel fir *Abies procera*, white fir *Abies concolor*, California red fir *Abies magnifica*, and balsam fir *Abies balsamea*, the cedars which include the Western red cedar *Thuja plicata*, incense cedar *libocedrus decurrens*, Northern white cedar *Thuja occidentalis*, Port Orford cedar *Chamaecyparis lawsoniona*, Atlantic white cedar *Chamaecyparis thyoides*, Alaska yellow-cedar *Chamaecyparis nootkatensis*, and Eastern red cedar *Huniperus virginiana*; the larches which include Eastern larch *Larix laricina*, Western larch *Larix occidentalis*, European larch *Larix decidua*, Japanese larch *Larix leptolepis*, and Siberian larch *Larix siberica*; bold cypress *Taxodium distichum* and Giant sequoia *Sequoia gigantea*; and the following angiosperms, by way of example: *Eucalyptus alba*, *E. bancroftii*, *E. botyroides*, *E. bridgesiana*, *E. calophylla*, *E. camaldulensis*, *E. citriodora*, *E. cladocalyx*, *E. coccifera*, *E. curtisii*, *E. dalrympleana*, *E. deglupta*, *E. delagatensis*, *E. diversicolor*, *E. dunnii*, *E. ficifolia*, *E. globulus*, *E. gomphocephala*, *E. gunnii*, *E. henryi*, *E. laevopinea*, *E. macarthurii*, *E. macrorhyncha*, *E. maculata*, *E. marginata*, *E. megacarpa*, *E. melliodora*, *E. nicholii*, *E. nitens*, *E. nova-angelica*, *E. obliqua*, *E. obtusiflora*, *E. oreades*, *E. pauciflora*, *E. polybractea*, *E. regnans*, *E. resinifera*, *E. robusta*, *E. rudis*, *E. saligna*, *E. sideroxylon*, *E. stuartiana*, *E. tereticornis*, *E. torelliana*, *E. urnigera*, *E. urophylla*, *E. viminalis*, *E. viridis*, *E. wandoo* and *E. youmanni*.

The polynucleotides identified as SEQ ID NOS: 1–183 may be "partial" or full length sequences. Partial sequences do not represent the full coding portion of a gene encoding a naturally occurring polypeptide. The partial polynucleotide sequences disclosed herein may be employed to obtain the corresponding full length genes for various species and organisms by, for example, screening DNA expression libraries using hybridization probes based on the polynucleotides of the present invention, or using PCR amplification with primers based upon the polynucleotides of the present invention. In this way one can, using methods well known in the art, extend a polynucleotide of the present invention upstream and downstream of the corresponding mRNA, as well as identify the corresponding genomic DNA, including the promoter and enhancer regions, of the complete gene.

The present invention thus comprehends isolated polynucleotides comprising a sequence identified in SEQ ID NOS: 1–183, or a variant of one of the specified sequences, that encode a functional polypeptide, including full length genes. Such extended polynucleotides may have a length of from about 50 to about 4,000,nucleotides or base pairs, and preferably have a length of less than about 4,000 nucleotides or base pairs, more preferably a length of less than about 3,000 nucleotides or base pairs, more preferably yet a length of less than about 2,000 nucleotides or base pairs. Under some circumstances, extended polynucleotides of the present invention may have a length of less than about 1,800 nucleotides or base pairs, preferably less than about 1,600 nucleotides or base pairs, more preferably less than about 1,400 nucleotides or base pairs, more preferably yet less than about 1,200 nucleotides or base pairs, and most preferably less than about 1,000 nucleotides or base pairs.

Polynucleotides of the present invention also comprehend polynucleotides comprising at least a specified number of contiguous residues (x-mers) of any of the polynucleotides identified as SEQ ID NOS: 1–183 or their variants. According to preferred embodiments, the value of x is preferably at least 20, more preferably at least 40, more preferably yet at least 60, and most preferably at least 80. Thus, polynucleotides of the present invention include polynucleotides comprising a 20-mer, a 40-mer, a 60-mer, an 80-mer, a 100-mer, a 120-mer, a 150-mer, a 180-mer, a 220-mer a 250-mer, or a 300-mer, 400-mer, 500-mer or 600-mer of a polynucleotide identified as SEQ ID NOS: 1–183 or a variant of any x-mer. That is, the definitions for variants described above in terms of E values, % similarity and hybridization, apply also to any x-mer of any polynucleotide of the present invention.

Polynucleotide probes and primers complementary to and/or corresponding to SEQ ID NOS: 1–183, and variants of those sequences, are also comprehended by the present invention. Such oligonucleotide probes and primers are substantially complementary to the polynucleotide of interest. An oligonucleotide probe or primer is described as "corresponding to" a polynucleotide of the present invention, including one of the sequences set out as SEQ ID NOS: 1–183 or a variant, if the oligonucleotide probe or primer, or its complement, is contained within one of the sequences set out as SEQ ID NOS: 1–183 or a variant of one of the specified sequences.

Two single stranded sequences are said to be substantially complementary when the nucleotides of one strand, optimally aligned and compared, with the appropriate nucleotide insertions and/or deletions, pair with at least 80%, preferably at least 90% to 95%, and more preferably at least 98% to 100%, of the nucleotides of the other strand. Alternatively, substantial complementarity exists when a first DNA strand will selectively hybridize to a second DNA strand under stringent hybridization conditions. Stringent hybridization conditions for determining complementarity include salt conditions of less than about 1 M, more usually less than about 500 mM and preferably less than about 200 mM. Hybridization temperatures can be as low as 5° C., but are generally greater than about 22° C., more preferably greater than about 30° C. and most preferably greater than about 37° C. Longer DNA fragments may require higher hybridization temperatures for specific hybridization. Since the stringency of hybridization may be affected by other factors such as probe composition, presence of organic solvents and extent of base mismatching, the combination of parameters is more important than the absolute measure of any one alone. The DNAs from plants or samples or products containing plant material can be either genomic DNA or DNAs derived by preparing cDNA from the RNAs present in the sample.

In addition to DNA-DNA hybridization, DNA-RNA or RNA-RNA hybridization assays are also possible. In the first case, the mRNAs from expressed genes would then be detected instead of genomic DNA or cDNA derived from mRNA of the sample. In the second case, RNA probes could be used. In addition, artificial analogs of DNA hybridizing specifically to target sequences could also be used.

In specific embodiments, the oligonucleotide probes and/or primers comprise at least about 6 contiguous residues, more preferably at least about 10 contiguous residues, and most preferably at least about 20 contiguous residues complementary to a polynucleotide sequence of the present invention. Probes and primers of the present invention may be from about 8 to 100 base pairs in length or, preferably, from about 10 to 50 base pairs in length or, more preferably, from about 15 to 40 base pairs in length. The probes can be easily selected using procedures well known in the art, taking into account DNA-DNA hybridization stringencies, annealing and melting temperatures, potential for formation of loops and other factors, which are well known in the art. Tools and software suitable for designing probes, and especially suitable for designing PCR primers, are available on the Internet. Preferred techniques for designing PCR primers are also disclosed in Dieffenbach, C. W and Dvksler, G. S. (1995) PCR primer: a laboratory manual. CSHL press, Cold Spring Harbor, USA.

A plurality of oligonucleotide probes or primers corresponding to polynucleotides of the present invention may be provided in a kit form. Such kits generally comprise multiple DNA or oligonucleotide probes, each probe being specific for a polynucleotide sequence. Kits of the present invention may comprise one or more probes or primers corresponding to a polynucleotide of the present invention, including a polynucleotide sequence identified in SEQ ID NOS: 1–183.

In one embodiment useful for high-throughput assays, the oligonucleotide probe kits of the present invention comprise multiple probes in an array format, wherein each probe is immobilized in a predefined, spatially addressable location on the surface of a solid substrate. Array formats which may be usefully employed in the present invention are disclosed, for example, in U.S. Pat. Nos. 5,412,087, 5,545,531, and PCT Publication No. WO 95/00530, the disclosures of which are hereby incorporated by reference.

The significance of high-throughput screening systems is apparent for applications such as plant breeding and quality control operations in which there is a need to identify large numbers of seed lots and plant seedlings, to examine samples or products for unwanted plant materials, to identify plants or samples or products containing plant material for quarantine purposes etc. or to ascertain the true origin of plants or samples or products containing plant material. Screening for the presence or absence of polynucleotides of the present invention used as identifiers for tagging plants is valuable for later detecting the amount of gene flow in plant breeding, introgression of genes via dispersed pollen, etc.

In this manner, oligonucleotide probe kits of the present invention may be employed to examine the presence/absence (or relative amounts in case of mixtures) of polynucleotides of the present invention in different samples or products containing different materials rapidly and in a cost-effective manner. Examples of plant species that may be examined using the present invention, include forestry species, such as pine and eucalyptus species, other tree species, agricultural plants including crop and forage plants, and horticultural plants.

Another aspect of the present invention involves collections of polynucleotides of the present invention. A collection of polynucleotides of the present invention, particularly the polynucleotides identified as SEQ ID NOS: 1–183 and variants and x-mers thereof, may be recorded and/or stored on a storage medium and subsequently accessed for purposes of analysis, comparison, etc. Suitable storage media include magnetic media such as magnetic diskettes, magnetic tapes, CD-ROM storage media, optical storage media, and the like. Suitable storage media and methods for recording and storing information, as well as accessing information such as polynucleotide sequences recorded on such media, are well known in the art. The polynucleotide information stored on the storage medium is preferably computer-readable and may be used for analysis and comparison of the polynucleotide information.

Another aspect of the present invention thus involves storage medium on which are recorded a collection of the polynucleotides of the present invention, particularly a collection of the polynucleotides identified as SEQ ID NOS: 1–183 and variants thereof, as well as x-mers of the polynucleotides of SEQ ID NOS: 1–183, and extended sequences, probes and primers comprising or correspond to a polynucleotide of SEQ ID NOS: 1–183. According to one embodiment, the storage medium includes a collection of at least 20, preferably at least 50, more preferably at least 100, and most preferably at least 200 of the polynucleotides of the present invention, preferably the polynucleotides identified as SEQ ID NOS: 1–183, or variants of those polynucleotides.

In another aspect, the present invention provides DNA constructs comprising, in the 5'-3' direction, a gene promoter sequence; an open reading frame coding for at least a functional portion of a polypeptide encoded by a polynucleotide of the present invention; and a gene termination sequence. As used herein, the "functional portion" of an enzyme is a portion that contains an active site essential for affecting a metabolic step, i.e. a portion of the molecule that is capable of binding one or more reactants or is capable of improving or regulating the rate of reaction. An active site may be made up of separate portions present on one or more polypeptide chains and will generally exhibit high substrate specificity. The term "enzyme encoded by a nucleotide sequence" as used herein, includes enzymes encoded by a nucleotide sequence which includes the partial isolated polynucleotides of the present invention.

The open reading frame may be orientated in either a sense or antisense direction. For applications where amplification of lignin synthesis is desired, the open reading frame may be inserted in the construct in a sense orientation, such that transformation of a target organism with the construct will lead to an increase in the number of copies of the gene and therefore an increase in the amount of enzyme. When down-regulation of lignin synthesis is desired, the open reading frame may be inserted in the construct in an antisense orientation, such that the RNA produced by transcription of the polynucleotide is complementary to the endogenous mRNA sequence. This, in turn, will result in a decrease in the number of copies of the gene and therefore a decrease in the amount of enzyme. Alternatively, regulation may be achieved by inserting appropriate sequences or subsequences (e.g. DNA or RNA) in ribozyme constructs.

Constructs comprising a non-coding region of a gene coding for an enzyme encoded by the above DNA sequences or a nucleotide sequence complementary to a non-coding region, together with a gene promoter sequence and a gene termination sequence, are also provided. As used herein the term "non-coding region" includes both transcribed sequences which are not translated, and non-transcribed sequences within about 2000 base pairs 5' or 3' of the translated sequences or open reading frames. Examples of non-coding regions which may be usefully employed in the inventive constructs include introns and 5'-non-coding leader sequences. Transformation of a target plant with such a DNA construct may lead to a reduction in the amount of lignin synthesized by the plant by the process of cosuppression, in a manner similar to that discussed, for example, by Napoli et al. (*Plant Cell* 2:279–290, 1990) and de Carvalho Niebel et al. (*Plant Cell* 7:347–358, 1995).

The constructs of the present invention further comprise a gene promoter sequence and a gene termination sequence, operably linked to the Polynucleotide to be transcribed, which control expression of the gene. The gene promoter sequence is generally positioned at the 5' end of the Polynucleotide to be transcribed, and is employed to initiate transcription of the Polynucleotide. Gene promoter sequences are generally found in the 5' non-coding region of a gene but they may exist in introns (Luehrsen, K. R., *Mol. Gen. Genet.* 225:81–93, 1991) or in the coding region, as for example in PAL of tomato (Bloksberg, 1991, Studies on the Biology of Phenylalanine Ammonia Lyase and Plant Pathogen Interaction. Ph.D. Thesis, Univ. of California, Davis, University Microfilms International order number 9217564). When the construct includes an open reading frame in a sense orientation, the gene promoter sequence also initiates translation of the open reading frame. For DNA constructs comprising either an open reading frame in an antisense orientation or a non-coding region, the gene promoter sequence consists only of a transcription initiation site having a RNA polymerase binding site.

A variety of gene promoter sequences which may be usefully employed in the DNA constructs of the present invention are well known in the art. The promoter gene sequence, and also the gene termination sequence, may be endogenous to the target plant host or may be exogenous, provided the promoter is functional in the target host. For example, the promoter and termination sequences may be from other plant species, plant viruses, bacterial plasmids and the like. Preferably, gene promoter and termination sequences are from the inventive sequences themselves.

Factors influencing the choice of promoter include the desired tissue specificity of the construct, and the timing of transcription and translation. For example, constitutive promoters, such as the 35S Cauliflower Mosaic Virus (CaMV 35S) promoter, will affect the activity of the enzyme in all parts of the plant. Use of a tissue specific promoter will result in production of the desired sense or antisense RNA only in the tissue of interest. With DNA constructs employing inducible gene promoter sequences, the rate of RNA polymerase binding and initiation can be modulated by external stimuli, such as light, heat, anaerobic stress, alteration in nutrient conditions and the like. Temporally regulated promoters can be employed to effect modulation of the rate of RNA polymerase binding and initiation at a specific time during development of a transformed cell. Preferably, the original promoters from the enzyme gene in question, or promoters from a specific tissue-targeted gene in the organism to be transformed, such as eucalyptus or pine are used. Other examples of gene promoters which may be usefully employed in the present invention include, mannopine synthase (mas), octopine synthase (ocs) and those reviewed by Chua et al. (*Science*, 244:174–181, 1989).

The gene termination sequence, which is located 3' to the Polynucleotide to be transcribed, may come from the same gene as the gene promoter sequence or may be from a different gene. Many gene termination sequences known in the art may be usefully employed in the present invention, such as the 3' end of the *Agrobacterium tumefaciens* nopaline synthase gene. However, preferred gene terminator sequences are those from the original enzyme gene or from the target species to be transformed.

The DNA constructs of the present invention may also contain a selection marker that is effective in plant cells, to allow for the detection of transformed cells containing the inventive construct. Such markers, which are well known in the art, typically confer resistance to one or more toxins. One example of such a marker is the NPTII gene whose expression results in resistance to kanamycin or hygromycin, antibiotics which are usually toxic to plant cells at a moderate concentration (Rogers et al. in *Methods for Plant Molecular Biology*, A. Weissbach and H. Weissbach, eds., Academic Press Inc., San Diego, Calif. (1988)). Alternatively, the presence of the desired construct in transformed cells can be determined by means of other techniques well known in the art, such as Southern and Western blots.

Techniques for operatively linking the components of the inventive DNA constructs are well known in the art and include the use of synthetic linkers containing one or more restriction endonuclease sites as described, for example, by Maniatis et al., (*Molecular Cloning: A Laboratory Manual*, Cold Spring Harbor Laboratories, Cold Spring Harbor, N.Y., 1989). The DNA construct of the present invention may be linked to a vector having at least one replication system, for example, *E. coli*, whereby after each manipulation, the resulting construct can be cloned and sequenced and the correctness of the manipulation determined.

The DNA constructs of the present invention may be used to transform a variety of plants, both monocotyledonous (e.g. grasses, corn, grains, oat, wheat and barley), dicotyledonous (e.g. Arabidopsis, tobacco, legumes, alfalfa, oaks, eucalyptus, maple), and Gymnosperms (e.g. Scots pine (Aronen, Finnish Forest Res. Papers, vol. 595, 1996), white spruce (Ellis et al., *Biotechnology* 11:94–92, 1993), larch (Huang et al., *In Vitro Cell* 27:201–207, 1991). In a preferred embodiment, the inventive DNA constructs are employed to transform woody plants, herein defined as a tree or shrub whose stem lives for a number of years and increases in diameter each year by the addition of woody tissue. Preferably the target plant is selected from the group consisting of eucalyptus and pine species, most preferably from the group consisting of *Eucalyptus grandis* and *Pinus radiata*. As discussed above, transformation of a plant with a DNA construct including an open reading frame coding for an enzyme encoded by an inventive Polynucleotide wherein the open reading frame is orientated in a sense direction will generally lead to an increase in lignin content of the plant or, in some cases, to a decrease by cosuppression. Transformation of a plant with a DNA construct comprising an open reading frame in an antisense orientation or a non-coding (untranslated) region of a gene will generally lead to a decrease in the lignin content of the transformed plant.

The production of RNA in target cells may be controlled by choice of the promoter sequence, or by selecting the number of functional copies or the site of integration of the polynucleotides incorporated into the genome of the target organism. A target plant may be transformed with more than one construct of the present invention, thereby modulating the lignin biosynthetic pathway for the activity of more than one enzyme, affecting enzyme activity in more than one tissue or affecting enzyme activity at more than one expression time. Similarly, a construct may be assembled containing more than one open reading frame coding for an enzyme encoded by a polynucleotide of the present invention or more than one non-coding region of a gene coding for such an enzyme. The polynucleotides of the present invention may also be employed in combination with other known sequences encoding enzymes involved in the lignin biosynthetic pathway. In this manner, it may be possible to add a lignin biosynthetic pathway to a non-woody plant to produce a new woody plant.

Techniques for stably incorporating DNA constructs into the genome of target plants are well known in the art and include *Agrobacterium tumefaciens* mediated introduction, electroporation, protoplast fusion, injection into reproductive organs, injection into immature embryos, high velocity projectile introduction and the like. The choice of technique will depend upon the target plant to be transformed. For example, dicotyledonous plants and certain monocots and gymnosperms may be transformed by Agrobacterium Ti plasmid technology, as described, for example by Bevan (*Nucl. Acid Res.* 12:8711–8721, 1984). Targets for the introduction of the DNA constructs of the present invention include tissues, such as leaf tissue, disseminated cells, protoplasts, seeds, embryos, meristematic regions; cotyledons, hypocotyls, and the like. One preferred method for transforming eucalyptus and pine is a biolistic method using pollen (see, for example, Aronen 1996, Finnish Forest Res. Papers vol. 595, 53 pp) or easily regenerable embryonic tissues. Other transformation techniques which may be usefully employed in the inventive methods include those taught by Ellis et al. (*Plant Cell Reports*, 8:16–20, 1989), Wilson et al. (*Plant Cell Reports* 7:704–707, 1989) and Tautorus et al. (*Theor. Appl. Genet.* 78:531–536, 1989).

Once the cells are transformed, cells having the inventive DNA construct incorporated in their genome may be selected by means of a marker, such as the kanamycin resistance marker discussed above. Transgenic cells may then be cultured in an appropriate medium to regenerate whole plants, using techniques well known in the art. In the case of protoplasts, the cell wall is allowed to reform under appropriate osmotic conditions. In the case of seeds or embryos, an appropriate germination or callus initiation medium is employed. For explants, an appropriate regeneration medium is used. Regeneration of plants is well established for many species. For a review of regeneration of forest trees see Dunstan et al., Somatic embryogenesis in woody plants. In: Thorpe, T. A. ed., 1995: in vitro embryogenesis of plants. Vol. 20 in Current Plant Science and Biotechnology in Agriculture, Chapter 12, pp. 471–540. Specific protocols for the regeneration of spruce are discussed by Roberts et al., (Somatic Embryogenesis of Spruce. In: *Synseed. Applications of synthetic seed to crop improvement*. Redenbaugh, K., ed. CRC Press, Chapter 23, pp. 427–449, 1993). The resulting transformed plants may be reproduced sexually or asexually, using methods well known in the art, to give successive generations of transgenic plants.

In yet a further aspect, the present invention provides methods for modifying the level (concentration) or activity of a polypeptide in a host organism, comprising stably incorporating into the genome of the plant a construct comprising a polynucleotide of the present invention. The DNA constructs of the present invention may be used to transform a variety of organisms. Such organisms include plants, such as monocotyledonous angiosperms (e.g. grasses, corn, grains, oat, wheat and barley), and dicotyledonous angiosperms (e.g. Arabidopsis, tobacco, legumes, alfalfa, oaks, eucalyptus, maple), and gymnosperms (e.g. Scots pine (Aronen, Finnish Forest Res. Papers, vol. 595, 1996), white spruce (Ellis et al., *Biotechnology* 11:94–92, 1993), larch (Huang et al., *In Vitro Cell* 27:201–207, 1991).

In preferred embodiments, the constructs of the present invention are employed to transform woody plants, herein defined as a tree or shrub having a stem that lives for a number of years and increases in diameter each year as a consequence of the addition of woody tissue. The target plant is preferably selected from the group consisting of eucalyptus and pine species, most preferably from the group consisting of *Eucalyptus grandis* and *Pinus radiata*, but also including any of the species in the following list:

Pines: *Pinus banksiana, Pinus brutia, Pinus caribaea, Pinus clausa, Pinus contorta, Pinus coulteri, Pinus echinata, Pinus eldarica, Pinus ellioti, Pinus jeffreyi, Pinus lambertiana, Pinus monticola, Pinus nigra, Pinus palustrus, Pinus pinaster, Pinus ponderosa, Pinus resinosa, Pinus rigida, Pinus serotina, Pinus strobus, Pinus sylvestris, Pinus taeda, Pinus virginiana.*

Other gymnosperms: *Abies amabilis, Abies balsamea, Abies concolor, Abies grandis, Abies lasiocarpa, Abies magnifica, Abies procera, Chamaecyparis lawsoniona, Chamaecyparis nootkatensis, Chamaecyparis thyoides, Huniperus virginiana, Larix decidua, Larix laricina, Larix leptolepis, Larix occidentalis, Larix siberica, Libocedrus decurrens, Picea abies, Picea engelmanni, Picea glauca, Picea mariana, Picea pungens, Picea rubens, Picea sitchensis, Pseudotsuga menziesii, Sequoia gigantea, Sequoia sempervirens, Taxodium distichum, Tsuga canadensis, Tsuga heterophylla, Tsuga mertensiana, Thuja occidentalis, Thuja plicata.*

Eucalypts: *Eucalyptus alba, Eucalyptus bancroftii, Eucalyptus botyroides, Eucalyptus bridgesiana, Eucalyptus* calophylla, Eucalyptus camaldulensis, Eucalyptus citriodora, Eucalyptus cladocalyx, Eucalyptus coccifera, Eucalyptus curtisii, Eucalyptus dalrympleana, Eucalyptus deglupta, Eucalyptus delagatensis, Eucalyptus diversicolor, Eucalyptus dunnii, Eucalyptus ficifolia, Eucalyptus globulus, Eucalyptus gomphocephala, Eucalyptus gunnii, Eucalyptus henryi, Eucalyptus laevopinea, Eucalyptus macarthurni, Eucalyptus macrorhyncha, Eucalyptus maculata, Eucalyptus marginata, Eucalyptus megacarpa, Eucalyptus melliodora, Eucalyptus nicholii, Eucalyptus nitens, Eucalyptus nova-anglica, Eucalyptus obliqua, Eucalyptus obtusiflora, Eucalyptus oreades, Eucalyptus pauciflora, Eucalyptus polybractea, Eucalyptus regnans, Eucalyptus resinifera, Eucalyptus robusta, Eucalyptus rudis, Eucalyptus saligna, Eucalyptus sideroxylon, Eucalyptus stuartiana, Eucalyptus tereticornis, Eucalyptus torelliana, Eucalyptus urnigera, Eucalyptus urophylla, Eucalyptus viminalis, Eucalyptus viridis, Eucalyptus wandoo, Eucalyptus youmanni.

Further, the polynucleotides of the present invention have particular application for use as non-disruptive tags for marking organisms, particularly plants. Other organisms may, however, be tagged with the polynucleotides of the present invention, including commercially valuable animals, fish, bacteria and yeasts.

Constructs comprising polynucleotides of the present invention may be stably introduced into an organism as heterologous, non-functional, non-disruptive tags. It is then possible to identify the origin or source of the organism at a later date by determining the presence or absence of the tag(s) in a sample of material.

Detection of the tag(s) may be accomplished using a variety of conventional techniques, and will generally involve the use of nucleic acid probes. Sensitivity in assaying the presence of probe can be usefully increased by using branched oligonucleotides, as described in Nucleic Acids Research 25(23):4842–4849 (Horn, T, Chang, C A & Urdea M S, 1997, Chemical synthesis and characterization of branched oligodeoxyribonucleotides (bDNA) for use as signal amplifiers in nucleic acid quantification assays.), enabling to detect as few as 50 DNA molecules in the sample.

The following examples are offered by way of illustration and not by way of limitation.

EXAMPLE 1

Isolation and Characterization of cDNA Clones from *Eucalyptus grandis*

Two *Eucalyptus grandis* cDNA expression libraries (one from a mixture of various tissues from a single tree and one from leaves of a single tree) were constructed and screened as follows.

mRNA was extracted from the plant tissue using the protocol of Chang et al. (*Plant Molecular Biology Reporter* 11:113–116 (1993)) with minor modifications. Specifically, samples were dissolved in CPC-RNAXB (100 mM Tris-Cl, pH 8,0; 25 mM EDTA; 2.0 M NaCl; 2% CTAB; 2% PVP and 0.05% Spermidine*3 HCl) and extracted with chloroform:isoamyl alcohol, 24:1. mRNA was precipitated with ethanol and the total RNA preparate was purified using a Poly(A) Quik mRNA Isolation Kit (Stratagene, La Jolla, Calif.). A cDNA expression library was constructed from the purified mRNA by reverse transcriptase synthesis followed by insertion of the resulting cDNA clones in Lambda ZAP using a ZAP Express cDNA Synthesis Kit (Stratagene), according to the manufacturer's protocol. The resulting cDNAs were packaged using a Gigapack II Packaging Extract (Stratagene) employing 1 µl of sample DNA from the 5 µl ligation mix. Mass excision of the library was done using XL1-Blue MRF' cells and XLOLR cells (Stratagene) with ExAssist helper phage (Stratagene). The excised phagemids were diluted with NZY broth (Gibco BRL, Gaithersburg, Md.) and plated out onto LB-kanamycin agar plates containing X-gal and isopropylthio-beta-galactoside (IPTG).

Of the colonies plated and picked for DNA miniprep, 99% contained an insert suitable for sequencing. Positive colonies were cultured in NZY broth with kanamycin and cDNA was purified by means of alkaline lysis and polyethylene glycol (PEG) precipitation. Agarose gel at 1% was used to screen sequencing templates for chromosomal contamination. Dye primer sequences were prepared using a Turbo Catalyst 800 machine (Perkin Elmer/Applied Biosystems, Foster City, Calif.) according to the manufacturer's protocol.

DNA sequences for positive clones were obtained using an Applied Biosystems Prism 377 sequencer. cDNA clones were sequenced first from the 5' end and, in some cases, also from the 3' end. For some clones, internal sequence was obtained using subcloned fragments. Subcloning was performed using standard procedures of restriction mapping and subcloning to pBluescript II SK+ vector.

The determined cDNA sequences were compared to known sequences in the EMBL database (release 46, March 1996) using the FASTA algorithm of February 1996 (version 2.0u4) (available on the Internet). Multiple alignments of redundant sequences were used to build up reliable consensus sequences. Based on similarity to known sequences from other plant species, the isolated polynucleotides of the present invention were identified as encoding a specified enzyme.

Using the procedures described above, cDNA sequences derived from the *Eucalyptus grandis* library encoding the following enzymes were isolated: PAL (SEQ ID NOS: 16 and 100); C4H (SEQ ID NOS: 17, 153, 154, and 161); C3H (SEQ ID NOS: 18, 101, 149 and 150); F5H (SEQ ID NOS: 19–21, 102, 103 and 169–171); OMT (SEQ ID NOS: 22–25, 104–107, 173 and 174); CCR (SEQ ID NOS: 26–29 and 108–111); CAD (SEQ ID NOS: 1, 30 and 112); CGT (SEQ ID NOS: 31–33 and 113–115); CBG (SEQ ID NOS: 34, 165 and 166); PNL (SEQ ID NOS: 35, 36 and 116); LAC (SEQ ID NOS: 37–41, 117 and 118); and POX (SEQ ID NOS: 42–44, 119–121 and 179).

EXAMPLE 2

Isolation and Characterization of cDNA Clones from *Pinus radiata* a) Isolation of cDNA Clones by High Through-put Screening

A *Pinus radiata* cDNA expression library was constructed from xylem and screened as described above in Example 1. DNA sequences for positive clones were obtained using forward and reverse primers on an Applied Biosystems Prism 377 sequencer and the determined sequences were compared to known sequences in the database as described above.

Based on similarity to known sequences from other plant species, the isolated DNA sequences were identified as encoding the enzymes C4H (SEQ ID NOS: 2, 3, 48, 49, 92, 124, 125, 155–160, 162 and 163), C3H (SEQ ID NOS: 4, 50–52, 93, 126, 127, 151 and 152), PNL (SEQ ID NOS: 5, 81 and 183), OMT (SEQ ID NOS: 6, 53–55, 94 and 175), CAD (SEQ ID NOS: 7, 71, 95 and 164), CCR (SEQ ID NOS: 8, 58–70, 96, 128–134 and 167), PAL (SEQ ID NOS:

9–11, 45–47, 97, 98, 122, 123 and 176), 4CL (SEQ ID NOS: 12, 56, 57, 90, 99, 147 and 148), CGT (SEQ ID NOS: 72, 135 and 168), CBG (SEQ ID NOS: 73–80 and 136–141), LAC (SEQ ID NOS: 82–84, 142–144 and 172); and POX (SEQ ID NOS: 85–89, 91, 145, 146, 177, 178 and 180–182).

b) Isolation of cDNA Clones by PCR

Two PCR probes, hereinafter referred to as LNB010 and LNB011 (SEQ ID NO: 14 and 15, respectively) were designed based on conserved domains in the following peroxidase sequences previously identified in other species: vanpox, hvupox6, taepox, hvupox1, osapox, ntopox2, ntopox1, lespox, pokpox, luspox, athpox, hrpox, spopox, and tvepox (Genbank accession nos. D11337, M83671, X56011, X58396, X66125, J02979, D11396, X71593, D11102, L07554, M58381, X57564, Z22920, and Z31011, respectively).

RNA was isolated from pine xylem and first strand cDNA was synthesized as described above. This cDNA was subjected to PCR using 4 µM LNB010, 4 µM LNB011, 1×Kogen's buffer, 0.1 mg/ml BSA, 200 mM dNTP, 2 mM $Mg^{2+}$, and 0.1 U/µl of Taq polymerase (Gibco BRL). Conditions were 2 cycles of 2 min at 94° C., 1 min at 55° C. and 1 min at 72° C.; 25 cycles of 1 min at 94° C., 1 min at 55° C., and 1 min at 72° C.; and 18 cycles of 1 min at 94° C., 1 min at 55° C., and 3 min at 72° C. in a Stratagene Robocycler. The gene was re-amplified in the same manner. A band of about 200 bp was purified from a TAE agarose gel using a Schleicher & Schuell Elu-Quik DNA purification kit and clones into a T-tailed pBluescript vector (Marchuk D. et al., *Nucleic Acids Res.* 19:1154, 1991). Based on similarity to known sequences, the isolated gene (SEQ ID NO: 13) was identified as encoding pine peroxidase (POX).

EXAMPLE 3

Use of an O-methyltransferase (OMT) Gene to Modify Lignin Biosynthesis a) Transformation of Tobacco Plants with a *Pinus radiata* OMT Gene Sense and anti-sense constructs containing a Polynucleotide including the coding region of OMT (SEQ ID NO: 53) from *Pinus radiata* were inserted into *Agrobacterium tumefaciens* LBA4301 (provided as a gift by Dr. C. Kado, University of California, Davis, Calif.) by direct transformation using published methods (see, An G, Ebert P R, Mitra A, Ha S B: Binary Vectors. In: Gelvin S B, Schilperoort R A (eds) *Plant Molecular Biology Manual,* Kluwer Academic Publishers, Dordrecht (1988)). The presence and integrity of the transgenic constructs were verified by restriction digestion and DNA sequencing.

Tobacco (*Nicotiana tabacum* cv. Samsun) leaf sections were transformed using the method of Horsch et al. (*Science,* 227:1229–1231, 1985). Five independent transformed plant lines were established for the sense construct and eight independent transformed plant lines were established for the anti-sense construct for OMT. Transformed plants containing the appropriate lignin gene construct were verified using Southern blot experiments. A "+" in the column labeled "Southern" in Table 1 below indicates that the transformed plant lines were confirmed as independent transformed lines.

b) Expression of Pinus OMT in Transformed Plants

Total RNA was isolated from each independent transformed plant line created with the OMT sense and anti-sense constructs. The RNA samples were analysed in Northern blot experiments to determine the level of expression of the transgene in each transformed line. The data shown in the column labeled "Northern" in Table 1 shows that the transformed plant lines containing the sense and anti-sense constructs for OMT all exhibited high levels of expression, relative to the background on the Northern blots. OMT expression in sense plant line number 2 was not measured because the RNA sample showed signs of degradation. There was no detectable hybridisation to RNA samples from empty vector-transformed control plants.

c) Modulation of OMT Enzyme Activity in Transformed Plants

The total activity of OMT enzyme, encoded by the Pinus OMT gene and by the endogenous tobacco OMT gene, in transformed tobacco plants was analysed for each transformed plant line created with the OMT sense and anti-sense constructs. Crude protein extracts were prepared from each transformed plant and assayed using the method of Zhang et al. (*Plant Physiol.,* 113:65–74, 1997). The data contained in the column labeled "Enzyme" in Table 1 shows that the transformed plant lines containing the OMT sense construct generally had elevated OMT enzyme activity, with a maximum of 199%, whereas the transformed plant lines containing the OMT anti-sense construct generally had reduced OMT enzyme activity, with a minimum of 35%, relative to empty vector-transformed control plants. OMT enzyme activity was not estimated in sense plant line number 3.

d) Effects of Pinus OMT on Lignin Concentration in Transformed Plants

The concentration of lignin in the transformed tobacco plants was determined using the well-established procedure of thioglycolic acid extraction (see, Freudenberg et al. in *Constitution and Biosynthesis of Lignin,* Springer-Verlag, Berlin, 1968). Briefly, whole tobacco plants, of an average age of 38 days, were frozen in liquid nitrogen and ground to a fine powder in a mortar and pestle. 100 mg of frozen powder from one empty vector-transformed control plant line, the five independent transformed plant lines containing the sense construct for OMT and the eight independent transformed plant lines containing the anti-sense construct for OMT were extracted individually with methanol, followed by 10% thioglycolic acid and finally dissolved in 1 M NaOH. The final extracts were assayed for absorbance at 280 nm. The data shown in the column labelled "TGA" in Table 1 shows that the transformed plant lines containing the sense and the anti-sense OMT gene constructs all exhibited significantly decreased levels of lignin, relative to the empty vector-transformed control plant lines.

TABLE 1

| plant line | transgene | orientation | Southern | Northern | Enzyme | TGA |
| --- | --- | --- | --- | --- | --- | --- |
| 1 | control | na | + | blank | 100 | 104 |
| 1 | OMT | sense | + | 2.9E+6 | 86 | 55 |
| 2 | OMT | sense | + | na | 162 | 58 |
| 3 | OMT | sense | + | 4.1E+6 | na | 63 |
| 4 | OMT | sense | + | 2.3E+6 | 142 | 66 |
| 5 | OMT | sense | + | 3.6E+5 | 199 | 75 |
| 1 | OMT | anti-sense | + | 1.6E+4 | 189 | 66 |
| 2 | OMT | anti-sense | + | 5.7E+3 | 35 | 70 |
| 3 | OMT | anti-sense | + | 8.0E+3 | 105 | 73 |
| 4 | OMT | anti-sense | + | 1.4E+4 | 109 | 74 |
| 5 | OMT | anti-sense | + | 2.5E+4 | 87 | 78 |
| 6 | OMT | anti-sense | + | 2.5E+4 | 58 | 84 |
| 7 | OMT | anti-sense | + | 2.5E+4 | 97 | 92 |
| 8 | OMT | anti-sense | + | 1.1E+4 | 151 | 94 |

These data clearly indicate that lignin concentration, as measured by the TGA assay, can be directly manipulated by either sense or anti-sense expression of a lignin biosynthetic gene such as OMT.

EXAMPLE 4

Use of a 4-Coumarate:CoA ligase (4CL) Gene to Modify Lignin Biosynthesis a) Transformation of Tobacco Plants with a *Pinus radiata* 4CL Gene Sense and anti-sense constructs containing a Polynucleotide including the coding region of 4CL (SEQ ID NO: 56) from *Pinus radiata* were inserted into *Agrobacterium tumefaciens* LBA4301 by direct transformation as described above. The presence and integrity of the transgenic constructs were verified by restriction digestion and DNA sequencing.

Tobacco (*Nicotiana tabacum* cv. Samsun) leaf sections were transformed as described above. Five independent transformed plant lines were established for the sense construct and eight independent transformed plant lines were established for the anti-sense construct for 4CL. Transformed plants containing the appropriate lignin gene construct were verified using Southern blots experiments. A "+" in the column labeled "Southern" in Table 2 indicates that the transformed plant lines listed were confirmed as independent transformed lines.

b) Expression of Pinus 4CL in Transformed Plants

Total RNA was isolated from each independent transformed plant line created with the 4CL sense and anti-sense constructs. The RNA samples were analysed in Northern blot experiments to determine the level of expression of the transgene in each transformed line. The data shown in the column labelled "Northern" in Table 2 below shows that the transformed plant lines containing the sense and anti-sense constructs for 4CL all exhibit high levels of expression, relative to the background on the Northern blots. 4CL expression in anti-sense plant line number 1 was not measured because the RNA was not available at the time of the experiment. There was no detectable hybridisation to RNA samples from empty vector-transformed control plants.

c) Modulation of 4CL Enzyme Activity in Transformed Plants

The total activity of 4CL enzyme, encoded by the Pinus 4CL gene and by the endogenous tobacco 4CL gene, in transformed tobacco plants was analysed for each transformed plant line created with the 4CL sense and anti-sense constructs. Crude protein extracts were prepared from each transformed plant and assayed using the method of Zhang et al. (*Plant Physiol.*, 113:65–74, 1997). The data contained in the column labeled "Enzyme" in Table 2 shows that the transformed plant lines containing the 4CL sense construct had elevated 4CL enzyme activity, with a maximum of 258%, and the transformed plant lines containing the 4CL anti-sense construct had reduced 4CL enzyme activity, with a minimum of 59%, relative to empty vector-transformed control plants.

d) Effects of Pinus 4CL on Lignin Concentration in Transformed Plants

The concentration of lignin in samples of transformed plant material was determined as described in Example 3. The data shown in the column labelled "TGA" in Table 2 shows that the transformed plant lines containing the sense and the anti-sense 4CL gene constructs all exhibited significantly decreased levels of lignin, relative to the empty vector-transformed control plant lines. These data clearly indicate that lignin concentration, as measured by the TGA assay, can be directly manipulated by either sense or anti-sense expression of a lignin biosynthesis gene such as 4CL.

TABLE 2

| plant line | transgene | orientation | Southern | Northern | Enzyme | TGA |
| --- | --- | --- | --- | --- | --- | --- |
| 1 | control | na | + | blank | 100 | 92 |
| 2 | control | na | + | blank | 100 | 104 |
| 1 | 4CL | sense | + | 2.3E+4 | 169 | 64 |
| 2 | 4CL | sense | + | 4.5E+4 | 258 | 73 |
| 3 | 4CL | sense | + | 3.1E+4 | 174 | 77 |
| 4 | 4CL | sense | + | 1.7E+4 | 164 | 80 |
| 5 | 4CL | sense | + | 1.6E+4 | 184 | 92 |
| 1 | 4CL | anti-sense | + | na | 59 | 75 |
| 2 | 4CL | anti-sense | + | 1.0E+4 | 70 | 75 |
| 3 | 4CL | anti-sense | + | 9.6E+3 | 81 | 80 |
| 4 | 4CL | anti-sense | + | 1.2E+4 | 90 | 83 |
| 5 | 4CL | anti-sense | + | 4.7E+3 | 101 | 88 |
| 6 | 4CL | anti-sense | + | 3.9E+3 | 116 | 89 |
| 7 | 4CL | anti-sense | + | 1.8E+3 | 125 | 94 |
| 8 | 4CL | anti-sense | + | 1.7E+4 | 106 | 97 |

EXAMPLE 5

Transformation of Tobacco Using the Inventive Lignin Biosynthetic Genes

Sense and anti-sense constructs containing polynucleotides including the coding regions of C3H (SEQ ID NO: 18), F5H (SEQ ID NO: 19), CCR (SEQ ID NO: 25) and CGT (SEQ ID NO: 31) from *Eucalyptus grandis*, and PAL (SEQ ID NO: 45 and 47), C4H (SEQ ID NO: 48 and 49), PNL (SEQ ID NO: 81) and LAC (SEQ ID NO: 83) from *Pinus radiata* were inserted into *Agrobacterium tumefaciens* LBA4301 by direct transformation as described above. The presence and integrity of the transgenic constructs were verified by restriction digestion and DNA sequencing.

Tobacco (*Nicotiana tabacum* cv. Samsun) leaf sections were transformed as described in Example 3. Up to twelve independent transformed plant lines were established for each sense construct and each anti-sense construct listed in the preceding paragraph. Transformed plants containing the appropriate lignin gene construct were verified using Southern blot experiments. All of the transformed plant lines analysed were confirmed as independent transformed lines.

EXAMPLE 6

Manipulation of Lignin Content in Transformed Plants a) Determination of Transgene Expression by Northern Blot Experiments Total RNA was isolated from each independent transformed plant line described in Example 5. The RNA samples were analysed in Northern blot experiments to determine the level of expression of the transgene in each transformed line. The column labelled "Northern" in Table 3 shows the level of transgene expression for all plant lines assayed, relative to the background on the Northern blots. There was no detectable hybridisation to RNA samples from empty vector-transformed control plants.

b) Determination of Lignin Concentration in Transformed Plants

The concentration of lignin in empty vector-transformed control plant lines and in up to twelve independent transformed lines for each sense construct and each anti-sense construct described in Example 5 was determined as described in Example 3. The column labelled "TGA" in Table 3 shows the thioglycolic acid extractable lignins for all plant lines assayed, expressed as the average percentage of TGA extractable lignins in transformed plants versus control plants. The range of variation is shown in parentheses.

TABLE 3

| transgene | orientation | no. of lines | Northern | TGA |
|---|---|---|---|---|
| control | na | 3 | blank | 100 (92–104) |
| C3H | sense | 5 | 3.7E+4 | 74 (67–85) |
| F5H | sense | 10 | 5.8E+4 | 70 (63–79) |
| F5H | anti-sense | 9 | 5.8E+4 | 73 (35–93) |
| CCR | sense | 1 | na | 74 |
| CCR | anti-sense | 2 | na | 74 (62–86) |
| PAL | sense | 5 | 1.9E+5 | 77 (71–86) |
| PAL | anti-sense | 4 | 1.5E+4 | 62 (37–77) |
| C4H | anti-sense | 10 | 5.8E+4 | 86 (52–113) |
| PNL | anti-sense | 6 | 1.2E+4 | 88 (70–114) |
| LAC | sense | 5 | 1.7E+5 | na |
| LAC | anti-sense | 12 | 1.7E+5 | 88 (73–114) |

Transformed plant lines containing the sense and the anti-sense lignin biosynthetic gene constructs all exhibited significantly decreased levels of lignin, relative to the empty vector-transformed control plant lines. The most dramatic effects on lignin concentration were seen in the F5H anti-sense plants with as little as 35% of the amount of lignin in control plants, and in the PAL anti-sense plants with as little as 37% of the amount of lignin in control plants. These data clearly indicate that lignin concentration, as measured by the TGA assay, can be directly manipulated by conventional anti-sense methodology and also by sense over-expression using the inventive lignin biosynthetic genes.

EXAMPLE 7

Modulation of Lignin Enzyme Activity in Transformed Plants

The activities and substrate specificities of selected lignin biosynthetic enzymes were assayed in crude extracts from transformed tobacco plants containing sense and anti-sense constructs for PAL (SEQ ID NO: 45), PNL (SEQ ID NO: 81) and LAC (SEQ ID NO: 83) from *Pinus radiata*, and CGT (SEQ ID NO: 31) from *Eucalyptus grandis*.

Enzyme assays were performed using published methods for PAL (Southerton, S. G. and Deverall, B. J., *Plant Path.* 39:223–230, 1990), CGT (Vellekoop, P. et al., *FEBS,* 3:36–40, 1993), PNL (Espin, C. J. et al., *Phytochemistry*, 44:17–22, 1997) and LAC (Bao, W. et al., *Science*, 260:672–674, 1993). The data shown in the column labelled "Enzyme" in Table 4 shows the average enzyme activity from replicate measures for all plant lines assayed, expressed as a percent of enzyme activity in empty vector-transformed control plants. The range of variation is shown in parentheses.

TABLE 4

| Transgene | orientation | no. of lines | enzyme |
|---|---|---|---|
| control | na | 3 | 100 |
| PAL | sense | 5 | 87 (60–124) |
| PAL | anti-sense | 3 | 53 (38–80) |
| CGT | anti-sense | 1 | 89 |
| PNL | anti-sense | 6 | 144 (41–279) |
| LAC | sense | 5 | 78 (16–240) |
| LAC | anti-sense | 11 | 64 (14–106) |

All of the transformed plant lines, except the PNL anti-sense transformed plant lines, showed average lignin enzyme activities which were significantly lower than the activities observed in empty vector-transformed control plants. The most dramatic effects on lignin enzyme activities were seen in the PAL anti-sense transformed plant lines in which all of the lines showed reduced PAL activity and in the LAC anti-sense transformed plant lines which showed as little as 14% of the LAC activity in empty vector-transformed control plant lines.

EXAMPLE 8

Functional Identification of Lignin Biosynthetic Genes

Sense constructs containing polynucleotides including the coding regions for PAL (SEQ ID NO: 47), OMT (SEQ ID NO: 53), 4CL (SEQ ID NO: 56 and 57) and POX (SEQ ID NO: 86) from *Pinus radiata,* and OMT (SEQ ID NO: 23 and 24), CCR (SEQ ID NO: 26–28), CGT (SEQ ID NO: 31 and 33) and POX (SEQ ID NO: 42 and 44) from *Eucalyptus grandis* were inserted into the commercially available protein expression vector, pProEX-1 (Gibco BRL). The resultant constructs were transformed into *E. coli* XL1-Blue (Stratagene), which were then induced to produce recombinant protein by the addition of IPTG. Purified proteins were produced for the Pinus OMT and 4CL constructs and the Eucalyptus OMT and POX constructs using Ni column chromatography (Janknecht, R. et al., *Proc. Natl. Acad. Sci.,* 88:8972–8976, 1991). Enzyme assays for each of the purified proteins conclusively demonstrated the expected substrate specificity and enzymatic activity for the genes tested.

The data for two representative enzyme assay experiments, demonstrating the verification of the enzymatic activity of a *Pinus radiata* 4CL gene (SEQ ID NO: 56) and a *Pinus radiata* OMT gene (SEQ ID NO: 53), are shown in Table 5. For the 4CL enzyme, one unit equals the quantity of protein required to convert the substrate into product at the rate of 0.1 absorbance units per minute. For the OMT enzyme, one unit equals the quantity of protein required to convert 1 pmole of substrate to product per minute.

TABLE 5

| trans-gene | purification step | total ml extract | total mg protein | total units activity | % yield activity | fold purification |
|---|---|---|---|---|---|---|
| 4CL | crude | 10 ml | 51 mg | 4200 | 100 | 1 |
|  | Ni column | 4 ml | 0.84 mg | 3680 | 88 | 53 |
| OMT | crude | 10 ml | 74 mg | 4600 | 100 | 1 |
|  | Ni column | 4 ml | 1.2 mg | 4487 | 98 | 60 |

The data shown in Table 5 indicate that both the purified 4CL enzyme and the purified OMT enzyme show high activity in enzyme assays, confirming the identification of the 4CL and OMT genes described in this application. Crude protein preparations from *E. coli* transformed with empty vector show no activity in either the 4CL or the OMT enzyme assay.

EXAMPLE 9

Demonstration of the Presence/Absence of Unique Sequence Identifiers in Plants

Transgenic tobacco plants were created using unique identifier sequences which are not found in tobacco. The unique identifier sequences inserted were isolated from *Pinus radiata,* SEQ ID NO: 184, and *Eucalyptus grandis,* SEQ ID NO: 185. The unique identifier sequences were inserted into *Agrobacterium tumefaciens* LBA4301 (provided as a gift by Dr. C. Kado, University of California, Davis, Calif.) by direct transformation using published methods (see, An G, Ebert P R, Mitra A, Ha S B: Binary Vectors. In: Gelvin S B, Schilperoort R A (eds) Plant Molecular Biology Manual, Kluwer Academic Publishers, Dordrecht (1988)). The presence and integrity of the unique identifier sequences in the Agrobacterium transgenic constructs were verified by restriction digestion and DNA sequencing.

Tobacco (*Nicotiana tabacum* cv. Samsun) leaf sections were transformed using the method of Horsch et al. (*Science,* 227:1229–1231, 1985). Three independent transformed plant lines were established for each unique sequence identifier used. Two empty-vector control plant lines were established using an empty gene transfer vector which lacked a unique sequence identifier.

The uniqueness of the sequence identifiers was assayed using Southern blot analyses to test for the presence of the sequence identifier in the genome of the plants. If the sequence identifier is unique and therefore useful as a tag, then the sequence identifier should be clearly absent in plants which have not been tagged and it should be clearly present in plants which have been tagged. In the present example, the unique identifiers would be expected to be absent in the empty-vector transformed control plants. The unique identifier would be expected to be present in the transgenic plants transformed with the unique sequence identifiers.

Figure 2:
FIG. 2 illustrates genomic DNA samples from tobacco plants created in a tagging experiment using a unique sequence identifier from Pinus (left panel) and a unique sequence identifier from Eucalyptus (right panel). In both panels, lanes A and B contain DNA samples from empty-vector transformed control plants and lanes C–E contain DNA samples from plants transformed with a unique sequence identifier.

Genomic DNA was prepared from empty-vector transformed control plants and plants transformed with unique sequence identifiers using the cetyltrimethyl-ammonium bromide (CTAB) extraction method of Murray and Thompson (Nucleic Acids Research, 8:4321–4325, 1980). The DNA samples were digested with the restriction enzyme EcoRI in the case of the plants transformed with the Pinus unique sequence identifier (SEQ ID NO: 184) and the restriction enzyme XbaI in the case of the plants transformed with the Eucalyptus unique sequence identifier (SEQ ID NO: 185). The DNA fragments produced in the restriction digests were resolved on a 1% agarose gel; the left panel of FIG. 2 and the right panel of FIG. 2 show the DNA fragment patterns of the DNA samples from the Pinus and Eucalyptus experiments, respectively.

After the agarose gel electrophoresis step, the DNA samples were transferred to Hybond-N+ brand nylon membranes (Amersham Life Science, Little Chalfont, Buckinghamshire, England) using methods established by Southern (J. Mol. Bio., 98:503–517). The nylon membranes were probed with radioactively-labeled probes for the unique sequence identifiers identified above and washed at high stringency (final wash: 0.5×salt sodium citrate buffer (SSC) plus 0.1% sodium dodecyl sulfate (SDS), 15 minutes at 65° C.). The hybridisation of the probes to complementary sequences in the genomic DNA samples was detected using auto-radiography. The results are shown in FIGS. 3 and 4.

Figure 3:
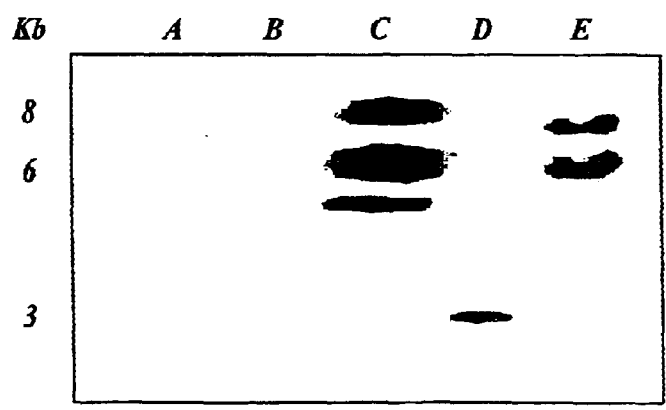
FIG. 3 demonstrates detection of a Pinus unique sequence identifier in transformed tobacco plants. Lanes A and B show the hybridization of a probe from SEQ ID NO: 184 to the genomic DNA of tobacco plants which lack the Pinus unique sequence identifier (empty-vector transformed control plants). Lanes C–E show the hybridization of the probe to the genomic DNA of tobacco plants containing one to three copies of the Pinus unique sequence identifier.

FIG. 3 (corresponding to the left panel of FIG. 2) shows the hybridisation pattern detected in the Southern blot analysis using a probe derived from the Pinus sequence identifier (SEQ ID NO: 184). Lanes A–B contain DNA samples from empty-vector transformed control plants and lanes C–E contain DNA from plants transformed with SEQ ID NO: 184. There is no hybridization in lanes A–B indicating that SEQ ID NO: 184 is not present in empty-vector transformed tobacco plants; that is, SEQ ID NO: 184 is a unique tag suitable for unambiguous marking of tobacco plants. There is strong hybridisation in lanes C–E indicating that the plants which received SEQ ID NO: 184 via transformation have been clearly and unambiguously tagged with the unique sequence contained in SEQ ID NO: 184.

Figure 4:
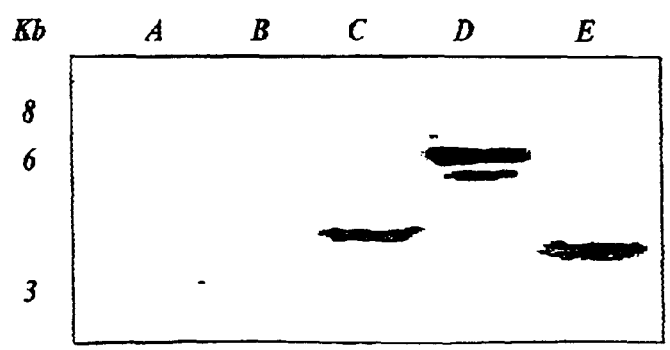
FIG. 4 demonstrates detection of a Eucalyptus unique sequence identifier in transformed tobacco plants. Lanes A and B show the hybridization of a probe from SEQ ID NO: 185 to the genomic DNA of tobacco plants which lack the Eucalyptus unique sequence identifier (empty-vector transformed control plants). Lanes C–E show the hybridization of the probe to the genomic DNA of tobacco plants containing one to two copies of the Eucalyptus unique sequence identifier.

FIG. 4 (corresponding to the right panel of FIG. 2) shows the hybridization pattern detected in the Southern blot analysis using a probe derived from the Eucalyptus sequence identifier (SEQ ID NO: 185). Lanes A–B contain DNA samples from empty-vector transformed control plants and lanes C–E contain DNA from plants transformed with SEQ ID NO: 185. There is no hybridisation in lanes A–B indicating that SEQ ID NO: 185 is not present in empty-vector transformed tobacco plants; that is, SEQ ID NO: 185 is a unique tag suitable for unambiguous marking of tobacco plants. There is strong hybridisation in lanes C–E indicating that the plants which received SEQ ID NO: 185 via transformation have been clearly and unambiguously tagged with the unique sequence contained in SEQ ID NO: 185.

The present example clearly demonstrates the utility of the sequences disclosed in this specification for the purposes of unambiguously tagging transgenic materials. A unique sequence was selected from a large number of potential tags and shown to be absent in the genome of the organism to be tagged. The tag was inserted into the genome of the organism to be tagged and a well-established DNA detection method was used to clearly detect the unique sequence identifier used as the tag.

Because of the sequence-specific detection methods used in the example, a user of the invention disclosed in this specification has both a high likelihood of finding a sequence identifier, among the list which has been disclosed, which will be useful for tagging any given organism and an unequivocal method for demonstrating that a tagged organism could only have acquired a given tag through the deliberate addition of the unique sequence to the genome of the organism to be tagged. If the user of this invention maintains the precise sequence of the tag used in a given organism as a secret, then any disputes as to the origin and history of the organism can be unambiguously resolved using the tag detection techniques demonstrated in the present example.

SEQ ID NOS: 1–185 are set out in the attached Sequence Listing. The codes for nucleotide sequences used in the attached Sequence Listing, including the symbol "n," conform to WIPO Standard ST.25 (1998), Appendix 2, Table 1.

All references cited herein, including patent references and non-patent publications, are hereby incorporated by reference in their entireties.

While in the foregoing specification this invention has been described in relation to certain preferred embodiments, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An isolated polynucleotide comprising SEQ ID NO: 94.

2. An isolated polynucleotide encoding O-methyl transferase, wherein said polynucleotide comprises a sequence that hybridizes under stringent hybridization conditions to SEQ ID NO:94, wherein the stringent hybridization conditions comprise prewashing in a solution of 6×SSC, 0.2% SDS; hybridizing at 65° C., 6×SSC, 0.2% SDS overnight; followed by two washes of 30 minutes each in 1×SSC, 0.1% SDS at 65° C. and two washes of 30 minutes each in 0.2×SSC, 0.1% SDS at 65° C.

3. An isolated polynucleotide comprising selected from the group consisting of:

the complement of SEQ ID NO:94.

4. A DNA construct comprising, in the 5'-3' direction:

(a) a promoter sequence;

(b) a polynucleotide sequence comprising SEQ ID NO:94; and (c) a transcription termination sequence.

5. A DNA construct comprising a polynucleotide according to any one of claims 2–3.

6. The construct of claim 4, wherein the polynucleotide is in the sense orientation.

7. The construct of claim 4, wherein the promoter sequence and transcription termination sequence are functional in a plant host.

8. The construct of claim 4, wherein the promoter sequence is functional in xylem tissue.

9. The construct of claim 4, further comprising a marker gene for identification of transformed cells.

10. A transgenic plant or bacterial host cell comprising the construct according to claim 5.

11. A transgenic plant cell comprising the construct of claim 4.

12. The transgenic plant cell of claim 11, wherein the polynucleotide is in the sense orientation.

13. A plant comprising the transgenic plant cell according to claim 11, or transgenic fruit or transgenic seeds of said plant.

14. The plant of claim 13 wherein the plant is a woody plant.

15. The plant of claim 14 wherein the plant is selected from the group consisting of eucalyptus and pine species.

16. A method for decreasing the lignin content of a plant, comprising stably incorporating into the genome of the plant the construct of claim 14.

17. The method of claim 16 wherein the polynucleotide is in the sense orientation.

18. The method of claim 16 wherein the plant is a woody plant.

19. The method of claim 18, wherein the plant is selected from the group consisting of eucalyptus and pine species.

20. A method for producing a plant having decreased lignin content, comprising:

(a) transforming a plant cell with the construct of claim 4 to provide a transgenic plant cell; and (b) regenerating a plant from the transgenic plant cell, wherein the plant has decreased lignin content.

21. The method of claim 20 wherein the polynucleotide is in the sense orientation.

22. The method of claim 20 wherein the plant is a woody plant.

23. The method of claim 22 wherein the plant is selected from the group consisting of eucalyptus and pine species.

24. A method of increasing the activity of OMT in a plant comprising stably incorporating into the genome of the plant the construct of claim 4.

25. The method of claim 24 wherein the polynucleotide is in the sense orientation.

26. The method of claim 24 wherein the plant is a woody plant.

27. The method of claim 26 wherein the plant is selected from the group consisting of eucalyptus and pine species.

* * * * *

UNITED STATES PATENT AND TRADEMARK OFFICE
CERTIFICATE OF CORRECTION

| | |
|---|---|
| PATENT NO. | : 6,653,528 B1 |
| DATED | : November 25, 2003 |
| INVENTOR(S) | : Leonard N. Bloksberg and Ilkka Havukkala |

It is certified that error appears in the above-identified patent and that said Letters Patent is hereby corrected as shown below:

Title page,
Item [73], Assignee, replace "Genesis Research and Development Corporation Limited, Parnell (NZ); Rubicam Forests Industries Limited, Auckland (NZ)" with -- Genesis Research and Development Corporation Limited, Parnell (NZ); Rubicon Forests Industries Limited, Auckland (NZ) --

Column 163,
Lines 64-65, replace "comprising selected from the group consisting of:" with -- comprising --

Column 165,
Line 16, replace "the construct of claim 14" with -- the construct of claim 4 --

Signed and Sealed this

Ninth Day of November, 2004

JON W. DUDAS
*Director of the United States Patent and Trademark Office*